(12) United States Patent
Arnett et al.

(10) Patent No.: US 10,357,561 B2
(45) Date of Patent: Jul. 23, 2019

(54) BTNL9 PROTEINS, NUCLEIC ACIDS, AND ANTIBODIES AND USES THEREOF

(71) Applicant: Amgen Inc., Thousand Oaks, CA (US)

(72) Inventors: Heather A. Arnett, Seattle, WA (US); Sabine S. Escobar, Sammamish, WA (US); Ryan M. Swanson, Seattle, WA (US); Joanne L. Viney, Belmont, MA (US)

(*) Notice: Subject to any disclaimer, the term of this patent is extended or adjusted under 35 U.S.C. 154(b) by 456 days.

(21) Appl. No.: 14/704,794

(22) Filed: May 5, 2015

(65) Prior Publication Data
US 2015/0344554 A1 Dec. 3, 2015

Related U.S. Application Data

(63) Continuation of application No. 13/640,232, filed as application No. PCT/US2011/031811 on Apr. 8, 2011, now abandoned.

(60) Provisional application No. 61/322,800, filed on Apr. 9, 2010.

(51) Int. Cl.
| | | |
|---|---|---|
| C07K 14/705 | (2006.01) | |
| A61K 38/17 | (2006.01) | |
| A61K 39/395 | (2006.01) | |
| C07K 14/435 | (2006.01) | |
| C07K 16/18 | (2006.01) | |
| A61K 39/00 | (2006.01) | |
| A61K 38/00 | (2006.01) | |

(52) U.S. Cl.
CPC ...... *A61K 39/39533* (2013.01); *C07K 14/435* (2013.01); *C07K 14/70503* (2013.01); *C07K 16/18* (2013.01); *A61K 38/00* (2013.01); *A61K 39/00* (2013.01); *C07K 2317/52* (2013.01); *C07K 2319/30* (2013.01); *C07K 2319/32* (2013.01)

(58) Field of Classification Search
None
See application file for complete search history.

(56) References Cited

U.S. PATENT DOCUMENTS

| | | | |
|---|---|---|---|
| 6,426,186 B1 | 7/2002 | Jones et al. | |
| 2002/0107363 A1 | 8/2002 | Fox et al. | |
| 2002/0165347 A1 | 11/2002 | Fox et al. | |
| 2002/0198143 A1 | 12/2002 | Ruben et al. | |
| 2004/0137577 A1 | 7/2004 | Coyle et al. | |
| 2004/0152105 A1* | 8/2004 | Vogt ................ | C07K 14/70532 435/6.16 |

FOREIGN PATENT DOCUMENTS

| | | |
|---|---|---|
| WO | 1998/019706 A1 | 5/1998 |
| WO | 2000/061755 A1 | 10/2000 |
| WO | 2001/036432 A2 | 5/2001 |
| WO | 2002/010187 A1 | 2/2002 |
| WO | 2002/079474 A2 | 10/2002 |
| WO | 2004/022594 A3 | 3/2004 |
| WO | WO 2004/022594 A2 | 3/2004 |
| WO | WO 2004/058986 A2 | 7/2004 |

OTHER PUBLICATIONS

Abeler-Dorner et al., "Butyrophilins: an emerging family of immune regulators," *Trends in Immunol* 33 (1):34-4 1, 2012.
Arnett et al., "Cosignaling Complexity Gels More Convoluted: The Emerging Importance of the B7-Like Butyrophilin Family of Immune Regulators," *Current Immunol Rev* 4 (I) 4 3-52, 2008.
Arnett et al., "Regulation of costimulation in the era butyrophilins," *Cytokine* 46: 370-375, 2009.
Arnett and Viney, "Immune modulation by butyrophilins," *Nature Reviews/Immunology* 14:559-569, 2014.
Clark et al., NCBI Reference Sequence, GenBank accession No. NM_152547, Version NM_152547.4 Aug. 25, 2016.
Cubillos-Ruiz and Conejo-Garcia, "It never rains but it pours, Potential role of butyrophilins in inhibiting anti-tumor immune responses," *Cell Cycle* 10 (3):368-369, 2011.
Database EMBL 'Online!, *Homo sapiens* cDNA FLJ32535 fis, clone SMINT2000277, weakly similar to Butyropholin Precursor, Database accession No. AK057097, Version AK057097.1 Jan. 9, 2008, abstract.
Database Genbank 'Online!, *Homo sapiens* similar to butyrophilin, subfamily 3, member A3; butyrophilin 3 (LOC153579), mRNA, Database accession No. XM_087714, Version XM_087714.1 Aug. 1, 2002, abstract.
Dong and Chen, "B7-H1 pathway and its role in the evasion of tumor immunity," *J Mol Med* 81:281-287, 2003.
Fahrer et al., A genomic view of immunology, Nature, Feb. 2001, 409:6822, 836-838 and Supplementary Information for Fahrer et al. A genomic view of immunology.
Gao el al., "Stimulating PD-I-Negative Signals Concurrent With Blocking CD 154 Co-Stimulation Induces Long-Term Islet Allograft Survival," *Transplantation* 76 (6):994-999, 2003.
Greenwald el al., "The B7 Family Revisited," *Ann Rev Immunol* 23:515-548, 2005.
Henry et al., Structure and evolution of the extended B7 family, Immunology Today, Elsevier Publications, Jun. 1999, 20:6, 285-288.
Koczor et al., "Detection of differentially methylated gene promoters in failing and nonfailing human left ventricle myocardium using computation analysis," *Physiol Genomics* 45:597-605, 2013.
Langnaese et al., Cloning of Z39Ig, a novel gene with immunoglobulin-like domains located on human chromosome X, Biochimica et Biophysica Acta, Jul. 24, 2000, 1492:2-3; 522-525.
Stefferl et al., Butyrophilin, a milk protein, modulates the encephalitogenic T cell response to myelin oligodendrocyte glycoprotein in experimental autoimmune encephalomyelitis, Journal of Immunology, Williams & Wilkins Co., Sep. 1, 2000, 165:5, 2859-2865.

(Continued)

*Primary Examiner* — Ilia I Ouspenski
(74) *Attorney, Agent, or Firm* — Lawrence B. Kong

(57) ABSTRACT

The invention provides novel BTNL9 proteins, including multimers, fragments, and variants of a human BTNL9 protein. In addition, antibodies that can bind to BTNL9 proteins and nucleic acids encoding BTNL9 proteins are provided. Uses for BTNL9 proteins, and agonists or antagonists thereof, are described.

9 Claims, 14 Drawing Sheets

Specification includes a Sequence Listing.

(56) References Cited

OTHER PUBLICATIONS

Viney, "Regulation of T cell activation by the B7-related butyrophilins," Presentation, Toronto 2011.
Watson et al., "Differential Effects of Costimulatory Pathway Modulation on Corneal Allograph Survival," *Investigative Ophthalmology & Visual Science* 47 (8):3417-3422, 2006.
Yamazaki et al., "A Butyrophilin Family Member Critically Inhibits T Cell Activation, " *J Immunol* 185:1-8, 2010.

* cited by examiner

SEQUENCE LISTING

<160> NUMBER OF SEQ ID NOS: 26

<210> SEQ ID NO 1
<211> LENGTH: 3520
<212> TYPE: DNA
<213> ORGANISM: Homo sapiens
<220> FEATURE:
<221> NAME/KEY: CDS
<222> LOCATION: (232)..(1836)

<400> SEQUENCE: 1

```
agagcaaacg gcatatatct tagggtggaa gatggataaa taattctgtc acacgtgccc      60
tggcctctgg agctcagctg ccagtccacg tctagggaat cttagcatct gggaccaaga     120
cactttacag caatcatcac cctttgcaga ggaggtgagc tcaccaggac tcatctgcca     180
tttcagacct tttgctgcta cctgccaggt ggcccccact gctgacgaga g atg gtg      237
                                                         Met Val
                                                           1 gac ctc tca gtc tcc cca gac tcc ttg aag cca gta tcg ctg acc agc       285
Asp Leu Ser Val Ser Pro Asp Ser Leu Lys Pro Val Ser Leu Thr Ser
        5                  10                  15 agt ctt gtc ttc ctc atg cac ctc ctc ctc ctt cag cct ggg gag ccg       333
Ser Leu Val Phe Leu Met His Leu Leu Leu Leu Gln Pro Gly Glu Pro
    20                  25                  30 agc tca gag gtc aag gtg cta ggc cct gag tat ccc atc ctg gcc ctc       381
Ser Ser Glu Val Lys Val Leu Gly Pro Glu Tyr Pro Ile Leu Ala Leu
35                  40                  45                  50 gtc ggg gag gag gtg gag ttc ccg tgc cac cta tgg cca cag ctg gat       429
Val Gly Glu Glu Val Glu Phe Pro Cys His Leu Trp Pro Gln Leu Asp
                55                  60                  65 gcc cag caa atg gag atc cgc tgg ttc cgg agt cag acc ttc aat gtg       477
Ala Gln Gln Met Glu Ile Arg Trp Phe Arg Ser Gln Thr Phe Asn Val
            70                  75                  80 gta cac ctg tac cag gag cag cag gag ctc cct ggc agg cag atg ccg       525
Val His Leu Tyr Gln Glu Gln Gln Glu Leu Pro Gly Arg Gln Met Pro
        85                  90                  95 gcg ttc cgg aac agg acc aag ttg gtc aag gac gac atc gcc tat ggc       573
Ala Phe Arg Asn Arg Thr Lys Leu Val Lys Asp Asp Ile Ala Tyr Gly
    100                 105                 110 agc gtg gtc ctg cag ctt cac agc atc atc ccc tct gac aag ggc aca       621
Ser Val Val Leu Gln Leu His Ser Ile Ile Pro Ser Asp Lys Gly Thr
```

```
                                              -continued 115                 120                 125                 130
tat ggc tgc cgc ttc cac tcc gac aac ttc tct ggc gaa gct ctc tgg        669
Tyr Gly Cys Arg Phe His Ser Asp Asn Phe Ser Gly Glu Ala Leu Trp
                    135                 140                 145 gaa ctg gag gta gca ggg ctg ggc tca gac cct cac ctc tcc ctt gag        717
Glu Leu Glu Val Ala Gly Leu Gly Ser Asp Pro His Leu Ser Leu Glu
            150                 155                 160 ggc ttc aag gaa gga ggc att cag ctg agg ctc aga tcc agt ggc tgg        765
Gly Phe Lys Glu Gly Gly Ile Gln Leu Arg Leu Arg Ser Ser Gly Trp
        165                 170                 175 tac ccc aag cct aag gtt cag tgg aga gac cac cag gga cag tgc ctg        813
Tyr Pro Lys Pro Lys Val Gln Trp Arg Asp His Gln Gly Gln Cys Leu
    180                 185                 190 cct cca gag ttt gaa gcc atc gtc tgg gat gcc cag gac ctg ttc agt        861
Pro Pro Glu Phe Glu Ala Ile Val Trp Asp Ala Gln Asp Leu Phe Ser
195                 200                 205                 210 ctg gaa aca tct gtg gtt gtc cga gcg gga gcc ctc agc aat gtg tcc        909
Leu Glu Thr Ser Val Val Val Arg Ala Gly Ala Leu Ser Asn Val Ser
                215                 220                 225 gtc tcc atc cag aat ctc ctc ttg agc cag aag aaa gag ttg gtg gtc        957
Val Ser Ile Gln Asn Leu Leu Leu Ser Gln Lys Lys Glu Leu Val Val
            230                 235                 240 cag ata gca gac gtg ttc gta ccc gga gcc tct gcg tgg aag agc gcg       1005
Gln Ile Ala Asp Val Phe Val Pro Gly Ala Ser Ala Trp Lys Ser Ala
        245                 250                 255 ttc gtc gcg acc ctg ccg ctg ctg ttg gtc ctc gcg gcg ctg gcg ctg       1053
Phe Val Ala Thr Leu Pro Leu Leu Leu Val Leu Ala Ala Leu Ala Leu
    260                 265                 270 ggc gtc ctc cgg aag cag cgg aga agc cga gaa aag ctg agg aag cag       1101
Gly Val Leu Arg Lys Gln Arg Arg Ser Arg Glu Lys Leu Arg Lys Gln
275                 280                 285                 290 gcg gag aag aga caa gag aaa ctc act gca gag ctg gaa aag ctt cag       1149
Ala Glu Lys Arg Gln Glu Lys Leu Thr Ala Glu Leu Glu Lys Leu Gln
                295                 300                 305 aca gag ctt gac tgg aga cgg gct gaa ggc cag gct gag tgg aga gca       1197
Thr Glu Leu Asp Trp Arg Arg Ala Glu Gly Gln Ala Glu Trp Arg Ala
            310                 315                 320 gcc caa aaa tat gca gtg gat gtg acg ctg gac ccg gcc tcg gcg cac       1245
Ala Gln Lys Tyr Ala Val Asp Val Thr Leu Asp Pro Ala Ser Ala His
        325                 330                 335 ccc agc ctg gag gtg tcg gag gat ggc aag agc gtg tct tcc cgc ggg       1293
Pro Ser Leu Glu Val Ser Glu Asp Gly Lys Ser Val Ser Ser Arg Gly
    340                 345                 350 gcg ccg cca ggc ccg gcg cct ggc cac ccg cag cgg ttc tcg gag cag       1341
Ala Pro Pro Gly Pro Ala Pro Gly His Pro Gln Arg Phe Ser Glu Gln
355                 360                 365                 370 acg tgc gcg ctg agc ctg gag cgg ttc tcc gcc ggc cgc cac tac tgg       1389
Thr Cys Ala Leu Ser Leu Glu Arg Phe Ser Ala Gly Arg His Tyr Trp
                375                 380                 385 gag gtg cac gtg ggc cgc cgc agc cgc tgg ttc ctg ggc gcc tgc ctg       1437
Glu Val His Val Gly Arg Arg Ser Arg Trp Phe Leu Gly Ala Cys Leu
            390                 395                 400 gcc gcg gtg ccg cgc gcg ggg cct gcg cgc ctg agc cct gcg gcc ggc       1485
Ala Ala Val Pro Arg Ala Gly Pro Ala Arg Leu Ser Pro Ala Ala Gly
        405                 410                 415 tac tgg gtg ctg ggg ctg tgg aac ggc tgc gag tac ttc gtc ctg gcc       1533
Tyr Trp Val Leu Gly Leu Trp Asn Gly Cys Glu Tyr Phe Val Leu Ala
    420                 425                 430 ccg cac cgc gtc gcg ctc acc ctg cgc gtg ccc ccg cgg cgc ctg ggc       1581
Pro His Arg Val Ala Leu Thr Leu Arg Val Pro Pro Arg Arg Leu Gly
```

```
Pro His Arg Val Ala Leu Thr Leu Arg Val Pro Arg Arg Leu Gly
435                 440                 445                 450
gtc ttc ctg gac tac gag gcc gga gag ctg tcc ttc ttc aac gtg tcc      1629
Val Phe Leu Asp Tyr Glu Ala Gly Glu Leu Ser Phe Phe Asn Val Ser
                        455                 460                 465
gac ggc tcc cac atc ttc acc ttc cac gac acc ttc tcg ggc gcg ctc      1677
Asp Gly Ser His Ile Phe Thr Phe His Asp Thr Phe Ser Gly Ala Leu
                470                 475                 480
tgt gcg tac ttc agg ccc agg gcc cac gac ggc ggc gaa cat ccg gat      1725
Cys Ala Tyr Phe Arg Pro Arg Ala His Asp Gly Gly Glu His Pro Asp
            485                 490                 495
ccc ctg acc atc tgc ccg ctg ccg gtt aga ggg acg ggc gtc ccc gaa      1773
Pro Leu Thr Ile Cys Pro Leu Pro Val Arg Gly Thr Gly Val Pro Glu
        500                 505                 510
gag aac gac agt gac acc tgg cta cag ccc tat gag ccc gcg gac ccc      1821
Glu Asn Asp Ser Asp Thr Trp Leu Gln Pro Tyr Glu Pro Ala Asp Pro
515                 520                 525                 530
gcc ctg gac tgg tgg tgaggcgccc tcgtggccgc gggactggcc ccggggggcc      1876
Ala Leu Asp Trp Trp
                535
cctggatcc caggccagcg ctttgctctc ctgctccgtc tgaagggagc aggtgcacca     1936
gccaaaatgt cagcgagggg gacaaagaga gggacctttg cctacgtaga tgtgtatgtg    1996
tagtgcgatt tcttcaagg aaaggagaca agtccaaagc tcgtttgtgg attgtgggac    2056
tgagcgaagg agtacaaata tatccacgtc gctcagagct ggggtgctca cggtgggcgg    2116
tgggcaagaa gccagcatgg aagaaagaag ggagaaaact ttggtgactg ccttagaggg    2176
atcagttaat ttgtatagtt ttatatttt tgtatatgtt tgctagctct aaaaaggtcg    2236
agatgcaata acacttcgta agcaacgagt tcacctaagt aaggctcaga tcctagtttt    2296
aaaaaccatt tcccattaaa atgaagttgg aggaacagct gcttctggag ccggggcaaa    2356
aatttcaagg tgagcctgga gcattgtgtg tggtgaagta aaataaaggc tcaaaacgtg    2416
acggcaaccc ggcaaaaggg tagggagcca ggccgaaggg gcctcactga ccaattgtgg    2476
gacaatttga acatcaggat gaataatgac aggagagatt ataacacact gaataaaaac    2536
ataatccatg agttcatgct gatactcaaa tttcttttta aaaggagaa acaggaaggt    2596
ttcttttgga ggtgaaatct aattattggt gagagtcttg gagaacaggc tgtttccagt    2656
ctcaaagcag taaccttata cactactat aagtttgaaa ggggaaaggt taccttaca    2716
atggagacat ctaccagatc atccaagtga ttaaatttaa catcatcaat gatgggacca    2776
aggacattat tagtttgaca actggggaaa gaagtgttct tcaccccta cccccaagac    2836
attgtctctg tcggccaggc tggagtgcag cctcaacctc ctgggtccaa gtgatcctcc    2896
cacctcagca cacaacacca tgcccaattt taagtgcgtt atagagacgg gggtctcact    2956
ttgttaccca ggctggtctc aaactcctgc gctcaagcaa tcctcccacc tgggcctccc    3016
aaaatgctgg gtgtacaggc atgagccgct gtgcctggct tcattttcag agtgagacat    3076
ttgtactgtg gctatgtagg agaacattct tgttcttagc aaacatactg aagttttag    3136
atattaatta ccacagtgtc tgccactgaa tttccagtga ctaagtggaa aaatataaaa    3196
catatgaata taaagaaaga aagagacaag tcaaatgtag taaaatgaca acacttggtg    3256
actctaggtg actggtcgac agatgttcat tgtactatca atgtggcttt gctgtgggtt    3316
tgaaattttg caaactaaga gttgggtggc ggggagaagg atacaccaaa aaactaagtg    3376
attatctttg gatgggaaaa tgtttggtaa ttgcattctt aaaatgtctt ctttgtattt    3436
```

-continued

```
tttaatgttc aataatgtat atgtatcagt tctgtaataa aggggaaaac actttttta    3496 aataaaaaaa aaaaaaaaaa aaaa                                           3520
```

<210> SEQ ID NO 2
<211> LENGTH: 535
<212> TYPE: PRT
<213> ORGANISM: Homo sapiens

<400> SEQUENCE: 2

```
Met Val Asp Leu Ser Val Ser Pro Asp Ser Leu Lys Pro Val Ser Leu
1               5                   10                  15

Thr Ser Ser Leu Val Phe Leu Met His Leu Leu Leu Gln Pro Gly
            20                  25                  30

Glu Pro Ser Ser Glu Val Lys Val Leu Gly Pro Glu Tyr Pro Ile Leu
        35                  40                  45

Ala Leu Val Gly Glu Val Glu Phe Pro Cys His Leu Trp Pro Gln
    50                  55                  60

Leu Asp Ala Gln Gln Met Glu Ile Arg Trp Phe Arg Ser Gln Thr Phe
65                  70                  75                  80

Asn Val Val His Leu Tyr Gln Glu Gln Gln Glu Leu Pro Gly Arg Gln
                85                  90                  95

Met Pro Ala Phe Arg Asn Arg Thr Lys Leu Val Lys Asp Asp Ile Ala
            100                 105                 110

Tyr Gly Ser Val Val Leu Gln Leu His Ser Ile Ile Pro Ser Asp Lys
        115                 120                 125

Gly Thr Tyr Gly Cys Arg Phe His Ser Asp Asn Phe Ser Gly Glu Ala
    130                 135                 140

Leu Trp Glu Leu Glu Val Ala Gly Leu Gly Ser Asp Pro His Leu Ser
145                 150                 155                 160

Leu Glu Gly Phe Lys Glu Gly Gly Ile Gln Leu Arg Leu Arg Ser Ser
                165                 170                 175

Gly Trp Tyr Pro Lys Pro Lys Val Gln Trp Arg Asp His Gln Gly Gln
            180                 185                 190

Cys Leu Pro Pro Glu Phe Glu Ala Ile Val Trp Asp Ala Gln Asp Leu
        195                 200                 205

Phe Ser Leu Glu Thr Ser Val Val Arg Ala Gly Ala Leu Ser Asn
    210                 215                 220

Val Ser Val Ser Ile Gln Asn Leu Leu Leu Ser Gln Lys Lys Glu Leu
225                 230                 235                 240

Val Val Gln Ile Ala Asp Val Phe Val Pro Gly Ala Ser Ala Trp Lys
                245                 250                 255

Ser Ala Phe Val Ala Thr Leu Pro Leu Leu Leu Val Leu Ala Ala Leu
            260                 265                 270

Ala Leu Gly Val Leu Arg Lys Gln Arg Arg Ser Arg Glu Lys Leu Arg
        275                 280                 285

Lys Gln Ala Glu Lys Arg Gln Glu Lys Leu Thr Ala Glu Leu Glu Lys
    290                 295                 300

Leu Gln Thr Glu Leu Asp Trp Arg Arg Ala Glu Gly Gln Ala Glu Trp
305                 310                 315                 320

Arg Ala Ala Gln Lys Tyr Ala Val Asp Val Thr Leu Asp Pro Ala Ser
                325                 330                 335

Ala His Pro Ser Leu Glu Val Ser Glu Asp Gly Lys Ser Val Ser Ser
            340                 345                 350

Arg Gly Ala Pro Pro Gly Pro Ala Pro Gly His Pro Gln Arg Phe Ser
```

```
                    355                 360                 365
Glu Gln Thr Cys Ala Leu Ser Leu Glu Arg Phe Ser Ala Gly Arg His
    370                 375                 380
Tyr Trp Glu Val His Val Gly Arg Arg Ser Arg Trp Phe Leu Gly Ala
385                 390                 395                 400
Cys Leu Ala Ala Val Pro Arg Ala Gly Pro Ala Arg Leu Ser Pro Ala
                405                 410                 415
Ala Gly Tyr Trp Val Leu Gly Leu Trp Asn Gly Cys Glu Tyr Phe Val
            420                 425                 430
Leu Ala Pro His Arg Val Ala Leu Thr Leu Arg Val Pro Pro Arg Arg
        435                 440                 445
Leu Gly Val Phe Leu Asp Tyr Glu Ala Gly Glu Leu Ser Phe Phe Asn
    450                 455                 460
Val Ser Asp Gly Ser His Ile Phe Thr Phe His Asp Thr Phe Ser Gly
465                 470                 475                 480
Ala Leu Cys Ala Tyr Phe Arg Pro Arg Ala His Asp Gly Gly Glu His
                485                 490                 495
Pro Asp Pro Leu Thr Ile Cys Pro Leu Pro Val Arg Gly Thr Gly Val
            500                 505                 510
Pro Glu Glu Asn Asp Ser Asp Thr Trp Leu Gln Pro Tyr Glu Pro Ala
        515                 520                 525
Asp Pro Ala Leu Asp Trp Trp
    530                 535

<210> SEQ ID NO 3
<211> LENGTH: 20
<212> TYPE: PRT
<213> ORGANISM: Homo sapiens

<400> SEQUENCE: 3

Met Glu Thr Asp Thr Leu Leu Leu Trp Val Leu Leu Leu Trp Val Pro
1               5                   10                  15
Gly Ser Thr Gly
            20

<210> SEQ ID NO 4
<211> LENGTH: 26
<212> TYPE: PRT
<213> ORGANISM: Homo sapiens

<400> SEQUENCE: 4

Met Ala Thr Gly Ser Arg Thr Ser Leu Leu Leu Ala Phe Gly Leu Leu
1               5                   10                  15
Cys Leu Pro Trp Leu Gln Glu Gly Ser Ala
            20                  25

<210> SEQ ID NO 5
<211> LENGTH: 2463
<212> TYPE: DNA
<213> ORGANISM: Mus sp
<220> FEATURE:
<221> NAME/KEY: CDS
<222> LOCATION: (124)..(1731)

<400> SEQUENCE: 5
agcttagcat cagggactaa catttcacaa tcaccccctt tagagggagg tgagattgcc      60
agcatccctc taccgcttgg atcttcttct gttacctgaa aggtgggccc tcaccgctga    120 cag atg gca gat ttc tca gta ttt ctg ggg ttt ctg aag caa ata cct      168
```

```
        Met Ala Asp Phe Ser Val Phe Leu Gly Phe Leu Lys Gln Ile Pro
        1               5                  10                  15 cgg tgc ctc agc atc ttc ttc acc tac ctt ctc ttc ctt cag ttg tgg        216
Arg Cys Leu Ser Ile Phe Phe Thr Tyr Leu Leu Phe Leu Gln Leu Trp
                    20                  25                  30 gag gtg aac tca gac aag gtc tgg gtg ttg ggc cct gag gag tcc att        264
Glu Val Asn Ser Asp Lys Val Trp Val Leu Gly Pro Glu Glu Ser Ile
                35                  40                  45 ttg gcc cgc gtc ggg gaa gcg gtg gag ttc cca tgt cgc tta tca tca        312
Leu Ala Arg Val Gly Glu Ala Val Glu Phe Pro Cys Arg Leu Ser Ser
            50                  55                  60 tac caa gac gca gag cac atg gaa att cgc tgg ttt cgg gcc cag gtc        360
Tyr Gln Asp Ala Glu His Met Glu Ile Arg Trp Phe Arg Ala Gln Val
65                  70                  75 tcc aac gtg gta tac ctg tac cag gag ccg cag ggg cgc tcc agc ctg        408
Ser Asn Val Val Tyr Leu Tyr Gln Glu Pro Gln Gly Arg Ser Ser Leu
80                  85                  90                  95 cag atg gca cag ttc cga aac agg acc tta ttt gaa gcc tat gac att        456
Gln Met Ala Gln Phe Arg Asn Arg Thr Leu Phe Glu Ala Tyr Asp Ile
                100                 105                 110 gca gag gga agc gtg aac cta cac atc ctt aaa gtg ctt ccc tcc gac        504
Ala Glu Gly Ser Val Asn Leu His Ile Leu Lys Val Leu Pro Ser Asp
            115                 120                 125 gag ggc cga tat ggg tgc cgc ttt ctt tct gac aac ttc tct ggt gaa        552
Glu Gly Arg Tyr Gly Cys Arg Phe Leu Ser Asp Asn Phe Ser Gly Glu
        130                 135                 140 gcc acg tgg gag ctg gaa gta gca gga tcg ggc tca gac cca cac atc        600
Ala Thr Trp Glu Leu Glu Val Ala Gly Ser Gly Ser Asp Pro His Ile
145                 150                 155 tcc ctc cag ggc ttc agt gga gaa ggt att cag ctg cag tgc agt tcc        648
Ser Leu Gln Gly Phe Ser Gly Glu Gly Ile Gln Leu Gln Cys Ser Ser
160                 165                 170                 175 agt ggc tgg tac ccc aag cca aag gtt cag tgg aga ggt cac cag ggt        696
Ser Gly Trp Tyr Pro Lys Pro Lys Val Gln Trp Arg Gly His Gln Gly
                180                 185                 190 cag tgc ctt tct cca gag tct gaa gcc atc acc cag aat gcc caa ggc        744
Gln Cys Leu Ser Pro Glu Ser Glu Ala Ile Thr Gln Asn Ala Gln Gly
            195                 200                 205 ctg ttc agt ctg gag aca tcc gtg att gtc cga gga gga gcc cat agc        792
Leu Phe Ser Leu Glu Thr Ser Val Ile Val Arg Gly Gly Ala His Ser
        210                 215                 220 aat gtg tct tgt ata atc cag aac ccc ttg ctg ccc cag aag aaa gaa        840
Asn Val Ser Cys Ile Ile Gln Asn Pro Leu Leu Pro Gln Lys Lys Glu
225                 230                 235 ttc gtg atc cag att gca gat gtg ttc cta ccc aga atg tcc ccc tgg        888
Phe Val Ile Gln Ile Ala Asp Val Phe Leu Pro Arg Met Ser Pro Trp
240                 245                 250                 255 aag aaa gcg ttt gtg gga acc ctg gtg gtc ctg ccg ctc agt ctg att        936
Lys Lys Ala Phe Val Gly Thr Leu Val Val Leu Pro Leu Ser Leu Ile
                260                 265                 270 gtg ctc acc atg ctg gcg ctg cga tat ttt tac aag ctg cgg agc ttc        984
Val Leu Thr Met Leu Ala Leu Arg Tyr Phe Tyr Lys Leu Arg Ser Phe
            275                 280                 285 caa gaa aaa cag gtg aag cag gga gag gag gtc cga gag aaa ctt cag       1032
Gln Glu Lys Gln Val Lys Gln Gly Glu Glu Val Arg Glu Lys Leu Gln
        290                 295                 300 aca gag ctt gac tgg aga agg tct gaa ggc cag gct gag tgg aga gca       1080
Thr Glu Leu Asp Trp Arg Arg Ser Glu Gly Gln Ala Glu Trp Arg Ala
305                 310                 315
```

```
gcc cag caa tat gca gcg gat gtg acc ttg gat cct gcc aca gcg cac    1128
Ala Gln Gln Tyr Ala Ala Asp Val Thr Leu Asp Pro Ala Thr Ala His
320             325                 330                 335 cct agc ctg gag gtc tcc aac aac ggc aag acc gtg tcc tcc cgc ctg    1176
Pro Ser Leu Glu Val Ser Asn Asn Gly Lys Thr Val Ser Ser Arg Leu
                340                 345                 350 ggg gtg ccc agt att gca gct ggg gac ccg cag cgg ttc tcg gag cag    1224
Gly Val Pro Ser Ile Ala Ala Gly Asp Pro Gln Arg Phe Ser Glu Gln
            355                 360                 365 acc tgc gtg ctg agc cgg gag cgc ttc tcc agc ggc cgc cac tac tgg    1272
Thr Cys Val Leu Ser Arg Glu Arg Phe Ser Ser Gly Arg His Tyr Trp
        370                 375                 380 gag gtg cac gtg ggc cgg cgc agc cgc tgg ttc ctg ggc gcc tgt ctg    1320
Glu Val His Val Gly Arg Arg Ser Arg Trp Phe Leu Gly Ala Cys Leu
    385                 390                 395 gag tcg gtg gag cgc tcc ggg ccc gcg cgc ctg agc ccg gcg gct ggc    1368
Glu Ser Val Glu Arg Ser Gly Pro Ala Arg Leu Ser Pro Ala Ala Gly
400                 405                 410                 415 tac tgg gtg atg ggg ctg tgg aac cgc tgc gag tac ttc gtg ctg gac    1416
Tyr Trp Val Met Gly Leu Trp Asn Arg Cys Glu Tyr Phe Val Leu Asp
                420                 425                 430 ccg cat cgc gtg gca ctg gcg cta cgc gtg cct ccc cgg agg ata ggc    1464
Pro His Arg Val Ala Leu Ala Leu Arg Val Pro Pro Arg Arg Ile Gly
            435                 440                 445 gtc ctg ttg gac tac gag gcc ggg aag ctg tct ttc ttc aac gtg tct    1512
Val Leu Leu Asp Tyr Glu Ala Gly Lys Leu Ser Phe Phe Asn Val Ser
        450                 455                 460 gat ggc tcg cac atc ttc agc ttc acc gac act ttc tca ggg gcg ctc    1560
Asp Gly Ser His Ile Phe Ser Phe Thr Asp Thr Phe Ser Gly Ala Leu
    465                 470                 475 cgc gcc tac tta agg ccc cga gct cac gac ggc agt gaa cat ccg gat    1608
Arg Ala Tyr Leu Arg Pro Arg Ala His Asp Gly Ser Glu His Pro Asp
480                 485                 490                 495 cct atg acc atc tgc tct ttg ccg gtt aga ggg cca cag gtc ctc gaa    1656
Pro Met Thr Ile Cys Ser Leu Pro Val Arg Gly Pro Gln Val Leu Glu
                500                 505                 510 gag aac gac aac gac aac tgg cta cag ccc tat gag cct ctg gac ccc    1704
Glu Asn Asp Asn Asp Asn Trp Leu Gln Pro Tyr Glu Pro Leu Asp Pro
            515                 520                 525 gcc tgg gct gtt aat gag gca gtg tcc tgacctcaag gccaggtcca          1751
Ala Trp Ala Val Asn Glu Ala Val Ser
        530                 535 agcactgtcc tgaactcctg dacagcgctt tgctctcctg cagccaaagc agagtcagca  1811
gaaagaggac agagagagag ggcctataca gatgaatgta taaattatc tttaaacaga   1871 caaatgaaag attgtttgtg tatatagcag gattctggag tgtgcagtgt agaagatggg  1931
aaagaatcat aattatccgc taatgtgtgt atagttctgt atagtgtata tgtgtgtgtg  1991
tgtgtgtgtg tgtgtgtgtg tgtaattttg tggatcctgc aaaagtctag aagtaatgtc  2051
atttcataag caatgagttc accttggct cagaatacag tttatagcga cttccttgat   2111
catgtatgtg gcaattcgaa catgaaattc aataatggca gtgatgtggc tggctggggg  2171
taagcagtgg tagagtgctt gcctagcccg agggatagca cacatcttca acttcactgc  2231
cgatttcccc agaaaagtgc attggatccc ccgctcaggt ggagcaggat aaggatggca  2291
ggaatgcagc gatactccta aaacataaac atacatataa gtaacattta caaacagaaa  2351
aggctatatt tagcaaaata taagtatata catatactca tctaatatca ttaattttaa  2411
aagccatgat tttgaaagag agctagaagt gaggcatagg agaatttgag gg          2463
```

<210> SEQ ID NO 6
<211> LENGTH: 536
<212> TYPE: PRT
<213> ORGANISM: Mus sp

<400> SEQUENCE: 6

```
Met Ala Asp Phe Ser Val Phe Leu Gly Phe Leu Lys Gln Ile Pro Arg
1               5                   10                  15

Cys Leu Ser Ile Phe Phe Thr Tyr Leu Leu Phe Leu Gln Leu Trp Glu
            20                  25                  30

Val Asn Ser Asp Lys Val Trp Val Leu Gly Pro Glu Glu Ser Ile Leu
        35                  40                  45

Ala Arg Val Gly Glu Ala Val Glu Phe Pro Cys Arg Leu Ser Ser Tyr
    50                  55                  60

Gln Asp Ala Glu His Met Glu Ile Arg Trp Phe Arg Ala Gln Val Ser
65                  70                  75                  80

Asn Val Val Tyr Leu Tyr Gln Glu Pro Gln Gly Arg Ser Ser Leu Gln
                85                  90                  95

Met Ala Gln Phe Arg Asn Arg Thr Leu Phe Glu Ala Tyr Asp Ile Ala
            100                 105                 110

Glu Gly Ser Val Asn Leu His Ile Leu Lys Val Leu Pro Ser Asp Glu
        115                 120                 125

Gly Arg Tyr Gly Cys Arg Phe Leu Ser Asp Asn Phe Ser Gly Glu Ala
    130                 135                 140

Thr Trp Glu Leu Glu Val Ala Gly Ser Gly Ser Asp Pro His Ile Ser
145                 150                 155                 160

Leu Gln Gly Phe Ser Gly Glu Gly Ile Gln Leu Gln Cys Ser Ser Ser
                165                 170                 175

Gly Trp Tyr Pro Lys Pro Lys Val Gln Trp Arg Gly His Gln Gly Gln
            180                 185                 190

Cys Leu Ser Pro Glu Ser Glu Ala Ile Thr Gln Asn Ala Gln Gly Leu
        195                 200                 205

Phe Ser Leu Glu Thr Ser Val Ile Val Arg Gly Gly Ala His Ser Asn
    210                 215                 220

Val Ser Cys Ile Ile Gln Asn Pro Leu Leu Pro Gln Lys Lys Glu Phe
225                 230                 235                 240

Val Ile Gln Ile Ala Asp Val Phe Leu Pro Arg Met Ser Pro Trp Lys
                245                 250                 255

Lys Ala Phe Val Gly Thr Leu Val Leu Pro Leu Ser Leu Ile Val
            260                 265                 270

Leu Thr Met Leu Ala Leu Arg Tyr Phe Tyr Lys Leu Arg Ser Phe Gln
        275                 280                 285

Glu Lys Gln Val Lys Gln Gly Glu Glu Val Arg Glu Lys Leu Gln Thr
    290                 295                 300

Glu Leu Asp Trp Arg Arg Ser Glu Gly Gln Ala Glu Trp Arg Ala Ala
305                 310                 315                 320

Gln Gln Tyr Ala Ala Asp Val Thr Leu Asp Pro Ala Thr Ala His Pro
                325                 330                 335

Ser Leu Glu Val Ser Asn Asn Gly Lys Thr Val Ser Arg Leu Gly
            340                 345                 350

Val Pro Ser Ile Ala Ala Gly Asp Pro Gln Arg Phe Ser Glu Gln Thr
        355                 360                 365

Cys Val Leu Ser Arg Glu Arg Phe Ser Ser Gly Arg His Tyr Trp Glu
```

```
            370                 375                 380
Val His Val Gly Arg Arg Ser Arg Trp Phe Leu Gly Ala Cys Leu Glu
385                 390                 395                 400

Ser Val Glu Arg Ser Gly Pro Ala Arg Leu Ser Pro Ala Ala Gly Tyr
                405                 410                 415

Trp Val Met Gly Leu Trp Asn Arg Cys Glu Tyr Phe Val Leu Asp Pro
                420                 425                 430

His Arg Val Ala Leu Ala Leu Arg Val Pro Pro Arg Arg Ile Gly Val
            435                 440                 445

Leu Leu Asp Tyr Glu Ala Gly Lys Leu Ser Phe Phe Asn Val Ser Asp
        450                 455                 460

Gly Ser His Ile Phe Ser Phe Thr Asp Thr Phe Ser Gly Ala Leu Arg
465                 470                 475                 480

Ala Tyr Leu Arg Pro Arg Ala His Asp Gly Ser Glu His Pro Asp Pro
                485                 490                 495

Met Thr Ile Cys Ser Leu Pro Val Arg Gly Pro Gln Val Leu Glu Glu
            500                 505                 510

Asn Asp Asn Asp Asn Trp Leu Gln Pro Tyr Glu Pro Leu Asp Pro Ala
        515                 520                 525

Trp Ala Val Asn Glu Ala Val Ser
    530                 535

<210> SEQ ID NO 7
<211> LENGTH: 1505
<212> TYPE: DNA
<213> ORGANISM: Homo sapiens
<220> FEATURE:
<221> NAME/KEY: CDS
<222> LOCATION: (91)..(1122)

<400> SEQUENCE: 7
ctttgcagag gaggtgagct caccaggact catctgccat ttcagacctt ttgctgctac      60
ctgccaggtg gcccccactg ctgacgagag atg gtg gac ctc tca gtc tcc cca     114
                                  Met Val Asp Leu Ser Val Ser Pro
                                    1               5 gac tcc ttg aag cca gta tcg ctg acc agc agt ctt gtc ttc ctc atg     162
Asp Ser Leu Lys Pro Val Ser Leu Thr Ser Ser Leu Val Phe Leu Met
         10                  15                  20 cac ctc ctc ctc ctt cag cct ggg gag ccg agc tca gag gtc aag gtg     210
His Leu Leu Leu Leu Gln Pro Gly Glu Pro Ser Ser Glu Val Lys Val
 25                  30                  35                  40 cta ggc cct gag tat ccc atc ctg gcc ctc gtc ggg gag gag gtg gag     258
Leu Gly Pro Glu Tyr Pro Ile Leu Ala Leu Val Gly Glu Glu Val Glu
                 45                  50                  55 ttc ccg tgc cac cta tgg cca cag ctg gat gcc cag caa atg gag atc     306
Phe Pro Cys His Leu Trp Pro Gln Leu Asp Ala Gln Gln Met Glu Ile
             60                  65                  70 cgc tgg ttc cgg agt cag acc ttc aat gtg gta cac ctg tac cag gag     354
Arg Trp Phe Arg Ser Gln Thr Phe Asn Val Val His Leu Tyr Gln Glu
         75                  80                  85 cag cag gag ctc cct ggc agg cag atg ccg gcg ttc cgg aac agg acc     402
Gln Gln Glu Leu Pro Gly Arg Gln Met Pro Ala Phe Arg Asn Arg Thr
 90                  95                 100 aag ttg gtc aag gac gac atc gcc tat ggc agc gtg gtc ctg cag ctt     450
Lys Leu Val Lys Asp Asp Ile Ala Tyr Gly Ser Val Val Leu Gln Leu
105                 110                 115                 120 cac agc atc atc ccc tct gac aag ggc aca tat ggc tgc cgc ttc cac     498
His Ser Ile Ile Pro Ser Asp Lys Gly Thr Tyr Gly Cys Arg Phe His
```

|  |  |  |  |  |  |  |  |  |  |  |  |  |  |  |
|---|---|---|---|---|---|---|---|---|---|---|---|---|---|---|
|  |  |  | 125 |  |  |  | 130 |  |  |  | 135 |  |  |  |

```
tcc gac aac ttc tct ggc gaa gct ctc tgg gaa ctg gag gta gca ggg      546
Ser Asp Asn Phe Ser Gly Glu Ala Leu Trp Glu Leu Glu Val Ala Gly
        140                 145                 150 ctg ggc tca gac cct cac ctc tcc ctt gag ggc ttc aag gaa gga ggc      594
Leu Gly Ser Asp Pro His Leu Ser Leu Glu Gly Phe Lys Glu Gly Gly
155                 160                 165 att cag ctg agg ctc aga tcc agt ggc tgg tac ccc aag cct aag gtt      642
Ile Gln Leu Arg Leu Arg Ser Ser Gly Trp Tyr Pro Lys Pro Lys Val
        170                 175                 180 cag tgg aga gac cac cag gga cag tgc ctg cct cca gag ttt gaa gcc      690
Gln Trp Arg Asp His Gln Gly Gln Cys Leu Pro Pro Glu Phe Glu Ala
185                 190                 195                 200 atc gtc tgg gat gcc cag gac ctg ttc agt ctg gaa aca tct gtg gtt      738
Ile Val Trp Asp Ala Gln Asp Leu Phe Ser Leu Glu Thr Ser Val Val
        205                 210                 215 gtc cga gcg gga gcc ctc agc aat gtg tcc gtc tcc atc cag aat ctc      786
Val Arg Ala Gly Ala Leu Ser Asn Val Ser Val Ser Ile Gln Asn Leu
        220                 225                 230 ctc ttg agc cag aag aaa gag ttg gtg gtc cag ata gca gac gtg ttc      834
Leu Leu Ser Gln Lys Lys Glu Leu Val Val Gln Ile Ala Asp Val Phe
235                 240                 245 gta ccc gga gcc tct gcg tgg aag agc gcg ttc gtc gcg acc ctg ccg      882
Val Pro Gly Ala Ser Ala Trp Lys Ser Ala Phe Val Ala Thr Leu Pro
250                 255                 260 ctg ctg ttg gtc ctc gcg gcg ctg gcg ctg ggc gtc ctc cgg aag cag      930
Leu Leu Leu Val Leu Ala Ala Leu Ala Leu Gly Val Leu Arg Lys Gln
265                 270                 275                 280 cgg aga agc cga gaa aag ctg agg aag cag gcg gag aag aga caa gag      978
Arg Arg Ser Arg Glu Lys Leu Arg Lys Gln Ala Glu Lys Arg Gln Glu
            285                 290                 295 aaa ctc act gca gag ctg aaa aag ctt cag aca gag ctt gac tgg aga     1026
Lys Leu Thr Ala Glu Leu Glu Lys Leu Gln Thr Glu Leu Asp Trp Arg
        300                 305                 310 cgg gct gaa ggc cag gct gag tgc ttc gtt tta gcc agc cac cct cct     1074
Arg Ala Glu Gly Gln Ala Glu Cys Phe Val Leu Ala Ser His Pro Pro
        315                 320                 325 gga gaa ggt atc cag gct gcc tct aac tcc aca aca aca ctg aat gca     1122
Gly Glu Gly Ile Gln Ala Ala Ser Asn Ser Thr Thr Thr Leu Asn Ala
330                 335                 340 tagtctcaaa cgtgttgcct tacggcgctg tgtggagatt tctctggggt ttgcaacctc   1182
tgaatgctga gaagattgag catctctgta tatgctagtt ggctctgggg acttcctcta   1242
ctgaaaattg ccagctcaca tcactgaccc atttttctta tgggatggct gtcttttatt   1302
attaacagga atattatata tctgtgtgtg tgtgtgtgtg tgtgtgtgtg tgtgtgtgag   1362
attaatccct catgggtaaa catcgtgaat tccttcttct gttgtgccat ctgccattag   1422
ctttgtccat agttcccctt attgaaaagg aattattaat tttgataaaa cataatccat   1482 caaaaaaaa aaaaaaaaaa aaa                                           1505

<210> SEQ ID NO 8
<211> LENGTH: 344
<212> TYPE: PRT
<213> ORGANISM: Homo sapiens

<400> SEQUENCE: 8

Met Val Asp Leu Ser Val Ser Pro Asp Ser Leu Lys Pro Val Ser Leu
1               5                   10                  15
```

```
Thr Ser Ser Leu Val Phe Leu Met His Leu Leu Leu Gln Pro Gly
                20                  25                  30

Glu Pro Ser Ser Glu Val Lys Val Leu Gly Pro Glu Tyr Pro Ile Leu
            35                  40                  45

Ala Leu Val Gly Glu Glu Val Glu Phe Pro Cys His Leu Trp Pro Gln
 50                  55                  60

Leu Asp Ala Gln Gln Met Glu Ile Arg Trp Phe Arg Ser Gln Thr Phe
 65                  70                  75                  80

Asn Val Val His Leu Tyr Gln Glu Gln Gln Glu Leu Pro Gly Arg Gln
                85                  90                  95

Met Pro Ala Phe Arg Asn Arg Thr Lys Leu Val Lys Asp Asp Ile Ala
            100                 105                 110

Tyr Gly Ser Val Val Leu Gln Leu His Ser Ile Ile Pro Ser Asp Lys
        115                 120                 125

Gly Thr Tyr Gly Cys Arg Phe His Ser Asp Asn Phe Ser Gly Glu Ala
130                 135                 140

Leu Trp Glu Leu Glu Val Ala Gly Leu Gly Ser Asp Pro His Leu Ser
145                 150                 155                 160

Leu Glu Gly Phe Lys Glu Gly Gly Ile Gln Leu Arg Leu Arg Ser Ser
                165                 170                 175

Gly Trp Tyr Pro Lys Pro Lys Val Gln Trp Arg Asp His Gln Gly Gln
            180                 185                 190

Cys Leu Pro Pro Glu Phe Glu Ala Ile Val Trp Asp Ala Gln Asp Leu
        195                 200                 205

Phe Ser Leu Glu Thr Ser Val Val Val Arg Ala Gly Ala Leu Ser Asn
210                 215                 220

Val Ser Val Ser Ile Gln Asn Leu Leu Leu Ser Gln Lys Lys Glu Leu
225                 230                 235                 240

Val Val Gln Ile Ala Asp Val Phe Val Pro Gly Ala Ser Ala Trp Lys
                245                 250                 255

Ser Ala Phe Val Ala Thr Leu Pro Leu Leu Leu Val Leu Ala Ala Leu
            260                 265                 270

Ala Leu Gly Val Leu Arg Lys Gln Arg Arg Ser Arg Glu Lys Leu Arg
        275                 280                 285

Lys Gln Ala Glu Lys Arg Gln Glu Lys Leu Thr Ala Glu Leu Glu Lys
290                 295                 300

Leu Gln Thr Glu Leu Asp Trp Arg Arg Ala Glu Gly Gln Ala Glu Cys
305                 310                 315                 320

Phe Val Leu Ala Ser His Pro Pro Gly Glu Gly Ile Gln Ala Ala Ser
                325                 330                 335

Asn Ser Thr Thr Thr Leu Asn Ala
            340

<210> SEQ ID NO 9
<211> LENGTH: 5
<212> TYPE: PRT
<213> ORGANISM: Artificial
<220> FEATURE:
<223> OTHER INFORMATION: Linker

<400> SEQUENCE: 9

Gly Gly Gly Gly Ser
1               5

<210> SEQ ID NO 10
<211> LENGTH: 6
```

```
<212> TYPE: PRT
<213> ORGANISM: Artificial
<220> FEATURE:
<223> OTHER INFORMATION: Linker

<400> SEQUENCE: 10

Gly Gly Gly Gly Ser Asn
1               5

<210> SEQ ID NO 11
<211> LENGTH: 12
<212> TYPE: PRT
<213> ORGANISM: Artificial
<220> FEATURE:
<223> OTHER INFORMATION: Linker

<400> SEQUENCE: 11

Gly Lys Ser Ser Gly Ser Gly Ser Glu Ser Lys Ser
1               5                   10

<210> SEQ ID NO 12
<211> LENGTH: 14
<212> TYPE: PRT
<213> ORGANISM: Artificial
<220> FEATURE:
<223> OTHER INFORMATION: Linker

<400> SEQUENCE: 12

Gly Ser Thr Ser Gly Ser Gly Lys Ser Ser Glu Gly Lys Gly
1               5                   10

<210> SEQ ID NO 13
<211> LENGTH: 18
<212> TYPE: PRT
<213> ORGANISM: Artificial
<220> FEATURE:
<223> OTHER INFORMATION: Linker

<400> SEQUENCE: 13

Gly Ser Thr Ser Gly Ser Gly Lys Ser Ser Glu Gly Ser Gly Ser Thr
1               5                   10                  15

Lys Gly

<210> SEQ ID NO 14
<211> LENGTH: 14
<212> TYPE: PRT
<213> ORGANISM: Artificial
<220> FEATURE:
<223> OTHER INFORMATION: Linker

<400> SEQUENCE: 14

Gly Ser Thr Ser Gly Ser Gly Lys Ser Ser Glu Gly Lys Gly
1               5                   10

<210> SEQ ID NO 15
<211> LENGTH: 18
<212> TYPE: PRT
<213> ORGANISM: Artificial
<220> FEATURE:
<223> OTHER INFORMATION: Linker

<400> SEQUENCE: 15

Gly Ser Thr Ser Gly Ser Gly Lys Pro Gly Ser Gly Glu Gly Ser Thr
1               5                   10                  15

Lys Gly
```

<210> SEQ ID NO 16
<211> LENGTH: 14
<212> TYPE: PRT
<213> ORGANISM: Artificial
<220> FEATURE:
<223> OTHER INFORMATION: Linker

<400> SEQUENCE: 16

```
Glu Gly Lys Ser Ser Gly Ser Gly Ser Glu Ser Lys Glu Phe
1               5                   10
```

<210> SEQ ID NO 17
<211> LENGTH: 15
<212> TYPE: PRT
<213> ORGANISM: Artificial
<220> FEATURE:
<223> OTHER INFORMATION: Linker

<400> SEQUENCE: 17

```
Gly Gly Gly Gly Ser Gly Gly Gly Gly Ser Gly Gly Gly Gly Ser
1               5                   10                  15
```

<210> SEQ ID NO 18
<211> LENGTH: 1500
<212> TYPE: DNA
<213> ORGANISM: Artificial
<220> FEATURE:
<223> OTHER INFORMATION: Nucleotide sequence encoding a fusion protein
<220> FEATURE:
<221> NAME/KEY: CDS
<222> LOCATION: (1)..(1500)

<400> SEQUENCE: 18

```
atg gtg gac ctc tca gtc tcc cca gac tcc ttg aag cca gta tcg ctg        48
Met Val Asp Leu Ser Val Ser Pro Asp Ser Leu Lys Pro Val Ser Leu
1               5                   10                  15 acc agc agt ctt gtc ttc ctc atg cac ctc ctc ctc ttc cag cct ggg        96
Thr Ser Ser Leu Val Phe Leu Met His Leu Leu Leu Leu Gln Pro Gly
                20                  25                  30 gag ccg agc tca gag gtc aag gtg cta ggc cct gag tat ccc atc ctg       144
Glu Pro Ser Ser Glu Val Lys Val Leu Gly Pro Glu Tyr Pro Ile Leu
            35                  40                  45 gcc ctc gtc ggg gag gag gtg gag ttc cga tgc cac cta tgg cca cag       192
Ala Leu Val Gly Glu Glu Val Glu Phe Arg Cys His Leu Trp Pro Gln
        50                  55                  60 ctg gat gcc cag caa atg gag atc cgc tgg ttc cgg agt cag acc ttc       240
Leu Asp Ala Gln Gln Met Glu Ile Arg Trp Phe Arg Ser Gln Thr Phe
65                  70                  75                  80 aat gtg gta cac ctg tac cag gag cag cag gag ctc cct ggc agg cag       288
Asn Val Val His Leu Tyr Gln Glu Gln Gln Glu Leu Pro Gly Arg Gln
                85                  90                  95 atg ccg gcg ttc cgg aac agg acc aag ttg gtc aag gac gac atc gcc       336
Met Pro Ala Phe Arg Asn Arg Thr Lys Leu Val Lys Asp Asp Ile Ala
            100                 105                 110 tat ggc agc gtg gtc ctg cag ctt cac agc atc atc ccc tct gac aag       384
Tyr Gly Ser Val Val Leu Gln Leu His Ser Ile Ile Pro Ser Asp Lys
        115                 120                 125 ggc aca tat ggc tgc cgc ttc cac tcc gac aac ttc tct ggc gaa gct       432
Gly Thr Tyr Gly Cys Arg Phe His Ser Asp Asn Phe Ser Gly Glu Ala
    130                 135                 140 ctc tgg gaa ctg gag gta gca ggg ctg ggc tca gac cct cac ctc tcc       480
Leu Trp Glu Leu Glu Val Ala Gly Leu Gly Ser Asp Pro His Leu Ser
145                 150                 155                 160
```

```
ctt gag ggc ttc aag gaa gga ggc att cag ctg agg ctc aga tcc agt           528
Leu Glu Gly Phe Lys Glu Gly Gly Ile Gln Leu Arg Leu Arg Ser Ser
                165                 170                 175 ggc tgg tac ccc aag cct aag gtt cag tgg aga gac cac cag gga cag           576
Gly Trp Tyr Pro Lys Pro Lys Val Gln Trp Arg Asp His Gln Gly Gln
                180                 185                 190 tgc ctg cct cca gag ttt gaa gcc atc gtc tgg gat gcc cag gac ctg           624
Cys Leu Pro Pro Glu Phe Glu Ala Ile Val Trp Asp Ala Gln Asp Leu
                195                 200                 205 ttc agt ctg gaa aca tct gtg gtt gtc cga gcg gga gcc ctc agc aat           672
Phe Ser Leu Glu Thr Ser Val Val Val Arg Ala Gly Ala Leu Ser Asn
                210                 215                 220 gtg tcc gtc tcc atc cag aat ctc ctc ttg agc cag aag aaa gag ttg           720
Val Ser Val Ser Ile Gln Asn Leu Leu Leu Ser Gln Lys Lys Glu Leu
225                 230                 235                 240 gtg gtc cag ata gca gac gtg ttc gta ccc gga gcc tct gcg tgg aag           768
Val Val Gln Ile Ala Asp Val Phe Val Pro Gly Ala Ser Ala Trp Lys
                245                 250                 255 agc gga ggt gga ggc tcc gga ggt gga ggt tcc ggt gga ggt gga tcc           816
Ser Gly Gly Gly Gly Ser Gly Gly Gly Gly Ser Gly Gly Gly Gly Ser
                260                 265                 270 gac aaa act cac aca tgt cca ccg tgc cca gca cct gaa ctc ctg ggg           864
Asp Lys Thr His Thr Cys Pro Pro Cys Pro Ala Pro Glu Leu Leu Gly
                275                 280                 285 gga ccg tca gtt ttc ctc ttc ccc cca aaa ccc aag gac acc ctc atg           912
Gly Pro Ser Val Phe Leu Phe Pro Pro Lys Pro Lys Asp Thr Leu Met
290                 295                 300 atc tcc cgg acc cct gag gtc aca tgc gtg gtg gtg gac gtg agc cac           960
Ile Ser Arg Thr Pro Glu Val Thr Cys Val Val Val Asp Val Ser His
305                 310                 315                 320 gaa gac cct gag gtc aag ttc aac tgg tac gtg gac ggc gtg gag gtg          1008
Glu Asp Pro Glu Val Lys Phe Asn Trp Tyr Val Asp Gly Val Glu Val
                325                 330                 335 cat aat gcc aag aca aag ccg cgg gag gag cag tac aac agc acg tac          1056
His Asn Ala Lys Thr Lys Pro Arg Glu Glu Gln Tyr Asn Ser Thr Tyr
                340                 345                 350 cgt gtg gtc agc gtc ctc acc gtc ctg cac cag gac tgg ctg aat ggc          1104
Arg Val Val Ser Val Leu Thr Val Leu His Gln Asp Trp Leu Asn Gly
                355                 360                 365 aag gag tac aag tgc aag gtc tcc aac aaa gcc ctc cca gcc ccc atc          1152
Lys Glu Tyr Lys Cys Lys Val Ser Asn Lys Ala Leu Pro Ala Pro Ile
                370                 375                 380 gag aaa acc atc tcc aaa gcc aaa ggg cag ccc cga gaa cca cag gtg          1200
Glu Lys Thr Ile Ser Lys Ala Lys Gly Gln Pro Arg Glu Pro Gln Val
385                 390                 395                 400 tac acc ctg ccc cca tcc cgg gat gag ctg acc aag aac cag gtc agc          1248
Tyr Thr Leu Pro Pro Ser Arg Asp Glu Leu Thr Lys Asn Gln Val Ser
                405                 410                 415 ctg acc tgc ctg gtc aaa ggc ttc tat ccc agc gac atc gcc gtg gag          1296
Leu Thr Cys Leu Val Lys Gly Phe Tyr Pro Ser Asp Ile Ala Val Glu
                420                 425                 430 tgg gag agc aat ggg cag ccg gag aac aac tac aag acc acg cct ccc          1344
Trp Glu Ser Asn Gly Gln Pro Glu Asn Asn Tyr Lys Thr Thr Pro Pro
                435                 440                 445 gtg ctg gac tcc gac ggc tcc ttc ttc ctc tac agc aag ctc acc gtg          1392
Val Leu Asp Ser Asp Gly Ser Phe Phe Leu Tyr Ser Lys Leu Thr Val
                450                 455                 460 gac aag agc agg tgg cag cag ggg aac gtc ttc tca tgc tcc gtg atg          1440
Asp Lys Ser Arg Trp Gln Gln Gly Asn Val Phe Ser Cys Ser Val Met
465                 470                 475                 480
```

```
cat gag gct ctg cac aac cac tac acg cag aag agc ctc tcc ctg tct    1488
His Glu Ala Leu His Asn His Tyr Thr Gln Lys Ser Leu Ser Leu Ser
                485                 490                 495 ccg ggt aaa tga                                                    1500
Pro Gly Lys <210> SEQ ID NO 19
<211> LENGTH: 499
<212> TYPE: PRT
<213> ORGANISM: Artificial
<220> FEATURE:
<223> OTHER INFORMATION: Synthetic Construct

<400> SEQUENCE: 19

Met Val Asp Leu Ser Val Ser Pro Asp Ser Leu Lys Pro Val Ser Leu
1               5                   10                  15

Thr Ser Ser Leu Val Phe Leu Met His Leu Leu Leu Gln Pro Gly
            20                  25                  30

Glu Pro Ser Ser Glu Val Lys Val Leu Gly Pro Glu Tyr Pro Ile Leu
        35                  40                  45

Ala Leu Val Gly Glu Glu Val Glu Phe Pro Cys His Leu Trp Pro Gln
    50                  55                  60

Leu Asp Ala Gln Gln Met Glu Ile Arg Trp Phe Arg Ser Gln Thr Phe
65                  70                  75                  80

Asn Val Val His Leu Tyr Gln Glu Gln Gln Leu Pro Gly Arg Gln
                85                  90                  95

Met Pro Ala Phe Arg Asn Arg Thr Lys Leu Val Lys Asp Asp Ile Ala
            100                 105                 110

Tyr Gly Ser Val Val Leu Gln Leu His Ser Ile Ile Pro Ser Asp Lys
        115                 120                 125

Gly Thr Tyr Gly Cys Arg Phe His Ser Asp Asn Phe Ser Gly Glu Ala
    130                 135                 140

Leu Trp Glu Leu Glu Val Ala Gly Leu Gly Ser Asp Pro His Leu Ser
145                 150                 155                 160

Leu Glu Gly Phe Lys Glu Gly Gly Ile Gln Leu Arg Leu Arg Ser Ser
                165                 170                 175

Gly Trp Tyr Pro Lys Pro Lys Val Gln Trp Arg Asp His Gln Gly Gln
            180                 185                 190

Cys Leu Pro Pro Glu Phe Glu Ala Ile Val Trp Asp Ala Gln Asp Leu
        195                 200                 205

Phe Ser Leu Glu Thr Ser Val Val Arg Ala Gly Ala Leu Ser Asn
    210                 215                 220

Val Ser Val Ser Ile Gln Asn Leu Leu Leu Ser Gln Lys Lys Glu Leu
225                 230                 235                 240

Val Val Gln Ile Ala Asp Val Phe Val Pro Gly Ala Ser Ala Trp Lys
                245                 250                 255

Ser Gly Gly Gly Ser Gly Gly Gly Ser Gly Gly Gly Gly Ser
            260                 265                 270

Asp Lys Thr His Thr Cys Pro Pro Cys Pro Ala Pro Glu Leu Leu Gly
        275                 280                 285

Gly Pro Ser Val Phe Leu Phe Pro Pro Lys Pro Lys Asp Thr Leu Met
    290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
```

```
                    325                 330                 335
His Asn Ala Lys Thr Lys Pro Arg Glu Glu Gln Tyr Asn Ser Thr Tyr
            340                 345                 350

Arg Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
    370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys

<210> SEQ ID NO 20
<211> LENGTH: 2070
<212> TYPE: DNA
<213> ORGANISM: Artificial
<220> FEATURE:
<223> OTHER INFORMATION: Nucleotide sequence encoding a fusion protein
<220> FEATURE:
<221> NAME/KEY: CDS
<222> LOCATION: (1)..(2070)

<400> SEQUENCE: 20 atg gtg gat tgc cca cgg tat agt cta tct ggc gtg gct gcc tcc ttc      48
Met Val Asp Cys Pro Arg Tyr Ser Leu Ser Gly Val Ala Ala Ser Phe
1               5                   10                  15 ctc ttc gtc ctg ctg act ata aag cac cca gat gac ttc aga gtg gtc      96
Leu Phe Val Leu Leu Thr Ile Lys His Pro Asp Asp Phe Arg Val Val
            20                  25                  30 ggt cct aac ctc cca atc ctg gct aaa gtc ggg gaa gat gcc ctg cta     144
Gly Pro Asn Leu Pro Ile Leu Ala Lys Val Gly Glu Asp Ala Leu Leu
        35                  40                  45 acg tgt cag ctc ctc ccc aag agg acc acg gca cac atg gag gtg agg     192
Thr Cys Gln Leu Leu Pro Lys Arg Thr Thr Ala His Met Glu Val Arg
    50                  55                  60 tgg tac cgc tcc gac cct gcc atg cca gtg att atg tac cgg gat gga     240
Trp Tyr Arg Ser Asp Pro Ala Met Pro Val Ile Met Tyr Arg Asp Gly
65                  70                  75                  80 gct gtg gtg act ggg cta ccg atg gag ggg tac gga ggc cgg gca gag     288
Ala Val Val Thr Gly Leu Pro Met Glu Gly Tyr Gly Gly Arg Ala Glu
                85                  90                  95 tgg atg gag gac agc act gaa gag ggc agt gtg gct ctg aag att cgc     336
Trp Met Glu Asp Ser Thr Glu Glu Gly Ser Val Ala Leu Lys Ile Arg
            100                 105                 110 cag gtc cag cca agt gac gat ggc cag tac tgg tgc cgc ttc cag gag     384
Gln Val Gln Pro Ser Asp Asp Gly Gln Tyr Trp Cys Arg Phe Gln Glu
        115                 120                 125
```

| | | |
|---|---|---|
| ggg gac tac tgg aga gag aca agc gtg cta ctc caa gtg gct gct cta<br>Gly Asp Tyr Trp Arg Glu Thr Ser Val Leu Leu Gln Val Ala Ala Leu<br>130                              135                      140 | | 432 |
| gga tct tcc cca aat atc cat gtg gag gga ctt gga gaa gga gag gtc<br>Gly Ser Ser Pro Asn Ile His Val Glu Gly Leu Gly Glu Gly Glu Val<br>145                              150                      155                      160 | | 480 |
| caa ctt gta tgc acg tcc cga ggc tgg ttc cct gag cct gag gtg cac<br>Gln Leu Val Cys Thr Ser Arg Gly Trp Phe Pro Glu Pro Glu Val His<br>                        165                      170                      175 | | 528 |
| tgg gaa ggc atc tgg gga gaa aag ttg atg agt ttc tct gag aat cat<br>Trp Glu Gly Ile Trp Gly Glu Lys Leu Met Ser Phe Ser Glu Asn His<br>                            180                      185                      190 | | 576 |
| gtg cca ggt gaa gat ggg cta ttc tat gtg gaa gac aca ctg atg gtc<br>Val Pro Gly Glu Asp Gly Leu Phe Tyr Val Glu Asp Thr Leu Met Val<br>                195                      200                      205 | | 624 |
| agg aat gac agt gta gag acc att tcc tgc ttc atc tac agc cat ggc<br>Arg Asn Asp Ser Val Glu Thr Ile Ser Cys Phe Ile Tyr Ser His Gly<br>210                              215                      220 | | 672 |
| ctc aga gag acc cag gag gcc acc atc gct ctg tca gag agg ctc cag<br>Leu Arg Glu Thr Gln Glu Ala Thr Ile Ala Leu Ser Glu Arg Leu Gln<br>225                              230                      235                      240 | | 720 |
| acc gaa ctg gtt tcc gtt agc gta atc gga cat tcc cag ccc agc cct<br>Thr Glu Leu Val Ser Val Ser Val Ile Gly His Ser Gln Pro Ser Pro<br>                        245                      250                      255 | | 768 |
| gtt caa gtc gga gag aac ata gaa tta act tgt cac ctc tca cct caa<br>Val Gln Val Gly Glu Asn Ile Glu Leu Thr Cys His Leu Ser Pro Gln<br>                      260                      265                      270 | | 816 |
| acg gat gct cag aac tta gag gtg agg tgg ctc cga tcc cgc tat tac<br>Thr Asp Ala Gln Asn Leu Glu Val Arg Trp Leu Arg Ser Arg Tyr Tyr<br>                275                      280                      285 | | 864 |
| cct gca gtc cac gtg tat gca aat ggc acc cac gtg gct gga gag cag<br>Pro Ala Val His Val Tyr Ala Asn Gly Thr His Val Ala Gly Glu Gln<br>                        290                      295                      300 | | 912 |
| atg gta gaa tac aaa ggg agg act tca ttg gtg act gat gcc atc cac<br>Met Val Glu Tyr Lys Gly Arg Thr Ser Leu Val Thr Asp Ala Ile His<br>305                              310                      315                      320 | | 960 |
| gag gga aaa ctg acc ctg cag att cac aat gcc aga act tcg gat gaa<br>Glu Gly Lys Leu Thr Leu Gln Ile His Asn Ala Arg Thr Ser Asp Glu<br>                        325                      330                      335 | | 1008 |
| ggg cag tac cgg tgc ctt ttt gga aaa gat ggt gtc tac cag gag gcc<br>Gly Gln Tyr Arg Cys Leu Phe Gly Lys Asp Gly Val Tyr Gln Glu Ala<br>                      340                      345                      350 | | 1056 |
| cgt gtg gat gtg cag gtg acg gcg gtg ggt tcc acc cca cgg atc acc<br>Arg Val Asp Val Gln Val Thr Ala Val Gly Ser Thr Pro Arg Ile Thr<br>                    355                      360                      365 | | 1104 |
| agg gag gtc ttg aaa gat gga ggc atg cag ctg agg tgt acg tct gat<br>Arg Glu Val Leu Lys Asp Gly Gly Met Gln Leu Arg Cys Thr Ser Asp<br>370                              375                      380 | | 1152 |
| ggg tgg ttc cca cgg ccc cat gtg cag tgg agg gac aga gat gga aag<br>Gly Trp Phe Pro Arg Pro His Val Gln Trp Arg Asp Arg Asp Gly Lys<br>385                              390                      395                      400 | | 1200 |
| aca atg cca tcg ttt tcc gag gcc ttt cag caa ggg agc cag gag ctg<br>Thr Met Pro Ser Phe Ser Glu Ala Phe Gln Gln Gly Ser Gln Glu Leu<br>                        405                      410                      415 | | 1248 |
| ttc cag gtg gag aca ctt ctg ctg gtc aca aac ggc tcc atg gtg aat<br>Phe Gln Val Glu Thr Leu Leu Leu Val Thr Asn Gly Ser Met Val Asn<br>                    420                      425                      430 | | 1296 |
| gtg acc tgc tcc atc agc ctc cct ctg ggc cag gag aaa aca gcc cgt<br>Val Thr Cys Ser Ile Ser Leu Pro Leu Gly Gln Glu Lys Thr Ala Arg<br>                435                      440                      445 | | 1344 |

```
ttc cct ctc tca gac tcc aag tac gta gag ccc aga tct tgt gac aaa      1392
Phe Pro Leu Ser Asp Ser Lys Tyr Val Glu Pro Arg Ser Cys Asp Lys
    450                 455                 460 act cac aca tgc cca ccg tgc cca gca cct gaa gcc gag ggc gcg ccg      1440
Thr His Thr Cys Pro Pro Cys Pro Ala Pro Glu Ala Glu Gly Ala Pro
465                 470                 475                 480 tca gtc ttc ctc ttc ccc cca aaa ccc aag gac acc ctc atg atc tcc      1488
Ser Val Phe Leu Phe Pro Pro Lys Pro Lys Asp Thr Leu Met Ile Ser
                485                 490                 495 cgg acc cct gag gtc aca tgc gtg gtg gtg gac gtg agc cac gaa gac      1536
Arg Thr Pro Glu Val Thr Cys Val Val Val Asp Val Ser His Glu Asp
            500                 505                 510 cct gag gtc aag ttc aac tgg tac gtg gac ggc gtg gag gtg cat aat      1584
Pro Glu Val Lys Phe Asn Trp Tyr Val Asp Gly Val Glu Val His Asn
        515                 520                 525 gcc aag aca aag ccg cgg gag gag cag tac aac agc acg tac cgt gtg      1632
Ala Lys Thr Lys Pro Arg Glu Glu Gln Tyr Asn Ser Thr Tyr Arg Val
    530                 535                 540 gtc agc gtc ctc acc gtc ctg cac cag gac tgg ctg aat ggc aag gag      1680
Val Ser Val Leu Thr Val Leu His Gln Asp Trp Leu Asn Gly Lys Glu
545                 550                 555                 560 tac aag tgc aag gtc tcc aac aaa gcc ctc cca gcc ccc atc gag aaa      1728
Tyr Lys Cys Lys Val Ser Asn Lys Ala Leu Pro Ala Pro Ile Glu Lys
                565                 570                 575 acc atc tcc aaa gcc aaa ggg cag ccc cga gaa cca cag gtg tac acc      1776
Thr Ile Ser Lys Ala Lys Gly Gln Pro Arg Glu Pro Gln Val Tyr Thr
            580                 585                 590 ctg ccc cca tcc cgg gag gag atg acc aag aac cag gtc agc ctg acc      1824
Leu Pro Pro Ser Arg Glu Glu Met Thr Lys Asn Gln Val Ser Leu Thr
        595                 600                 605 tgc ctg gtc aaa ggc ttc tat ccc agc gac atc gcc gtg gag tgg gag      1872
Cys Leu Val Lys Gly Phe Tyr Pro Ser Asp Ile Ala Val Glu Trp Glu
    610                 615                 620 agc aat ggg cag ccg gag aac aac tac aag acc acg cct ccc gtg ctg      1920
Ser Asn Gly Gln Pro Glu Asn Asn Tyr Lys Thr Thr Pro Pro Val Leu
625                 630                 635                 640 gac tcc gac ggc tcc ttc ttc ctc tat agc aag ctc acc gtg gac aag      1968
Asp Ser Asp Gly Ser Phe Phe Leu Tyr Ser Lys Leu Thr Val Asp Lys
                645                 650                 655 agc agg tgg cag cag ggg aac gtc ttc tca tgc tcc gtg atg cat gag      2016
Ser Arg Trp Gln Gln Gly Asn Val Phe Ser Cys Ser Val Met His Glu
            660                 665                 670 gct ctg cac aac cac tac acg cag aag agc ctc tcc ctg tct ccg ggt      2064
Ala Leu His Asn His Tyr Thr Gln Lys Ser Leu Ser Leu Ser Pro Gly
        675                 680                 685 aaa tga                                                              2070
Lys
```

<210> SEQ ID NO 21
<211> LENGTH: 689
<212> TYPE: PRT
<213> ORGANISM: Artificial
<220> FEATURE:
<223> OTHER INFORMATION: Synthetic Construct

<400> SEQUENCE: 21

```
Met Val Asp Cys Pro Arg Tyr Ser Leu Ser Gly Val Ala Ala Ser Phe
1               5                   10                  15

Leu Phe Val Leu Leu Thr Ile Lys His Pro Asp Asp Phe Arg Val Val
            20                  25                  30
```

-continued

```
Gly Pro Asn Leu Pro Ile Leu Ala Lys Val Gly Glu Asp Ala Leu Leu
            35                  40                  45

Thr Cys Gln Leu Leu Pro Lys Arg Thr Thr Ala His Met Glu Val Arg
 50                  55                  60

Trp Tyr Arg Ser Asp Pro Ala Met Pro Val Ile Met Tyr Arg Asp Gly
 65                  70                  75                  80

Ala Val Val Thr Gly Leu Pro Met Glu Gly Tyr Gly Arg Ala Glu
                 85                  90                  95

Trp Met Glu Asp Ser Thr Glu Glu Gly Ser Val Ala Leu Lys Ile Arg
                100                 105                 110

Gln Val Gln Pro Ser Asp Gly Gln Tyr Trp Cys Arg Phe Gln Glu
                115                 120                 125

Gly Asp Tyr Trp Arg Glu Thr Ser Val Leu Leu Gln Val Ala Ala Leu
        130                 135                 140

Gly Ser Ser Pro Asn Ile His Val Glu Gly Leu Gly Glu Gly Glu Val
145                 150                 155                 160

Gln Leu Val Cys Thr Ser Arg Gly Trp Phe Pro Glu Pro Glu Val His
                165                 170                 175

Trp Glu Gly Ile Trp Gly Glu Lys Leu Met Ser Phe Ser Glu Asn His
        180                 185                 190

Val Pro Gly Glu Asp Gly Leu Phe Tyr Val Glu Asp Thr Leu Met Val
        195                 200                 205

Arg Asn Asp Ser Val Glu Thr Ile Ser Cys Phe Ile Tyr Ser His Gly
210                 215                 220

Leu Arg Glu Thr Gln Glu Ala Thr Ile Ala Leu Ser Glu Arg Leu Gln
225                 230                 235                 240

Thr Glu Leu Val Ser Val Ser Val Ile Gly His Ser Gln Pro Ser Pro
                245                 250                 255

Val Gln Val Gly Glu Asn Ile Glu Leu Thr Cys His Leu Ser Pro Gln
                260                 265                 270

Thr Asp Ala Gln Asn Leu Glu Val Arg Trp Leu Arg Ser Arg Tyr Tyr
        275                 280                 285

Pro Ala Val His Val Tyr Ala Asn Gly Thr His Val Ala Gly Glu Gln
        290                 295                 300

Met Val Glu Tyr Lys Gly Arg Thr Ser Leu Val Thr Asp Ala Ile His
305                 310                 315                 320

Glu Gly Lys Leu Thr Leu Gln Ile His Asn Ala Arg Thr Ser Asp Glu
                325                 330                 335

Gly Gln Tyr Arg Cys Leu Phe Gly Lys Asp Gly Val Tyr Gln Glu Ala
                340                 345                 350

Arg Val Asp Val Gln Val Thr Ala Val Gly Ser Thr Pro Arg Ile Thr
        355                 360                 365

Arg Glu Val Leu Lys Asp Gly Met Gln Leu Arg Cys Thr Ser Asp
370                 375                 380

Gly Trp Phe Pro Arg Pro His Val Gln Trp Arg Asp Arg Asp Gly Lys
385                 390                 395                 400

Thr Met Pro Ser Phe Ser Glu Ala Phe Gln Gln Gly Ser Gln Glu Leu
                405                 410                 415

Phe Gln Val Glu Thr Leu Leu Leu Val Thr Asn Gly Ser Met Val Asn
                420                 425                 430

Val Thr Cys Ser Ile Ser Leu Pro Leu Gly Gln Glu Lys Thr Ala Arg
        435                 440                 445
```

```
Phe Pro Leu Ser Asp Ser Lys Tyr Val Glu Pro Arg Ser Cys Asp Lys
            450                 455                 460

Thr His Thr Cys Pro Pro Cys Pro Ala Pro Glu Ala Glu Gly Ala Pro
465                 470                 475                 480

Ser Val Phe Leu Phe Pro Pro Lys Pro Lys Asp Thr Leu Met Ile Ser
                485                 490                 495

Arg Thr Pro Glu Val Thr Cys Val Val Val Asp Val Ser His Glu Asp
            500                 505                 510

Pro Glu Val Lys Phe Asn Trp Tyr Val Asp Gly Val Glu Val His Asn
        515                 520                 525

Ala Lys Thr Lys Pro Arg Glu Glu Gln Tyr Asn Ser Thr Tyr Arg Val
530                 535                 540

Val Ser Val Leu Thr Val Leu His Gln Asp Trp Leu Asn Gly Lys Glu
545                 550                 555                 560

Tyr Lys Cys Lys Val Ser Asn Lys Ala Leu Pro Ala Pro Ile Glu Lys
                565                 570                 575

Thr Ile Ser Lys Ala Lys Gly Gln Pro Arg Glu Pro Gln Val Tyr Thr
            580                 585                 590

Leu Pro Pro Ser Arg Glu Glu Met Thr Lys Asn Gln Val Ser Leu Thr
        595                 600                 605

Cys Leu Val Lys Gly Phe Tyr Pro Ser Asp Ile Ala Val Glu Trp Glu
610                 615                 620

Ser Asn Gly Gln Pro Glu Asn Asn Tyr Lys Thr Thr Pro Pro Val Leu
625                 630                 635                 640

Asp Ser Asp Gly Ser Phe Phe Leu Tyr Ser Lys Leu Thr Val Asp Lys
                645                 650                 655

Ser Arg Trp Gln Gln Gly Asn Val Phe Ser Cys Ser Val Met His Glu
            660                 665                 670

Ala Leu His Asn His Tyr Thr Gln Lys Ser Leu Ser Leu Ser Pro Gly
        675                 680                 685

Lys

<210> SEQ ID NO 22
<211> LENGTH: 466
<212> TYPE: PRT
<213> ORGANISM: Homo sapiens

<400> SEQUENCE: 22

Met Ala Phe Val Leu Ile Leu Val Leu Ser Phe Tyr Glu Leu Val Ser
1               5                   10                  15

Gly Gln Trp Gln Val Thr Gly Pro Gly Lys Phe Val Gln Ala Leu Val
            20                  25                  30

Gly Glu Asp Ala Val Phe Ser Cys Ser Leu Phe Pro Gly Thr Ser Ala
        35                  40                  45

Glu Ala Met Glu Val Arg Phe Phe Arg Asn Gln Phe His Ala Val Val
50                  55                  60

His Leu Tyr Arg Asp Gly Glu Asp Trp Glu Lys Gln Met Pro Gln
65                  70                  75                  80

Tyr Arg Gly Arg Thr Glu Phe Val Lys Asp Ser Ile Ala Gly Arg
                85                  90                  95

Val Ser Leu Arg Leu Lys Asn Ile Thr Pro Ser Asp Ile Gly Leu Tyr
            100                 105                 110

Gly Cys Trp Phe Ser Ser Gln Ile Tyr Asp Glu Glu Ala Thr Trp Glu
        115                 120                 125
```

Leu Arg Val Ala Ala Leu Gly Ser Leu Pro Leu Ile Ser Ile Val Gly
    130                 135                 140

Tyr Val Asp Gly Gly Ile Gln Leu Leu Cys Leu Ser Ser Gly Trp Phe
145                 150                 155                 160

Pro Gln Pro Thr Ala Lys Trp Lys Gly Pro Gln Gly Gln Asp Leu Ser
                165                 170                 175

Ser Asp Ser Arg Ala Asn Ala Asp Gly Tyr Ser Leu Tyr Asp Val Glu
                180                 185                 190

Ile Ser Ile Ile Val Gln Glu Asn Ala Gly Ser Ile Leu Cys Ser Ile
            195                 200                 205

His Leu Ala Glu Gln Ser His Glu Val Glu Ser Lys Val Leu Ile Gly
210                 215                 220

Glu Thr Phe Phe Gln Pro Ser Pro Trp Arg Leu Ala Ser Ile Leu Leu
225                 230                 235                 240

Gly Leu Leu Cys Gly Ala Leu Cys Gly Val Val Met Gly Met Ile Ile
                245                 250                 255

Val Phe Phe Lys Ser Lys Gly Lys Ile Gln Ala Glu Leu Asp Trp Arg
                260                 265                 270

Arg Lys His Gly Gln Ala Glu Leu Arg Asp Ala Arg Lys His Ala Val
            275                 280                 285

Glu Val Thr Leu Asp Pro Glu Thr Ala His Pro Lys Leu Cys Val Ser
290                 295                 300

Asp Leu Lys Thr Val Thr His Arg Lys Ala Pro Gln Glu Val Pro His
305                 310                 315                 320

Ser Glu Lys Arg Phe Thr Arg Lys Ser Val Val Ala Ser Gln Gly Phe
                325                 330                 335

Gln Ala Gly Lys His Tyr Trp Glu Val Asp Val Gly Gln Asn Val Gly
            340                 345                 350

Trp Tyr Val Gly Val Cys Arg Asp Asp Val Asp Arg Gly Lys Asn Asn
            355                 360                 365

Val Thr Leu Ser Pro Asn Asn Gly Tyr Trp Val Leu Arg Leu Thr Thr
370                 375                 380

Glu His Leu Tyr Phe Thr Phe Asn Pro His Phe Ile Ser Leu Pro Pro
385                 390                 395                 400

Ser Thr Pro Pro Thr Arg Val Gly Val Phe Leu Asp Tyr Glu Gly Gly
                405                 410                 415

Thr Ile Ser Phe Phe Asn Thr Asn Asp Gln Ser Leu Ile Tyr Thr Leu
            420                 425                 430

Leu Thr Cys Gln Phe Glu Gly Leu Leu Arg Pro Tyr Ile Gln His Ala
        435                 440                 445

Met Tyr Asp Glu Glu Lys Gly Thr Pro Ile Phe Ile Cys Pro Val Ser
    450                 455                 460

Trp Gly
465

<210> SEQ ID NO 23
<211> LENGTH: 500
<212> TYPE: PRT
<213> ORGANISM: Homo sapiens

<400> SEQUENCE: 23

Met Ala Leu Met Leu Ser Leu Val Leu Ser Leu Leu Lys Leu Gly Ser
1               5                   10                  15

Gly Gln Trp Gln Val Phe Gly Pro Asp Lys Pro Val Gln Ala Leu Val
            20                  25                  30

```
Gly Glu Asp Ala Ala Phe Ser Cys Phe Leu Ser Pro Lys Thr Asn Ala
        35                  40                  45

Glu Ala Met Glu Val Arg Phe Phe Arg Gly Gln Phe Ser Ser Val Val
 50                  55                  60

His Leu Tyr Arg Asp Gly Lys Asp Gln Pro Phe Met Gln Met Pro Gln
 65                  70                  75                  80

Tyr Gln Gly Arg Thr Lys Leu Val Lys Asp Ser Ile Ala Glu Gly Arg
                 85                  90                  95

Ile Ser Leu Arg Leu Glu Asn Ile Thr Val Leu Asp Ala Gly Leu Tyr
                100                 105                 110

Gly Cys Arg Ile Ser Ser Gln Ser Tyr Tyr Gln Lys Ala Ile Trp Glu
                115                 120                 125

Leu Gln Val Ser Ala Leu Gly Ser Val Pro Leu Ile Ser Ile Thr Gly
130                 135                 140

Tyr Val Asp Arg Asp Ile Gln Leu Leu Cys Gln Ser Ser Gly Trp Phe
145                 150                 155                 160

Pro Arg Pro Thr Ala Lys Trp Lys Gly Pro Gln Gly Gln Asp Leu Ser
                165                 170                 175

Thr Asp Ser Arg Thr Asn Arg Asp Met His Gly Leu Phe Asp Val Glu
                180                 185                 190

Ile Ser Leu Thr Val Gln Glu Asn Ala Gly Ser Ile Ser Cys Ser Met
                195                 200                 205

Arg His Ala His Leu Ser Arg Glu Val Glu Ser Arg Val Gln Ile Gly
210                 215                 220

Asp Thr Phe Phe Glu Pro Ile Ser Trp His Leu Ala Thr Lys Val Leu
225                 230                 235                 240

Gly Ile Leu Cys Cys Gly Leu Phe Phe Gly Ile Val Gly Leu Lys Ile
                245                 250                 255

Phe Phe Ser Lys Phe Gln Trp Lys Ile Gln Ala Glu Leu Asp Trp Arg
                260                 265                 270

Arg Lys His Gly Gln Ala Glu Leu Arg Asp Ala Arg Lys His Ala Val
                275                 280                 285

Glu Val Thr Leu Asp Pro Glu Thr Ala His Pro Lys Leu Cys Val Ser
290                 295                 300

Asp Leu Lys Thr Val Thr His Arg Lys Ala Pro Gln Glu Val Pro His
305                 310                 315                 320

Ser Glu Lys Arg Phe Thr Arg Lys Ser Val Ala Ser Gln Ser Phe
                325                 330                 335

Gln Ala Gly Lys His Tyr Trp Glu Val Asp Gly Gly His Asn Lys Arg
                340                 345                 350

Trp Arg Val Gly Val Cys Arg Asp Asp Val Asp Arg Lys Glu Tyr
                355                 360                 365

Val Thr Leu Ser Pro Asp His Gly Tyr Trp Val Leu Arg Leu Asn Gly
370                 375                 380

Glu His Leu Tyr Phe Thr Leu Asn Pro Arg Phe Ile Ser Val Phe Pro
385                 390                 395                 400

Arg Thr Pro Pro Thr Lys Ile Gly Val Phe Leu Asp Tyr Glu Cys Gly
                405                 410                 415

Thr Ile Ser Phe Phe Asn Ile Asn Asp Gln Ser Leu Ile Tyr Thr Leu
                420                 425                 430

Thr Cys Arg Phe Glu Gly Leu Leu Arg Pro Tyr Ile Glu Tyr Pro Ser
                435                 440                 445
```

```
Tyr Asn Glu Gln Asn Gly Thr Pro Ile Val Ile Cys Pro Val Thr Gln
    450                 455                 460

Glu Ser Glu Lys Glu Ala Ser Trp Gln Arg Ala Ser Ala Ile Pro Glu
465                 470                 475                 480

Thr Ser Asn Ser Glu Ser Ser Gln Ala Thr Thr Pro Phe Leu Pro
                485                 490                 495

Arg Gly Glu Met
            500

<210> SEQ ID NO 24
<211> LENGTH: 475
<212> TYPE: PRT
<213> ORGANISM: Homo sapiens

<400> SEQUENCE: 24

Met Glu Met Ala Ser Ser Ala Gly Ser Trp Leu Ser Gly Cys Leu Ile
1               5                   10                  15

Pro Leu Val Phe Leu Arg Leu Ser Val His Val Ser Gly His Ala Gly
                20                  25                  30

Asp Ala Gly Lys Phe His Val Ala Leu Leu Gly Gly Thr Ala Glu Leu
            35                  40                  45

Leu Cys Pro Leu Ser Leu Trp Pro Gly Thr Val Pro Lys Glu Val Arg
50                  55                  60

Trp Leu Arg Ser Pro Phe Pro Gln Arg Ser Gln Ala Val His Ile Phe
65                  70                  75                  80

Arg Asp Gly Lys Asp Gln Asp Glu Asp Leu Met Pro Glu Tyr Lys Gly
                85                  90                  95

Arg Thr Val Leu Val Arg Asp Ala Gln Glu Gly Ser Val Thr Leu Gln
            100                 105                 110

Ile Leu Asp Val Arg Leu Glu Asp Gln Gly Ser Tyr Arg Cys Leu Ile
            115                 120                 125

Gln Val Gly Asn Leu Ser Lys Glu Asp Thr Val Ile Leu Gln Val Ala
        130                 135                 140

Ala Pro Ser Val Gly Ser Leu Ser Pro Ser Ala Val Ala Leu Ala Val
145                 150                 155                 160

Ile Leu Pro Val Leu Val Leu Ile Met Val Cys Leu Cys Leu Ile
                165                 170                 175

Trp Lys Gln Arg Arg Ala Lys Glu Lys Leu Leu Tyr Glu His Val Thr
                180                 185                 190

Glu Val Asp Asn Leu Leu Ser Asp His Ala Lys Glu Lys Gly Lys Leu
            195                 200                 205

His Lys Ala Val Lys Lys Leu Arg Ser Glu Leu Lys Leu Lys Arg Ala
210                 215                 220

Ala Ala Asn Ser Gly Trp Arg Arg Ala Arg Leu His Phe Val Ala Val
225                 230                 235                 240

Thr Leu Asp Pro Asp Thr Ala His Pro Lys Leu Ile Leu Ser Glu Asp
                245                 250                 255

Gln Arg Cys Val Arg Leu Gly Asp Arg Arg Gln Pro Val Pro Asp Asn
            260                 265                 270

Pro Gln Arg Phe Asp Phe Val Val Ser Ile Leu Gly Ser Glu Tyr Phe
        275                 280                 285

Thr Thr Gly Cys His Tyr Trp Glu Val Tyr Val Gly Asp Lys Thr Lys
290                 295                 300

Trp Ile Leu Gly Val Cys Ser Glu Ser Val Ser Arg Lys Gly Lys Val
305                 310                 315                 320
```

Thr Ala Ser Pro Ala Asn Gly His Trp Leu Leu Arg Gln Ser Arg Gly
                325                 330                 335

Asn Glu Tyr Glu Ala Leu Thr Ser Pro Gln Thr Ser Phe Arg Leu Lys
            340                 345                 350

Glu Pro Pro Arg Cys Val Gly Ile Phe Leu Asp Tyr Glu Ala Gly Val
        355                 360                 365

Ile Ser Phe Tyr Asn Val Thr Asn Lys Ser His Ile Phe Thr Phe Thr
    370                 375                 380

His Asn Phe Ser Gly Pro Leu Arg Pro Phe Phe Glu Pro Cys Leu His
385                 390                 395                 400

Asp Gly Gly Lys Asn Thr Ala Pro Leu Val Ile Cys Ser Glu Leu His
                405                 410                 415

Lys Ser Glu Glu Ser Ile Val Pro Arg Pro Glu Gly Lys Gly His Ala
            420                 425                 430

Asn Gly Asp Val Ser Leu Lys Val Asn Ser Ser Leu Leu Pro Pro Lys
        435                 440                 445

Ala Pro Glu Leu Lys Asp Ile Ile Leu Ser Leu Pro Pro Asp Leu Gly
    450                 455                 460

Pro Ala Leu Gln Glu Leu Lys Ala Pro Ser Phe
465                 470                 475

<210> SEQ ID NO 25
<211> LENGTH: 252
<212> TYPE: PRT
<213> ORGANISM: Homo sapiens

<400> SEQUENCE: 25

Met Ala Ser Leu Ser Arg Pro Ser Leu Pro Ser Cys Leu Cys Ser Phe
1               5                   10                  15

Leu Leu Leu Leu Leu Leu Gln Val Ser Ser Ser Tyr Ala Gly Gln Phe
                20                  25                  30

Arg Val Ile Gly Pro Arg His Pro Ile Arg Ala Leu Val Gly Asp Glu
            35                  40                  45

Val Glu Leu Pro Cys Arg Ile Ser Pro Gly Lys Asn Ala Thr Gly Met
        50                  55                  60

Glu Val Gly Trp Tyr Arg Pro Pro Phe Ser Arg Val Val His Leu Tyr
65                  70                  75                  80

Arg Asn Gly Lys Asp Gln Asp Gly Asp Gln Ala Pro Glu Tyr Arg Gly
                85                  90                  95

Arg Thr Glu Leu Leu Lys Asp Ala Ile Gly Glu Gly Lys Val Thr Leu
            100                 105                 110

Arg Ile Arg Asn Val Arg Phe Ser Asp Glu Gly Gly Phe Thr Cys Phe
        115                 120                 125

Phe Arg Asp His Ser Tyr Gln Glu Glu Ala Ala Met Glu Leu Lys Val
    130                 135                 140

Glu Asp Pro Phe Tyr Trp Val Ser Pro Gly Val Leu Val Leu Leu Ala
145                 150                 155                 160

Val Leu Pro Val Leu Leu Leu Gln Ile Thr Val Gly Leu Val Phe Leu
                165                 170                 175

Cys Leu Gln Tyr Arg Leu Arg Gly Lys Leu Arg Ala Glu Ile Glu Asn
            180                 185                 190

Leu His Arg Thr Phe Asp Pro His Phe Leu Arg Val Pro Cys Trp Lys
        195                 200                 205

Ile Thr Leu Phe Val Ile Val Pro Val Leu Gly Pro Leu Val Ala Leu

-continued

```
                210             215             220
Ile Ile Cys Tyr Asn Trp Leu His Arg Arg Leu Ala Gly Gln Phe Leu
225                 230             235                 240

Glu Glu Leu Leu Phe His Leu Glu Ala Leu Ser Gly
                245             250
```

<210> SEQ ID NO 26
<211> LENGTH: 282
<212> TYPE: PRT
<213> ORGANISM: Homo sapiens

<400> SEQUENCE: 26

```
Tyr Ala Glu Ala Thr Leu Val Val Arg Asn Ala Ser Ala Glu Ser Val
1               5                   10                  15

Ser Cys Leu Val His Asn Pro Val Leu Thr Glu Glu Lys Gly Ser Val
                20                  25                  30

Ile Ser Leu Pro Glu Lys Leu Gln Thr Glu Leu Ala Ser Leu Lys Val
                35                  40                  45

Asn Gly Pro Ser Gln Pro Ile Leu Val Arg Val Gly Glu Asp Ile Gln
            50                  55                  60

Leu Thr Cys Tyr Leu Ser Pro Lys Ala Asn Ala Gln Ser Met Glu Val
65                  70                  75                  80

Arg Trp Asp Arg Ser His Arg Tyr Pro Ala Val His Val Tyr Met Asp
                    85                  90                  95

Gly Asp His Val Ala Gly Glu Gln Met Ala Glu Tyr Arg Gly Arg Thr
                100                 105                 110

Val Leu Val Ser Asp Ala Ile Asp Glu Gly Arg Leu Thr Leu Gln Ile
                115                 120                 125

Leu Ser Ala Arg Pro Ser Asp Asp Gly Gln Tyr Arg Cys Leu Phe Glu
            130                 135                 140

Lys Asp Asp Val Tyr Gln Glu Ala Ser Leu Asp Leu Lys Val Val Gly
145                 150                 155                 160

Leu Gly Ser Ser Pro Leu Ile Thr Val Glu Gly Gln Glu Asp Gly Glu
                165                 170                 175

Met Gln Pro Met Cys Ser Ser Asp Gly Trp Phe Pro Gln Pro His Val
                180                 185                 190

Pro Trp Arg Asp Met Glu Gly Lys Thr Ile Pro Ser Ser Ser Gln Ala
                195                 200                 205

Leu Thr Gln Gly Ser His Gly Leu Phe His Val Gln Thr Leu Leu Arg
            210                 215                 220

Val Thr Asn Ile Ser Ala Val Asp Val Thr Cys Ser Ile Ser Ile Pro
225                 230                 235                 240

Phe Leu Gly Glu Glu Lys Ile Ala Thr Phe Ser Leu Ser Glu Ser Arg
                245                 250                 255

Met Thr Phe Leu Trp Lys Thr Leu Leu Val Trp Gly Leu Leu Leu Ala
                260                 265                 270

Val Ala Val Gly Leu Pro Arg Lys Arg Ser
                275                 280
```

BTNL9 PROTEINS, NUCLEIC ACIDS, AND ANTIBODIES AND USES THEREOF

CROSS REFERENCE TO RELATED APPLICATIONS

This application is a continuation U.S. application Ser. No. 13/640,232, filed Dec. 18, 2012, pending, which is a National Stage application under 35 U.S.C. § 371 of International Application No. PCT/US2011/031811 (which designated the United States), having an international filing date of Apr. 8, 2011, which claims priority to U.S. Provisional Patent Application Ser. No. 61/322,800, filed Apr. 9, 2010. The above-identified applications are incorporated herein by reference.

REFERENCE TO THE SEQUENCE LISTING

The present application is being filed along with a Sequence Listing in electronic format via EFS-Web. The Sequence Listing is provided as a text file entitled A1568USCNTst25.txt, created May 5, 2015, which is 85,707 bytes in size. The information in the electronic format of the Sequence Listing is incorporated herein by reference in its entirety.

FIELD OF THE INVENTION

This invention relates to a butyrophilin-like protein and fragments, variants, and derivatives thereof, nucleic acids encoding such proteins, antibodies that bind to these proteins, and agonists and antagonists of these proteins. Pharmaceutical compositions containing such molecules and uses for such molecules or compositions containing them are also contemplated.

BACKGROUND

Modulation of an immune or inflammatory response may be valuable in various therapeutic settings. Downmodulation of an immune or inflammatory response may be desirable in treatments various kinds of autoimmune or inflammatory diseases. Upmodulation of any immune response may be valuable to, for example, amplify a response to a particular antigen, for example, an antigen contained in a vaccine or an antigen preferentially expressed on a cancer cell or a cell mediating a fibrotic disease. Thus, molecules capable of modulating an immune or inflammatory response are potentially of therapeutic value in a variety of therapeutic settings. The present invention provides therapeutic agents to diagnose and treat diseases characterized by inappropriate and/or abnormal inflammation and/or immune responses. Some of these agents can stimulate an immune response. Others can inhibit inflammation and/or immune responses.

SUMMARY

The invention provides BTNL9 proteins, nucleic acids encoding them, and antibodies that bind to them. More specifically, the BTNL9 proteins described herein are multimeric proteins and or fusion proteins that can be isolated and/or soluble proteins. Also provided are uses for BTNL9 proteins and for antagonistic and agonistic antibodies that bind to BTNL9.

In one embodiment, the invention encompasses an isolated soluble multimeric BTNL9 protein comprising (a) a polypeptide having an amino acid sequence at least 90%, 95%, 96%, 97%, 98%, or 99% identical to amino acids 35-257 of SEQ ID NO:2 and (b) a second polypeptide having an amino acid sequence at least 90%, 95%, 96%, 97%, 98%, or 99% identical to amino acids 35-257 of SEQ ID NO:2, wherein the alignment window of the amino acid sequences of the polypeptides of (a) and (b) with amino acids 35-257 of SEQ ID NO:1 is at least 80 amino acids long, wherein the multimer is at least a trimer, and wherein the multimeric BTNL9 protein can inhibit the proliferation of a T cell stimulated by an anti-CD3 antibody. In a slightly different embodiment, the invention provides isolated soluble multimeric BTNL9 protein comprising
(a) a polypeptide having an amino acid sequence at least 90% identical to amino acids 35-257 of SEQ ID NO:2, and (b) a second polypeptide having an amino acid sequence at least 90% identical to amino acids 35-257 of SEQ ID NO:2, wherein the alignment window of the amino acid sequences of the polypeptides of (a) and (b) with amino acids 35-257 of SEQ ID NO:2 is at least 80 amino acids long, wherein the multimer has a molecular weight that is greater than about three times as large as that of a monomeric polypeptide of (a) and/or at least about four, five, six, seven, eight, nine, ten, eleven, twelve, thirteen, fourteen, fifteen, or sixteen times as large as that of a monomeric polypeptide of (a), and wherein the multimeric BTNL9 protein can inhibit the proliferation of a T cell stimulated by an anti-CD3 antibody. The multimeric BTNL9 protein in either of these embodiments can also be at least a trimer, a tetramer, a pentamer, a hexamer, a heptamer, an octomer, a nonamer, a decamer, and/or a higher order multimer, which also means that the multimeric BTNL9 protein can be a trimer, tetramer, a pentamer, a hexamer, a heptamer, an octomer, a nonamer, a decamer, and/or a higher order multimer. The multimeric BTNL9 protein can comprise the amino acid sequence from, amino acid 35, 36, 37, 38, 39, or 40 to 253, 254, 255, 256, or 257 of SEQ ID NO:2. In some embodiments, the multimeric BNTL9 protein does not comprise amino acids 258 to 277 of SEQ ID NO:2, and in some embodiments it may comprise another polypeptide, such as, for example, an Fc portion of an antibody. Such an Fc portion can comprise (i) the amino acid sequence of a native human Fc region or (ii) an amino acid sequence that is substantially similar to that of the native human Fc region having not more than 15, not more than 10, or not more than 5 insertions, deletions, or substitutions of a single amino acid relative to the amino acid sequence of the native human Fc region. The native human Fc may be of the IgG1, IgG2, IgG3, IgG4, IgA, IgD, IgM, or IgE isotype. The multimeric BTNL9 protein can be a homotetramer, a homopentamer, a homohexamer, a homoheptamer, a homooctamer, a homononamer, a homodecamer, a higher order homomultimer, a heteromultimer, or a mixture of species. Nucleic acids encoding such multimeric BTNL9 proteins are also provided, as well as vectors comprising these nucleic acids and host cells containing the vectors and/or the nucleic acids.

In another embodiment, the invention provides a BTNL9 fusion protein comprising (a) a first polypeptide comprising an amino acid sequence at least 90%, 95%, 96%, 97%, 98%, or 99% identical to amino acids 35-257 of SEQ ID NO:2, wherein the wherein the alignment window of the amino acid sequence of the BTNL9 fusion protein with amino acids 35-257 is SEQ ID NO:2 is at least 80 amino acids long, and (b) a second polypeptide, wherein the BTNL9 fusion protein can inhibit the proliferation of a T cell stimulated by an anti-CD3 antibody. The fusion protein can be an isolated and/or a soluble protein. The second polypeptide can be an Fc portion of an antibody, wherein the Fc portion has an amino acid sequence that is identical or substantially similar to an amino acid sequence of a native human Fc region and contains not more than 5, 10, 15, or 20 insertions, deletions, or substitutions of a single amino acid relative to the native human Fc region. The native human Fc region can be of the IgG1, , IgG2, IgG3, IgG4, IgA, IgD, IgE, or IgM isotype. The BTNL9 fusion protein can comprise amino acids 35-257 of SEQ ID NO:2. The BTNL9 fusion protein can comprise an amino acid sequence that is substantially similar to SEQ ID NO:18, wherein the amino acid sequence comprises not more than 5, 10, 15, or 20 insertions, deletions, or substitutions of a single amino acid relative to SEQ ID NO:18, and/or the BTNL9 fusion protein can comprise SEQ ID NO:18. The BTNL9 fusion protein can be at least a trimer, a tetramer, a pentamer, a hexamer, a heptamer, an octamer, a nonamer, or a decanter. The BTNL9 fusion protein can comprise a linker. Such a BTNL9 fusion protein can be a multimer, wherein the multimer has a molecular weight at least about four, five, six, seven, eight, nine, ten, eleven, twelve, thirteen, fourteen, fifteen, or sixteen times as large as that of the monomeric BTNL9 fusion protein. Nucleic acids encoding such BTNL9 fusion proteins are also provided, as well as vectors comprising these nucleic acids and host cells containing the vectors and/or the nucleic acids.

In another embodiment, the invention provides a soluble BTNL9 protein comprising the amino acid sequence of a fragment of SEQ ID NO:2 extending from position 40-140 of SEQ ID NO:2 or a variant thereof comprising no more than 5 or 10 insertions, deletions, or substitutions of a single amino acid relative to amino acids 40-140 of SEQ ID NO:2, wherein the BTNL9 protein does not also comprise the amino acid sequence of a fragment of SEQ ID NO:2 extending from position 160 to 248 of SEQ ID NO:2 or a variant thereof comprising no more than 20, 15, 10, 10, or 5 insertions, deletions, or substitutions of a single amino acid relative to amino acids 160-248 of SEQ ID NO:2, and wherein the BTNL9 protein can inhibit the proliferation of a T cell stimulated by an anti-CD3 antibody. The soluble BTNL9 protein may comprise no more than 5 insertions, deletions or substitutions of a single-amino acid relative to amino acids 40-140 of SEQ ID NO:2. Or, in another aspect, the amino acid sequence of the soluble BTNL9 protein can be at least 90%, 95%, 96%, 97%, 98%, 99%, or 100% identical to ammo acids 40-140 of SEQ ID NO:2. The soluble BTNL9 protein can be at least a trimer, a tetramer, a pentamer, a hexamer, a heptamer, an octamer, a nonamer, or a decamer. Such a BTNL9 protein can also be a trimer, a tetramer, a pentamer, a hexamer, a heptamer, an octamer, a nonamer, a decamer, a higher order multimer, or a mixture of these species. Such a soluble BTNL9 protein can be a multimer, wherein the multimer has a molecular weight at least about four, five, six, seven, eight, nine, ten, eleven, twelve, thirteen, fourteen, fifteen, or sixteen times as large as that of the monomeric soluble BTNL9 protein. Such a soluble BTNL9 protein can further comprise another polypeptide, such as, for example, an Fc fragment of an antibody and/or a linker. Nucleic acids encoding such soluble BTNL9 proteins are also provided, as well as vectors comprising these nucleic acids and host cells containing the vectors and/or the nucleic acids.

Alternatively, a soluble BTNL9 protein can comprise the amino acid sequence of a fragment of SEQ ID NO:2 extending from position 160 to 248 of SEQ ID NO:2 or a variant thereof comprising no more than 20, 15, 10, or 5 insertions, deletions, or substitutions of a single amino acid relative to amino acids 160-248 of SEQ ID NO:2, wherein the BTNL9 protein does not also comprise the amino acid sequence of a fragment of SEQ ID NO:2 extending from position 40-140 of SEQ ID NO:2 or a variant thereof comprising no more than 10 insertions, deletions, or substitutions of a single amino acid relative to amino acids 40-140 of SEQ ID NO:2, and wherein the BTNL9 protein can inhibit the proliferation of a T cell stimulated by an anti-CD3 antibody. Such a soluble BTNL9 protein can be at least a trimer, a tetramer, a pentamer, a hexamer, a heptamer, an octamer, a nonamer, a decamer, or a higher order multimer. Such a BTNL9 protein can further comprise another polypeptide, such as, for example, an Fc fragment of an antibody and/or a linker. Such a soluble BTNL9 protein can be a multimer, wherein the multimer has a molecular weight at least about four, five, six, seven, eight, nine, ten, eleven, twelve, thirteen, fourteen, fifteen, or sixteen times as large as that of the monomeric soluble BTNL9 protein. Nucleic acids encoding such BTNL9 fusion proteins are also provided, as well as vectors comprising these nucleic acids and host cells containing the vectors and/or the nucleic acids.

In a further embodiment, there is provided a BTNL9 fusion protein encoded by a nucleic acid, wherein the nucleic acid comprises the following: (a) a polynucleotide, which encodes a polypeptide, (i) that consists of the nucleotide sequence from nucleotide 334, 337, 340, or 343 to 990, 993, 996, 999, or 1002 of SEQ ID NO:1 or (ii) that hybridizes under stringent conditions to the polynucleotide of (i); and (b) a polynucleotide that does not hybridize to a polynucleotide consisting of the sequence of SEQ ID NO:1 and encodes a polypeptide in frame with the polypeptide encoded by the polynucleotide of (a); wherein the fusion protein can inhibit the proliferation of a T cell stimulated by an anti-CD3 antibody. The BTNL9 fusion protein can comprise a linker sequence and can be an isolated and/or soluble protein. Such a BTNL9 fusion protein can be a multimer, wherein the multimer has a molecular weight at least about four, five, six, seven, eight, nine, ten, eleven, twelve, thirteen, fourteen, fifteen, or sixteen times as large as that of the monomeric BTNL9 fusion protein. Nucleic acids encoding such BTNL9 fusion proteins are also provided, as well as vectors comprising these nucleic acids and host cells containing the vectors and/or the nucleic acids.

Any of the BTNL9 proteins discussed above or below can be isolated and/or soluble and can comprise multimers or aggregated species, which comprise multiple molecules of a BTNL9 protein. The molecular weight of the monomeric BTNL9 protein species contained in the multimer or aggregate can be measured by gel electrophoresis under reducing conditions or by size exclusion chromatography (SEC) done under reducing conditions. The molecular weight of the multimeric or aggregated species can be measured by gel electrophoresis or SEC done under non-reducing conditions. In some embodiments the multimer or aggregate has a molecular weight that is at least about 4, 5, 6, 7, 8, 9, 10, 11, 12, 13, 14, 15, or 16 times that of the monomeric species. The monomeric BTNL9 protein of such a multimer or aggregate comprises (a) a polypeptide containing the amino acid sequence from ammo acid 35, 36, 37, 38, 39, or 40 to 253, 254, 255, 256, or 257 of SEQ ID NO:2 or (b) a polypeptide having an ammo acid sequence at least 90%, 95%, 97% or 99% identical to amino acids 35-257 of SEQ ID NO:2 wherein the alignment window of the amino acid sequence of the polypeptide of (b) with amino acids 35-257 of SEQ ID NO:2 is at least 80 amino acids long or (c) a polypeptide having a sequence like that of amino acids 35-257 of SEQ ID NO:2 except that it can contain no more than 20, 15, 10, or 5 insertions, deletions, or substitutions of a single amino acid relative to SEQ ID NO:2.

In another aspect, there is provided a nucleic acid encoding a fusion protein comprising a BTNL9 protein and another polypeptide, wherein the nucleic acid comprises: (a) a polynucleotide (i) that consists of the nucleotide sequence from nucleotide 334, 337, 340, or 343 to 990, 993, 996, 999, or 1002 of SEQ ID NO:1 or (ii) that hybridizes under stringent conditions to the polynucleotide of (i); and (b) a polynucleotide that does not hybridize to a polynucleotide consisting of the sequence of SEQ ID NO:1 and encodes a polypeptide in frame with the polypeptide encoded by the polynucleotide of (a); wherein the fusion protein can inhibit the proliferation of a T cell stimulated by an anti-CD3 antibody. Vectors containing these nucleic acids and host cells containing the vectors and/or the nucleic acids are also contemplated.

The invention provides a method of making any of the BTNL9 proteins discussed above, including the multimeric BTNL9 protein, the BTNL9 fusion proteins, and the soluble BTNL9 protein, comprising culturing a host cell containing nucleic acids encoding the BTNL9 protein in a medium under conditions suitable for expression of the nucleic acid and recovering the expressed BTNL9 protein from the cell mass or the culture medium.

In still another aspect, a method of treating a patient having an autoimmune or inflammatory disease is provided, which comprises administering to the patient a therapeutically effective dose of (1) any BTNL9 protein comprising the amino acid sequence of amino acid 35-257 of SEQ ID NO:2 or (2) a variant thereof which comprises an amino acid sequence at least 90%, 95%, 96%, 97%, 98% or 99% identical to amino acids 35-257 of SEQ ID NO:2 or which comprises an amino acid sequence that has no more than 5, 10, 15, or 20 insertions, deletions, or substitutions of a single amino acid relative to the sequence of amino acids 35-257 of SEQ ID NO:2, wherein the BTNL9 protein can inhibit the proliferation of a T cell stimulated by an anti-CD3 antibody. This method would include the use of the soluble multimeric BTNL9 protein, the BTNL9 fusion proteins, or the soluble BTNL9 protein discussed above for practicing the method. The autoimmune or inflammatory disease can be rheumatoid arthritis, an inflammatory bowel disease, Crohn's disease, ulcerative colitis, psoriasis, sarcoidosis, multiple sclerosis, chronic obstructive pulmonary disease, asthma, or a fibrotic disease.

In a further aspect, a method for inhibiting I cell proliferation is provided, which comprises adding to the T cell (1) any BTNL9 protein comprising the amino acid sequence from amino acid 35, 36, 37, 38, 39, or 40 to 253, 254, 255, 256, or 257 of SEQ ID NO:2 or (2) a variant thereof which comprises an amino acid sequence at least 90%, 95%, 96%, 97%, 98% or 99% identical to amino acids 35-257 of SEQ ID NO:2 or which comprises an amino acid sequence that has no more than 5, 10, 15, or 20 insertions, deletions, or substitutions of a single amino acid relative to the sequence of amino acids 35-257 of SEQ ID NO:2, wherein the BTNL9 protein can inhibit the proliferation T cells stimulated by an anti-CD3 antibody. This method encompasses the use of soluble multimeric BTNL9 protein, the BTNL9 fusion proteins, or the soluble BTNL9 protein discussed above to inhibit T cell proliferation. This inhibition of T cell proliferation can occur in vitro or in vivo.

Another embodiment includes a method for treating a patient having an autoimmune or inflammatory disease comprising administering to the patient a therapeutically effective dose of an anti-BTNL9 antibody, wherein the anti-BTNL9 antibody increases the inhibition of proliferation of T cells by the soluble multimeric BTNL9 protein, one of the BTNL9 fusion proteins, and/or the soluble BTNL9 protein as discussed above and wherein the anti-BTNL9 antibody binds to a protein consisting of the amino acid sequence of amino acids 35 to 257 of SEQ ID NO:2.

Another embodiment includes a method for treating a patient having an autoimmune or inflammatory disease, as described herein, comprising administering to the patient a therapeutically effective dose of an anti-BTNL9 antibody, wherein the anti-BTNL9 antibody can bind to a protein consisting of the amino acid sequence of amino acids 35 to 257 of SEQ ID NO:2. In some embodiments, the anti-BTNL9 antibody can bind to a cell surface BTNL9 protein and induce an intracellular signaling cascade via the B30.2 domain of BTNL9.

A further method includes a treatment for a cancer patient comprising administering to the patient a therapeutically effective amount of an antibody that binds to a BTNL9 protein consisting of amino acids 35 to 257 of SEQ ID NO:2. The cancer can be, for example, acute or chronic leukemias, lymphoma, non-Hodgkin's lymphoma, Hodgkin's disease, lymphocytic leukemias, lymphocytic or cutaneous lymphomas, carcinomas, sarcomas, thymomas, neoplasms of the mediastinum, breast cancer, prostate cancer, cancers of the head and neck, lung cancer, non-small cell lung cancer, small cell lung cancer, various kinds of skin cancer, cancer of the bladder, malignant gliomas, cancer of the esophagus, cancer of the stomach, cancer of the pancreas, hepatobiliary neoplasms, cancer of the small intestine, colon, or rectum, cancer of the kidney or ureter, testicular cancer, cancer of the urethra or penis, gynecologic tumors, ovarian cancer, sarcomas of the bone, cancers of the endocrine system, cutaneous melanoma, intraocular melanoma, neoplasms of the central nervous system, and plasma cell neoplasms. The antibody can be an antagonistic antibody.

Finally, a method is provided for vaccinating a patient against a cancer, which comprises administering to the patient an antigen that is highly expressed on the cancer cells and an antagonistic antibody that binds to a protein consisting of amino acids 35 to 257 of SEQ ID NO:2.

11, eosinophils; 12, neutrophils; 13, basophils; and 14, platelets. Methods are described in detail in Example 1.

Figure 3:
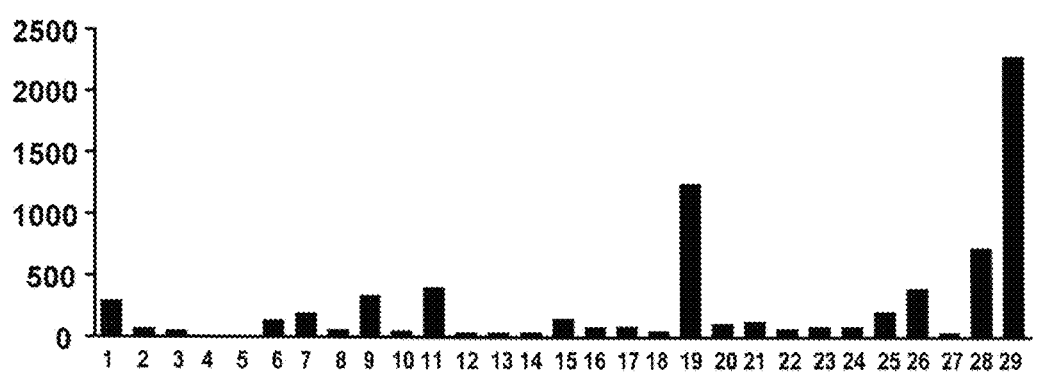

FIG. 3: This figure shows the relative levels of expression of BTNL9 mRNA in various adult human tissues as determined by hybridization to a BTNL9 probe on a microarray. Intensity values for expression of BTNL9 mRNA are indicated on the vertical axis. The various tissues are indicated on the horizontal axis as follows: 1, adrenal gland; 2, bladder; 3, bladder carcinoma; 4, bone marrow; 5, bone marrow mononuclear cells; 6, brain; 7, breast; 8, colon; 9, colon adenocarcinoma cells; 10, normal-appearing margin of a colon biopsy; 11, heart; 12, hyperplastic prostate; 13, ileum from a non-Hodgkins lymphoma patient; 14, normal-appearing margin from an ileum biopsy; 15, kidney; 16, squamous carcinoma cells from larynx; 17, normal-appearing margin from a larynx biopsy; 18, liver; 19, lung; 20, ovary; 21, placenta; 22, prostate; 23, skeletal muscle; 24, skin; 25, small intestine; 26, spleen; 27, testes; 28, thymus; and 29, white adipose tissue. Methods are described in Example 1.

Figure 4:
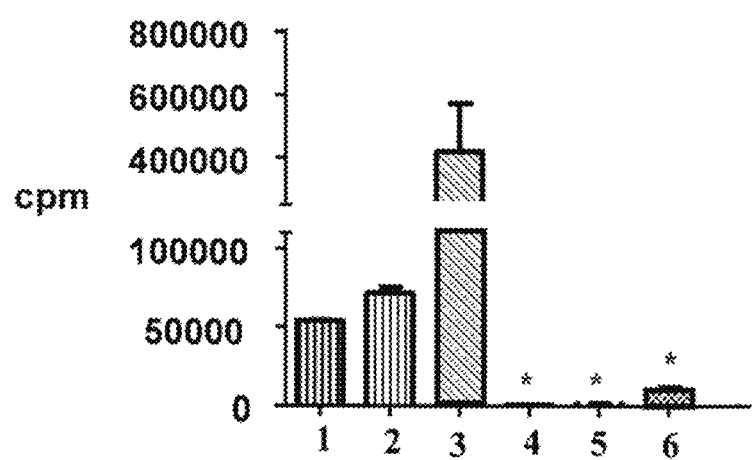

FIG. 4: This figure indicates the levels of proliferation of mouse CD4$^+$ T cells that have been activated with an anti-CD3 (Clone 2C11) antibody in the presence of various proteins including the following: 1) ▦, Fc fragment from a human IgG preparation at 10 μg/ml; 2) ▦, Fc fragment from a human IgG preparation at 2 μg/ml; 3) ▦, a human B7-2:Fc protein (purchased from R & D Biosystems) at 0.5 μg/ml; 4) ■, mouse BTNL2.Fc fusion protein at 5 μg/ml; 5) ▦, human BTNL9.Fc at 10 μg/ml; and 6) ▦, human BTNL9.Fc at 2 μg/ml. Asterisks over lanes 4-6 indicate that these results are significantly lower than the results of the control assays. Methods are described in Example 3.

Figure 5:
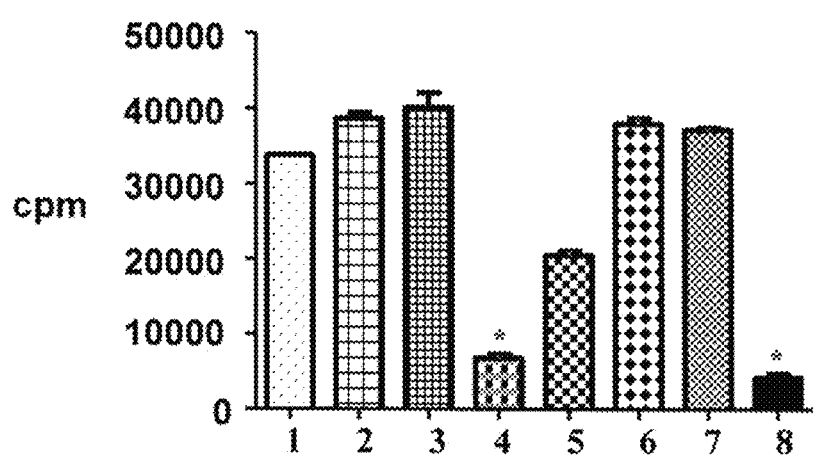
Figure 6A:
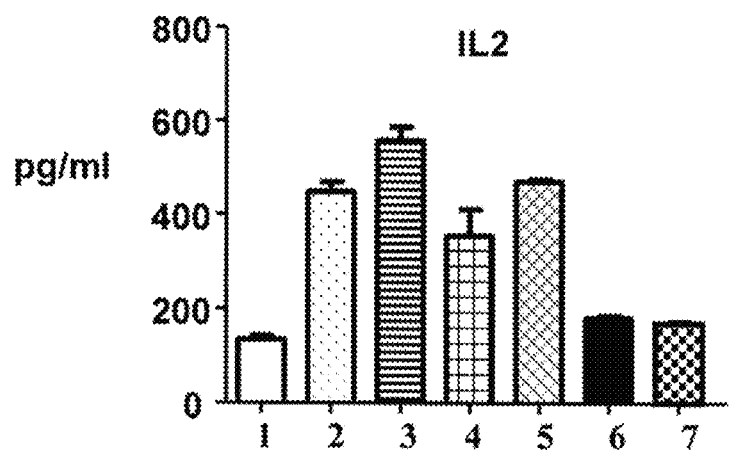
Figure 6B:
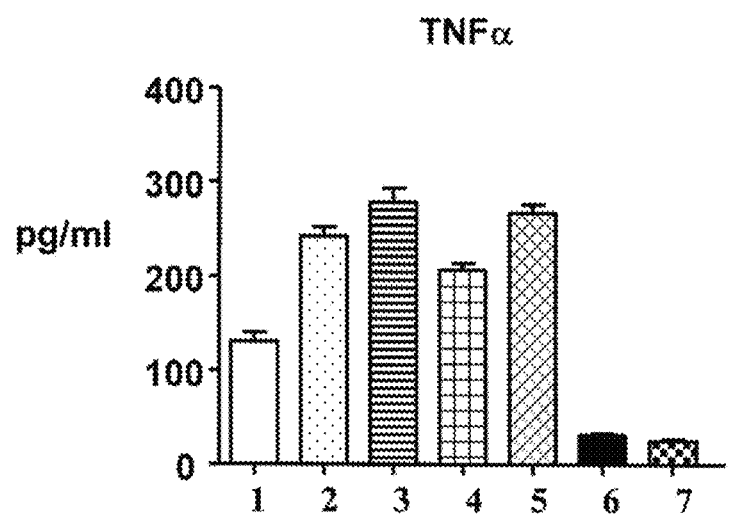
Figure 6C:
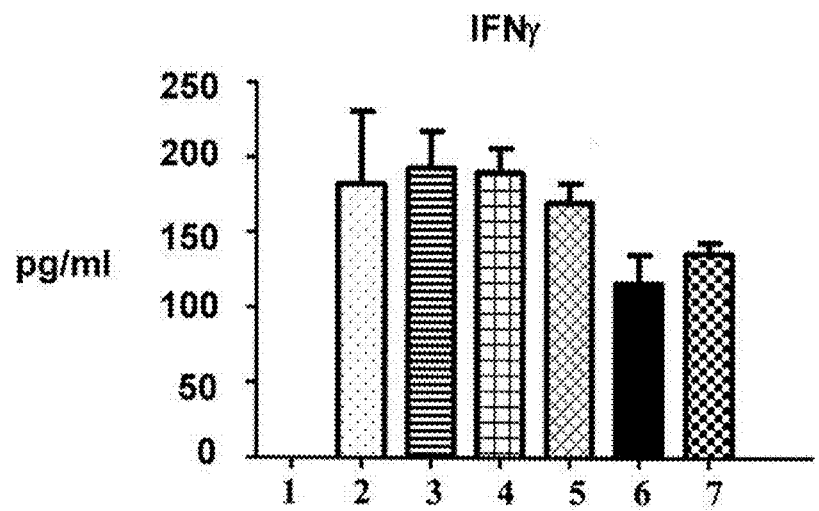
Figure 6D:
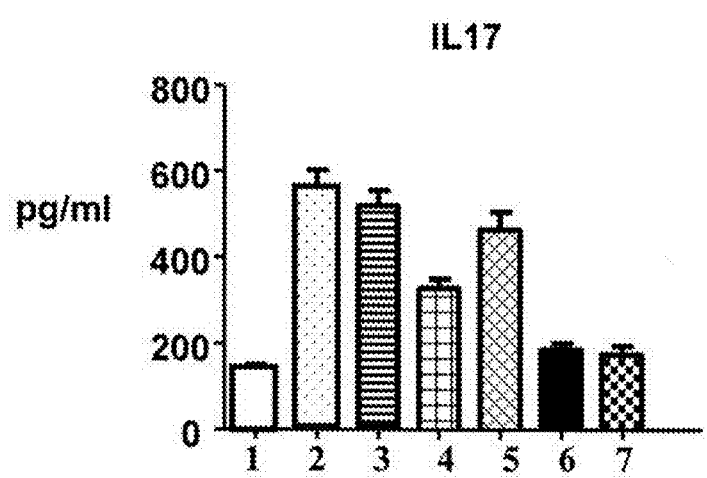
Figure 6E:
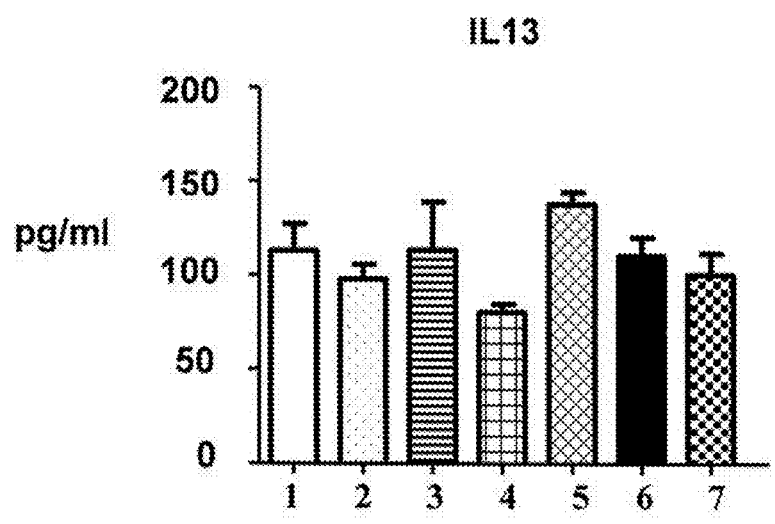

FIG. 5: This figure indicates levels of proliferation of human CD4$^+$ T cells that have been activated with an anti-CD3 antibody in the presence of various proteins including the following: (1) ▦, no additional protein; (2) ▦, an Fc fusion protein known to have no effect of T cell proliferation (p7.5-Fc) at 10 μg/ml; (3) ▦, p7.5-Fc at 2.5 μg/ml; (4) ▦, human BTNL9.Fc at 20 μg/ml; (5) ▦, human BTNL9.Fc at 10 μg/ml; (6) ▦, human BTNL9.Fc at 5 μg/ml; (7) ▦, human BTNL9.Fc at 2.5 μg/ml; and (8) ■, mouse BTNL2.Fc protein at 10 μg/ml. Asterisks over lanes 4 and 8 indicate that these data are significantly different from those of the control assay represented in lane 2. Methods are described in Example 4.

FIGS. 6A-6E: FIGS. 6A-6E show the levels of production of various cytokines by human CD4$^+$ T cells in the presence or absence of an anti-CD3 antibody and various additional proteins. Panels 6A, 6B, 6C, 6D, and 6E show the levels of interleukin-2, tumor necrosis factor-α, interferon-γ, interleukin-17, and interleukin-13, respectively, as indicated. The lanes in the bar graphs in panels 6A-6E result from assays containing the following: 1) ▢, cells without anti-CD3 antibody; 2) ▦, cells with anti-CD3 antibody but no additional protein; 3) ▦, cells with anti-CD3 antibody and a preparation of human IgG; 4) ▦, cells with anti-CD3 antibody plus the p7.5-Fc fusion protein; 5) ▦, cells with anti-CD3 antibody and the HB15-Fc fusion protein, which is known to have no effect on T cell proliferation; 6) ■, cells with anti-CD3 antibody and the mouse BTNL2.Fc protein; and 7) ▦, cells with anti-CD3 antibody and human BTNL9.Fc protein. Methods are described in Example 5.

Figure 7A:
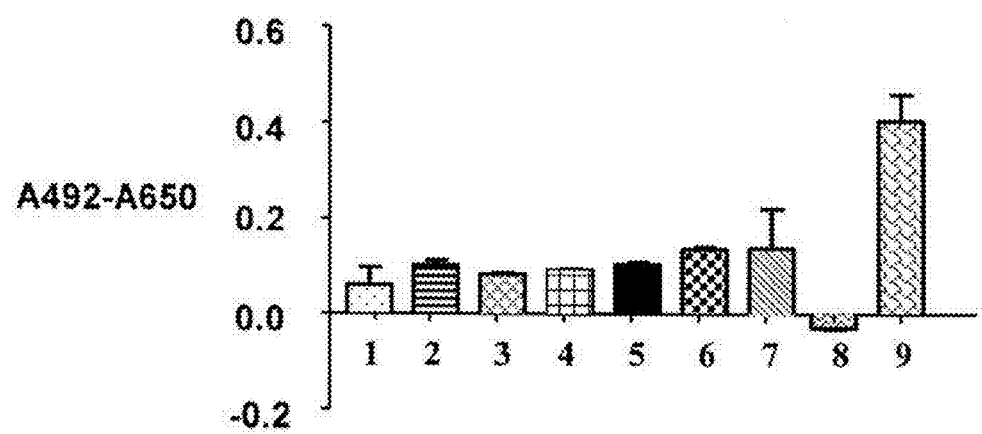
Figure 7B:
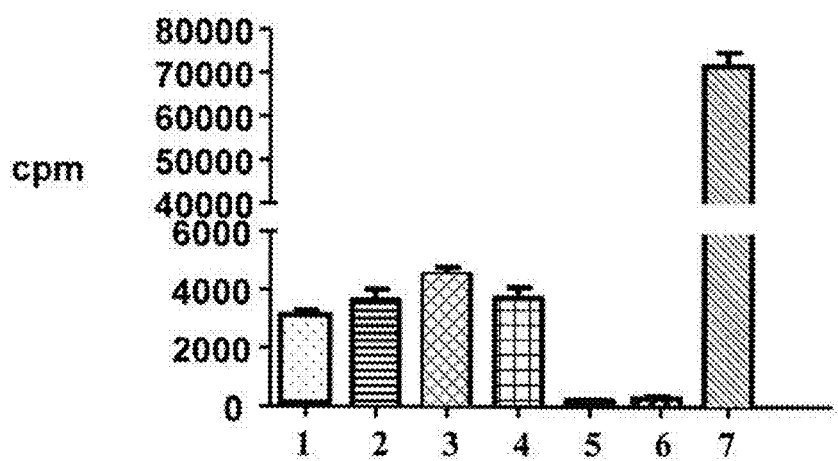

FIGS. 7A-7B: This figure shows the results of assays to measure cell death by measuring release of lactate dehydrogenase (LDH), as explained in detail in Example 7. Panel 7A shows the results of the LDH assay, and panel 7B shown the results of a proliferation assay done with the same cells. The cells in these assays are mouse CD4$^+$ T cells. The various lanes in panels 7A and 7B show the results of assays with or without activated T cells, and with or without additional ingredients, as follows: (1) ▦, T cells with an anti-CD3 antibody; (2) ▦, T cells with the anti-CD3 antibody plus a preparation of human IgG; (3) ▦, T cells with the anti-CD3 antibody plus HB15-Fc; (4) ▦, T cells with the anti-CD3 antibody plus p7.5-Fc; (5) ■, T cells with the anti-CD3 antibody plus mouse BTNL2.Fc; (6) ▦, T cells with the anti-CD3 antibody plus BTNL9.Fc; and (7) ▦, T cells with the anti-CD3 antibody plus murine B7-1-Fc. In panel 7A, lane (8) shows data from an LDH assay done with medium without T cells, and lane (9) shows data from an assay done with T cells plus triton X-100, which is a positive control representing 100% cells death.

Figure 8:
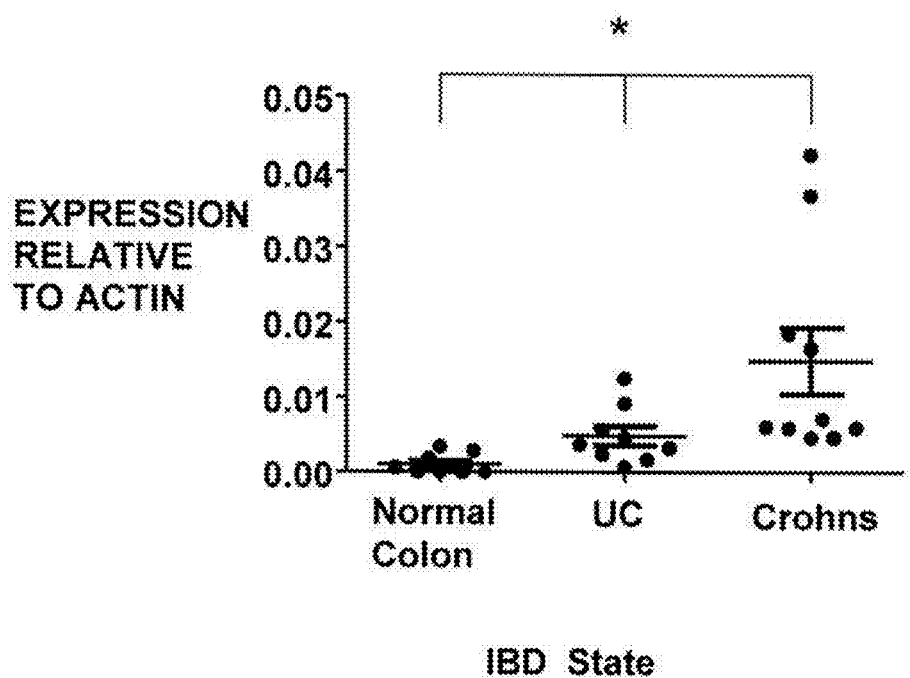

FIG. 8: This figure shows the levels of expression of BTNL9 mRNA in colon tissues from normal donors and from donors having ulcerative colitis (UC) or Crohn's disease (Crohns), as indicated. Each point represents data from one donor. The difference in expression between normal and diseased tissue was statistically significant for both UC and Crohns tissue, as indicated by the asterisk.

Figure 9:
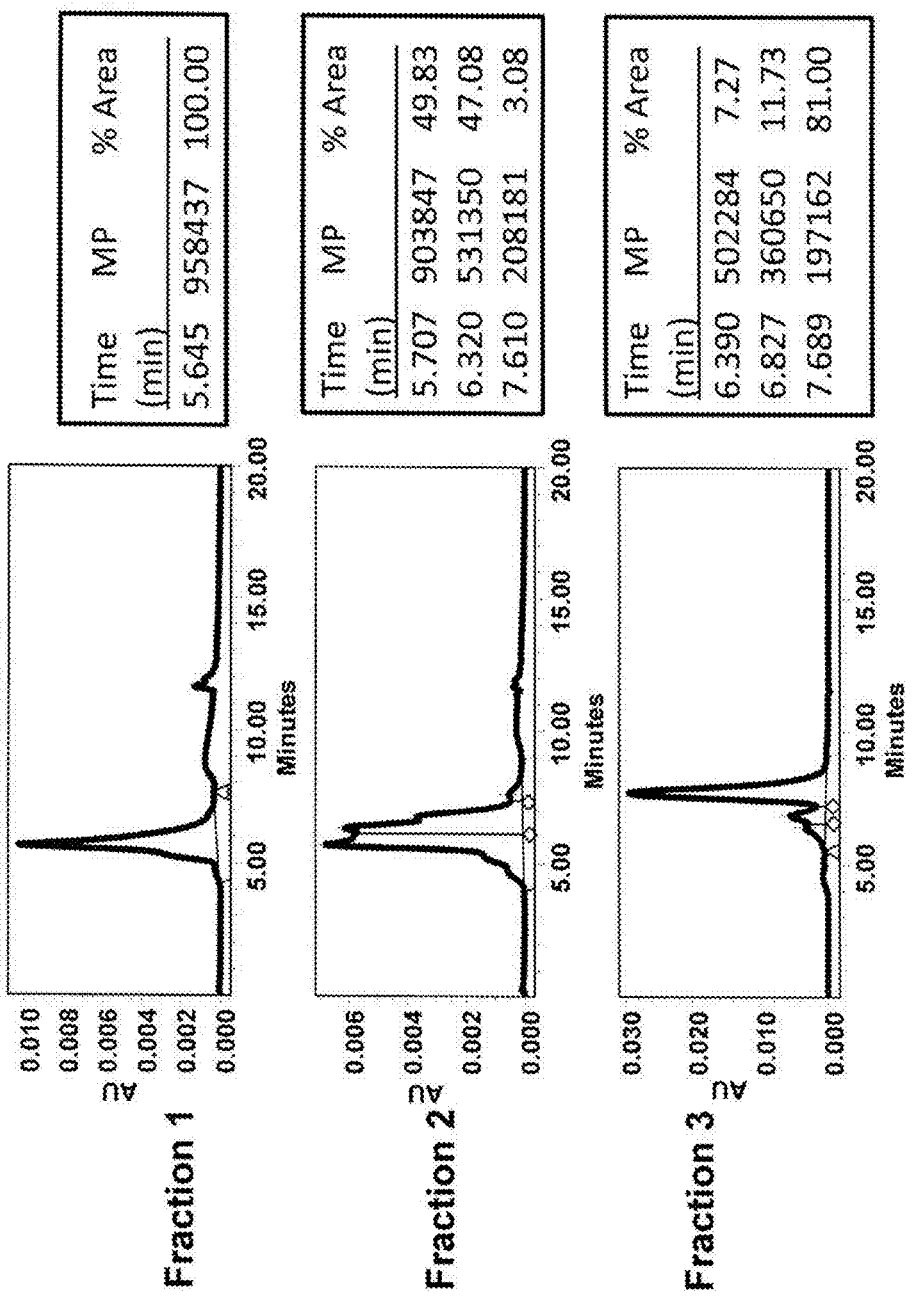

FIG. 9: This figure shows analytic size exclusion chromatography (SEC) analysis of the pooled fractions resulting from SEC purification.

Figure 10:
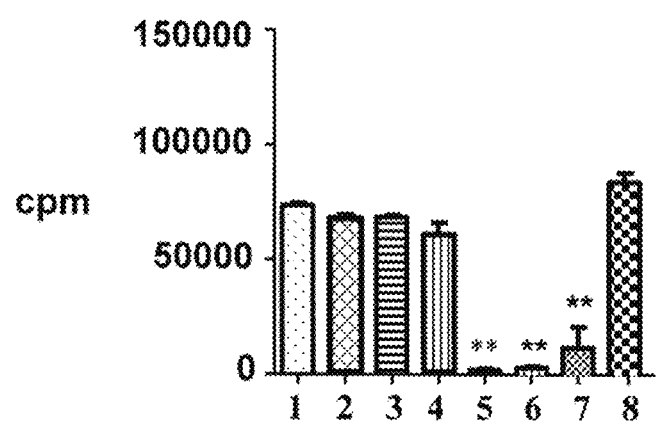

FIG. 10: This figure shows the levels of mouse CD4$^+$ T cell proliferation in response to anti-CD3 antibody, with or without additional proteins, indicated as follows: (1) ▦, with only anti-CD3 antibody; (2) ▦, with anti-CD3 antibody plus HB15-Fc; (3) ▦, with the anti-CD3 antibody plus a preparation of human IgG; (4) ▦, with the anti-CD3 antibody plus Fc fragment from a preparation of human IgG; (5) ■, with the anti-CD3 antibody plus mouse BTNL2.Fc; (6) ▦, with the anti-CD3 antibody plus BTNL9.Fc fraction 1; (7) ▦, with the anti-CD3 antibody plus BTNL9.Fc fraction 2; and (8) ▦, with the anti-CD3 antibody plus BTNL9.Fc fraction 3. Double asterisks indicate a significant difference from control values. Procedures are described in Example 9.

Figure 11:
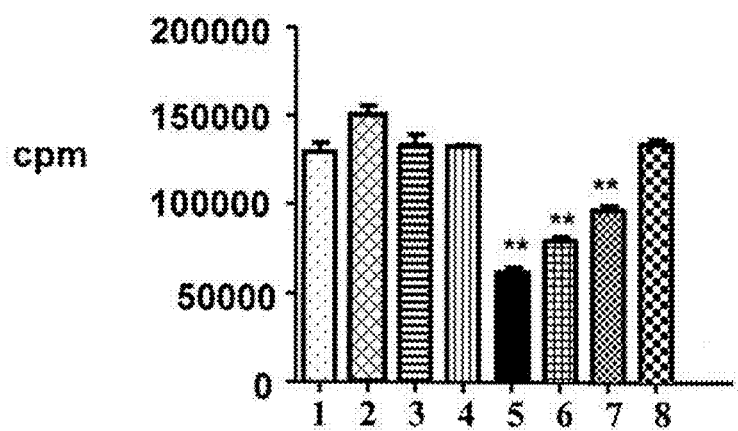

FIG. 11: This figure shows levels of human CD4$^+$ T cell proliferation in the presence of an anti-CD3 antibody, with or without various additional proteins. Lane markings are the same as those in FIG. 10. Procedures are described in Example 9.

Figure 12:
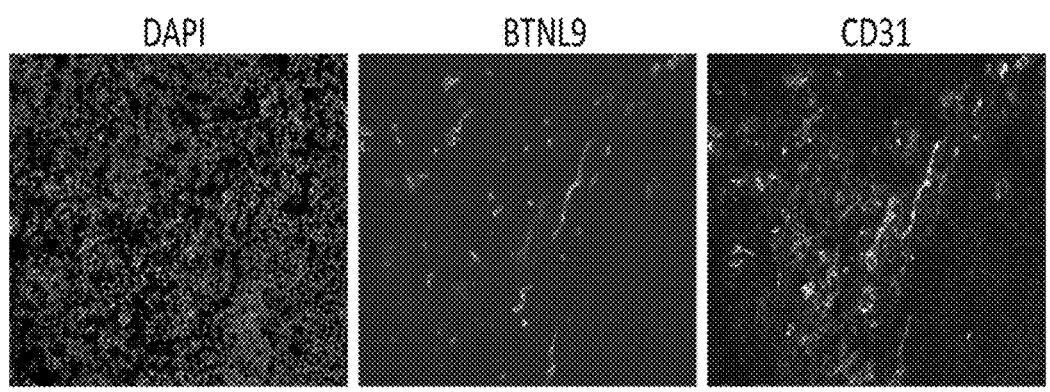

FIG. 12: As explained in Example 10, this figure shows human spleen tissue stained with DAPI (left), an anti-BTNL9 antibody (middle), and CD31 (right).

BRIEF DESCRIPTION OF THE SEQUENCE LISTING

SEQ ID NO:1: Nucleotide sequence of a cDNA encoding the full length human BTNL9 protein as disclosed in NCBI Reference Sequence NM_152547.4.

SEQ ID NO:2: full length amino acid sequence of human BTNL9, which is a translation of the nucleotide sequence of NCBI Reference Sequence NM_152547.4.

SEQ ID NO:3: Amino acid sequence of an IgK signal sequence.

SEQ ID NO:4: Amino acid sequence of a signal sequence for human growth hormone.

SEQ ID NO:5: Nucleotide sequence of a cDNA encoding the full length mouse BTNL9 protein as disclosed in NCBI Reference Sequence NM_172793.2.

SEQ ID NO:6: Full length amino acid sequence of mouse BTNL9, which is a translation of the nucleotide sequence disclosed in NCBI Reference Sequence No. NM_172793.2.

SED ID NO:7: Full length nucleotide sequence of alternatively spliced human BTNL9 cDNA as disclosed by NCBI Reference Sequence BC062459.1

SEQ ID NO:8: Full length amino acid sequence of an alternatively spliced human BTNL9, which is a translation of the nucleotide sequence of NCBI Reference Sequence BC062459.1.

SEQ ID NO:9: Amino acid sequence of a linker.
SEQ ID NO:10: Amino acid sequence of a linker.
SEQ ID NO:11: Amino acid sequence of a linker.
SEQ ID NO:12: Amino acid sequence of a linker.
SEQ ID NO:13: Amino acid sequence of a linker.
SEQ ID NO:14: Amino acid sequence of a linker.
SEQ ID NO:15: Amino acid sequence of a linker.
SEQ ID NO:16: Amino acid sequence of a linker.
SEQ ID NO:17: Amino acid sequence of a linker.
SEQ ID NO:18: Nucleotide sequence encoding a fusion protein (BTNL9.Fc) comprising the extracellular region of human BTNL9, a linker, and an Fc region.
SEQ ID NO:19: Amino acid sequence of BTNL9.Fc.
SEQ ID NO:20: Nucleotide sequence encoding a BTNL2.Fc fusion protein containing the extracellular region of murine BTNL2 and a human IgG Fc region.
SEQ ID NO:21: Amino acid sequence of the BTNL2.Fc encoded by SEQ ID NO:20.

DETAILED DESCRIPTION

The invention provides uses for BTNL9 proteins or inhibitors or agonists of a BTNL9 protein, such as anti-BTNL9 antibodies and/or variant forms of a BTNL9 protein. The invention provides BTNL9 proteins, including variants thereof, and uses for such proteins, as well as nucleic acids encoding all of the above. BTNL9 proteins can alter T cell function by attenuating T cell activation, proliferation, and cytokine production. Such effects can lead to effective treatments of T cell-mediated autoimmune or inflammatory diseases such as inflammatory bowel diseases and fibrotic disorders, among a number of others. Inhibitors of BTNL9 can function to prevent BTNL9 from attenuating T cell activation, proliferation, and cytokine secretion, thus, leading to an overall increase in T cell activation. Such effects can be useful for treating diseases such as cancer or for enhancing the efficacy of a vaccine. Agonists of BTNL9 may be able to alter immune cell function, for example, by altering the activation status of B cells, which express the BTNL9 protein.

Definitions

An "antibody," as meant herein, comprises a heavy chain variable region of an immunoglobulin and/or a light chain variable region of an immunoglobulin. An antibody may be a full length, tetrameric antibody comprising a light chain variable region ($V_L$), a light chain constant region ($C_L$), a heavy chain variable region ($V_H$), a first heavy chain constant region ($C_H1$), a hinge region, a second heavy chain, constant region ($C_H2$), and a third heavy chain constant region ($C_H3$), such as an IgG, IgA, IgD, IgM, or IgE antibody. Alternatively, an antibody can be a fragment such as a Fab fragment or, optionally, a recombinant fragment, such as an scFv fragment. Single domain antibodies comprising a single variable region, either a $V_H$ or $V_L$ region, are also antibodies as meant herein. Single domain antibodies are described in US Patent Appln. Publication US 2006/0062784, the portions of which describe single domain antibodies are hereby incorporated by reference. Further, various forms of monovalent (including single chain antibodies such as scFvs, Fabs, scFv-Fcs, domain antibodies, and various formats described, for example, in International Application WO 2009/089004 and U.S. Pat. No. 5,837,821, the descriptive portions of which are incorporated herein by reference) and multivalent molecules (such as F(ab)$_2$'s and those described, for example, in International Application WO 2009/089004 and U.S. Pat. No. 5,837,821, the descriptive portions of which are incorporated herein by reference) are encompassed within the meaning of "antibody."

It is said in multiple places herein that a multimeric species of a protein has a molecular weight "at least about" four, five, six, seven, eight, nine, ten, eleven, twelve, thirteen, fourteen, fifteen, or sixteen times that of a monomeric species of the protein. While the meaning of this is plain, this phrase is specifically meant to include species that are about four, five, six, etc. times larger than a monomer and not only combinations of such species with larger species. Similarly, it is said in multiple places that a multimer is "at least" a trimer, a tetramer, etc. This phrase is specifically meant to include species that are trimers, tetramers, etc. and not only the combination of the stated species with larger species.

"BTNL9 proteins," as meant herein, includes full length human, BTNL9 proteins and fragments and/or variants thereof, which includes proteins encoded by naturally-occurring allelic variants of the BTNL9 gene, as well as recombinantly-produced BTNL9 proteins, which may contain some sequence changes relative to naturally-occurring BTNL9 proteins.

An "scFv" is a single chain antibody comprising a heavy chain variable region ($V_H$) and a light chain variable region ($V_L$) and not comprising a constant region of an antibody. In some embodiments scFv's can also comprise a linker of variable length between the heavy and Sight chain variable regions. Although an scFv can be fused to other amino acid sequences, the portion of a protein referred to as an scFv preferably does not comprise any substantial amount of amino acid sequence other than a $V_H$ region, a $V_L$ region, and, optionally, a linker joining these sequences.

An "Fc region" or an "Fc portion" or an "Fc fragment" of an antibody (which are considered to be the same herein) is a heavy chain fragment comprising a $C_H2$ and a $C_H3$ domain and a hinge region or a variant of such a fragment. An Fc fragment does not comprise a $C_H1$ domain or a $V_H$ domain. See e.g. Kuby, *Immunology*, Second Edition, p. 110-11, W. H. Freeman and Co., New York (1994). An Fc fragment can be of the IgA, IgD, IgE, IgG, or IgA isotype, including IgG1, , IgG2, IgG3, IgG4 or other subtypes. Variants of Fc regions, as meant herein, may comprise from 1 to 30 (including specifically, no more than 1, 2, 3, 4, 5, 6, 7, 8, 9, 10, etc.) insertions, deletions, or substitutions of a single amino acid relative to a naturally-occurring Fc region. A naturally occurring or "native" Fc region has a sequence that occurs in nature in a living organism, for example, a human or a mouse Fc region. Thus, a "native human" Fc region has an amino acid sequence that is found in a naturally occurring human Fc region. Guidance as to where variations can tolerated without affecting function can be found in the art. For example, alterations of amino acid residues identified in U.S. Pat. No. 5,807,706 and International Application WO 2009/089004, the relevant portions of which are incorporated herein by reference, may be used to encourage heterodimer formation as compared to homodimer formation.

Similarly, alterations to the Fc region that do not prevent binding of the neonatal Fc receptor, FcRn, are encompassed within the alterations that can occur in Fc variants as meant herein. Binding of an Fc region to FcRn can be ascertained at about pH 6 using a Biacore instrument, such as a Biacore 3000. Human FcRn can be coupled to a CM5 chip using standard chemistry. The Fc-containing protein can be part of the mobile phase, and the response can be measured in resonance units. Alterations of Fc regions are described in, for example, International Application WO 97/34631, the relevant portions of which are incorporated herein by reference. Alternatively, comparisons of, for example, IgG sequences within and between species can locate highly conserved amino acids, which would suggest to one of skill in the art that alteration of those amino acids may affect structure and/or function. Numerous alignments of sequences of hinge, $C_H2$ and $C_H3$ regions (which together form the Fc region) are available in, for example, Kabat et al., Sequences of Immunological Interest, National Institutes of Health, Publication No. 91-3242, 1991, the relevant portions of which are incorporated herein by reference. On the other hand, amino acids which vary among various IgGs are sites at which variation is likely to be tolerated without effect on function. Similarly, Fc variants that have other desired properties, such as increased or decreased effector functions, including antibody dependent cellular cytotoxicity and/or Clq binding, which leads to complement fixation, are encompassed within what is meant by Fc variants.

The term "full length antibody" refers to a molecule similar in structure to a naturally-occurring antibody, that is, containing two entire heavy chains and two entire light chains. See e.g. Kabat et al., supra or Kuby, *Immunology*, Second Edition, p. 109-32, W. H. Freeman and Co., New York (1994) for discussion of the structure of naturally-occurring antibodies. The portions of these references describing the structure of full length antibodies are incorporated herein by reference. Also included among "full length antibodies" are antibodies similar in structure to the naturally-occurring dromedary antibodies that contain only two complete heavy chains (often with an unusually long CDR3 region) and no light chains. Muldermans et al. (2001), *J. Biotechnol.* 74:277-302; Desmyter et al. (2001), *J. Biol. Chem.* 276:26285-26290. The portions of these references describing the structure of these dromedary antibodies are incorporated herein by reference.

A "multimeric" protein, such as a multimeric BTNL9 protein, is a protein comprising more than one polypeptide chain. The term "multimer" encompasses terms such as "dimer," "trimer," or "tetramer," which specify exactly how many polypeptide chains the multimer contains. A "homomultimer" consists of two or more copies of the same polypeptide chain and does not contain any different polypeptide chains. Similarly, a "homodimer" consists of two copies of the same polypeptide chain, a "homotrimer" consists of three copies of the same polypeptide chain, etc. A "heteromultimer" contains at least two different polypeptide chains. If the heteromultimer has three or more polypeptide chains, some of them can be identical to each other as long as at least one is different from the others. When a protein is said to be "at least a trimer," it is meant that it is a trimer or a higher order multimer. Similar meanings would be ascribed to "at least a tetramer," "at least a pentamer," etc.

A "Fab fragment" is an antibody fragment comprising a light chain comprising a $V_L$ and $C_L$ region and a portion of a heavy chain comprising a $V_H$ and a $C_H1$ region. A Fab fragment does not comprise a $C_H2$ or $C_H3$ region. See e.g., Kuby, *Immunology*, Second Edition, pp. 110-11 W. H. Freeman and Co., New York (1994) for a discussion of what Fab fragments are. Different kinds of Fab fragments may contain either no hinge region, a portion of a hinge region, or an entire hinge region.

An "scFv-Fc," as used herein, is a recombinant protein that is a fusion of an scFv with an Fc region. See Li et al. (2000), *Cancer Immunol. Immunother.* 49:243-252; Powers et al. (2001), *J. Immunol. Methods* 251:123-135; Gilliland et al. (1996), *Tissue Antigens* 47:1-20.

A "recombinant" protein or antibody is one resulting from the process of genetic engineering. The term "genetic engineering" refers to a recombinant DNA or RNA method used to create a cell that expresses a gene at elevated levels or at lowered levels, or expresses a mutant form of the gene. In other words, the cell has been transfected, transformed or transduced with a recombinant polynucleotide molecule, and thereby altered so as to cause the cell to alter expression of a desired polypeptide.

Soluble secreted proteins and proteins expressed on the cell surface often comprise an N-terminal "signal sequence," which is a hydrophobic sequence that mediates insertion of the protein through the membrane bounding the endoplasmic reticulum (ER) in a eukaryotic cell. Type I transmembrane proteins also comprise signal, sequences. "Signal sequences," as meant herein are amino-terminal hydrophobic sequences which are usually enzymatically removed following the insertion of part or all of the protein through the ER membrane into the lumen of the ER. Thus, it is known in the art that a signal sequence can be present as part of a precursor form of a secreted or transmembrane protein, but will generally be absent from the mature form of the protein. When a protein is said to comprise a signal sequence, it is to be understood that, although a precursor form of the protein does contain the signal sequence, a mature form of the protein will likely not contain the signal sequence. Signal sequences contain a residue adjacent to and immediately upstream from the cleavage site (position-1) and another residue at position-3, which are important for this enzymatic cleavage. Nielsen et al. (1997), *Protein Eng.* 10(1):1-6; von Heijne (1983), *Eur. J. Biochem.* 133:17-21; von Heijne (1985), *J. Mol. Biol.* 184:99-105, the portions of which describe signal sequences and how to identify them are incorporated herein by reference. Signal sequences can be identified as described by Nielsen et al. (supra). Examples of signal peptides or sequences that are functional in mammalian host cells include the following: the signal sequence for interleukin-7 (IL-7) described in U.S. Pat. No. 4,965,195; the signal sequence for interleukin-2 receptor described in Cosman et al. ((1984), *Nature* 312:768); the interleukin-4 receptor signal peptide described in EP Patent 0 367 566; the type I interleukin-1 receptor signal sequence described in U.S. Pat. No. 4,968,607; the type II interleukin-1 receptor signal peptide described in EP Patent 0 460 846; the signal sequence of human IgK (which is METDTLLLWVLLL-WVPGSTG; SEQ ID NO:3); and the signal sequence of human growth hormone (MATGSRTSLLLAFGLLCLP-WLQEGSA; SEQ ID NO:4). The relevant portions of these references are incorporated herein by reference. Many other signal sequences are known in the art.

An "immunoglobulin-like" (Ig-like) domain, as meant herein, is distinguished mainly by its tertiary structure. See e.g. Bork et al. (1994), *J. Mol. Biol.* 242: 309-20; Hunkapiller and Hood (1989), *Adv. Immunol.* 44: 1-63; Williams and Barclay (1988), *Ann. Rev. Immunol.* 6: 381-405. However, variable and constant immunoglobulin-like domains do contain a handful of highly conserved amino acids that occur at conserved positions within their primary amino acid sequence. See e.g. Kabat et al. (1991), Sequences of Proteins of Immunological Interest, U.S. Dept. of Health and Human Services, Public Health Service, National Institutes of Health, NIH Publication No. 91-3242. Such conserved amino acids in variable regions and in $C_H1$ and $C_H2$ constant, regions are discussed in detail in, e.g., Harpaz and Chothia (1994), J. Mol. Biol. 238: 528-39 and Williams and Barclay (1988), Ann. Rev. Immunol. 6: 381-405. The portions of these references that discuss such conserved residues are incorporated herein by reference. The presence of such highly conserved amino acids or conservative variants thereof occurring in the proper spacing can indicate the presence of an IgC-like or IgV-like domain.

The percent identity of two amino acid or two nucleic acid sequences can be determined by comparing sequence information using the computer program GAP, i.e., Genetics Computer Group (GCG: Madison, Wis.) Wisconsin package version 10.0 program, GAP (Devereux et al. (1984), Nucleic Acids Res. 12: 387-95). The preferred default parameters for the GAP program includes: (1) The GCG implementation of a unary comparison matrix (containing a value of 1 for identities and 0 for non-identities) for nucleotides, and the weighted amino acid comparison matrix of Gribskov and Burgess, ((1986) Nucleic Acids Res. 14: 6745) as described in *Atlas of Polypeptide Sequence and Structure*, Schwartz and Dayhoff, eds., National Biomedical Research Foundation, pp. 353-358 (1979) or other comparable comparison matrices; (2) a penalty of 8 for each gap and an additional penalty of 2 for each symbol in each gap for amino acid sequences, or a penalty of 50 for each gap and an additional penalty of 3 for each symbol in each gap for nucleotide sequences: (3) no penalty for end gaps; and (4) no maximum penalty for long gaps.

In connection with comparisons to determine sequence identity of polynucleotides or polypeptides, what is meant by an "alignment window" is the portion of the polynucleotide or polypeptide that is matched, partially or wholly, with another polynucleotide or polypeptide by the computer program GAP (Devereux et al. (1984), Nucleic Acids Res. 12: 387-95) using the parameters stated herein. For example, when a polypeptide of 20 amino acids is aligned with a considerably longer protein and the first 10 amino acids match the longer protein exactly while the last 10 amino acids do not match the longer protein at all, the alignment window is 10 amino acids. If, on the other hand, the first and last amino acids of the 20 amino acid polypeptide match the longer protein, and eight other matches are scattered between, the alignment window is 20 amino acids long. However, long stretches in either aligned strand without identical or conservatively substituted amino acids or identical nucleotides of at least, for example, 25 amino acids or 75 nucleotides constitute an endpoint of an alignment window, as meant herein. Alignment windows for a comparison of sequences can be at least about 25, 50, 60, 75, 80, 90, 100, 150, 200, 225, 300, 400, 450, 500, or 600 amino acids or nucleotides in length.

Two polypeptide or nucleotide sequences are considered "substantially similar" when they are at least 90% identical as determined using the GAP program as described above and have similar biological activity. In the case of the BTNL9, the biological activity to be tested in determining whether two sequences are substantially similar is the ability to inhibit the proliferation of T cells activated by an anti-CD3 antibody.

The BTNL Family

BTNL9 has been placed within the butyrophilin-like (BTNL) family of proteins based on its domain structure. See, e.g., Arnett et al. (2008), Current Immunology Reviews 4: 43-52 and Arnett et al. (2009), Cytokine 46: 370-75. The human proteins in the BTNL family include BTNL2, BTNL3, BTNL8, BTNL9, ERMAP, and MOG, and the domain structures of these proteins are shown diagrammatically in FIG. 1. As is apparent from FIG. 1, BTNL2 is the only member of the family having four immunoglobulin-like (Ig-like) domains in its extracellular region, two IgV-like and two IgC-like domains. MOG and ERMAP each have only one Ig-like domain. BTNL3, BTNL8, and BTNL9 also have one extracellular domain that is clearly an Ig-like domain and another domain that is approximately the right size to be an Ig-like domain, although it is lacking in some of the characteristics of Ig-like domains. All BTNL family members have a transmembrane domain. BTNL2 and MOG have short intracellular regions, whereas BTNL3, BTNL8, BTNL9, and ERMAP have longer intracellular regions containing a B30.2 domain. The function of the intracellular B30.2 is unknown, although mutations in B30.2 domains of some proteins have been, associated with certain diseases. See Henry et al. (1998), Mol. Biol. Evol. 15: 1696-1705, the relevant disclosure of which is incorporated herein by reference. In addition, binding partners for some B30.2 domains have been identified. See, e.g., Jeong et al. (2009), J. Biol. Chem. 284: 22444-22456.

The degree of sequence identify shared by BTNL9 with the other human members of the BTNL family is shown in Table 1 below.

TABLE 1

Percent identity between human members of BTNL family of proteins

|  | BTNL2 | BTNL3 | BTNL8 | ERMAP | MOG |
| --- | --- | --- | --- | --- | --- |
| BTNL9 | 35% | 42% | 43% | 36% | 34% |

Figure 1:
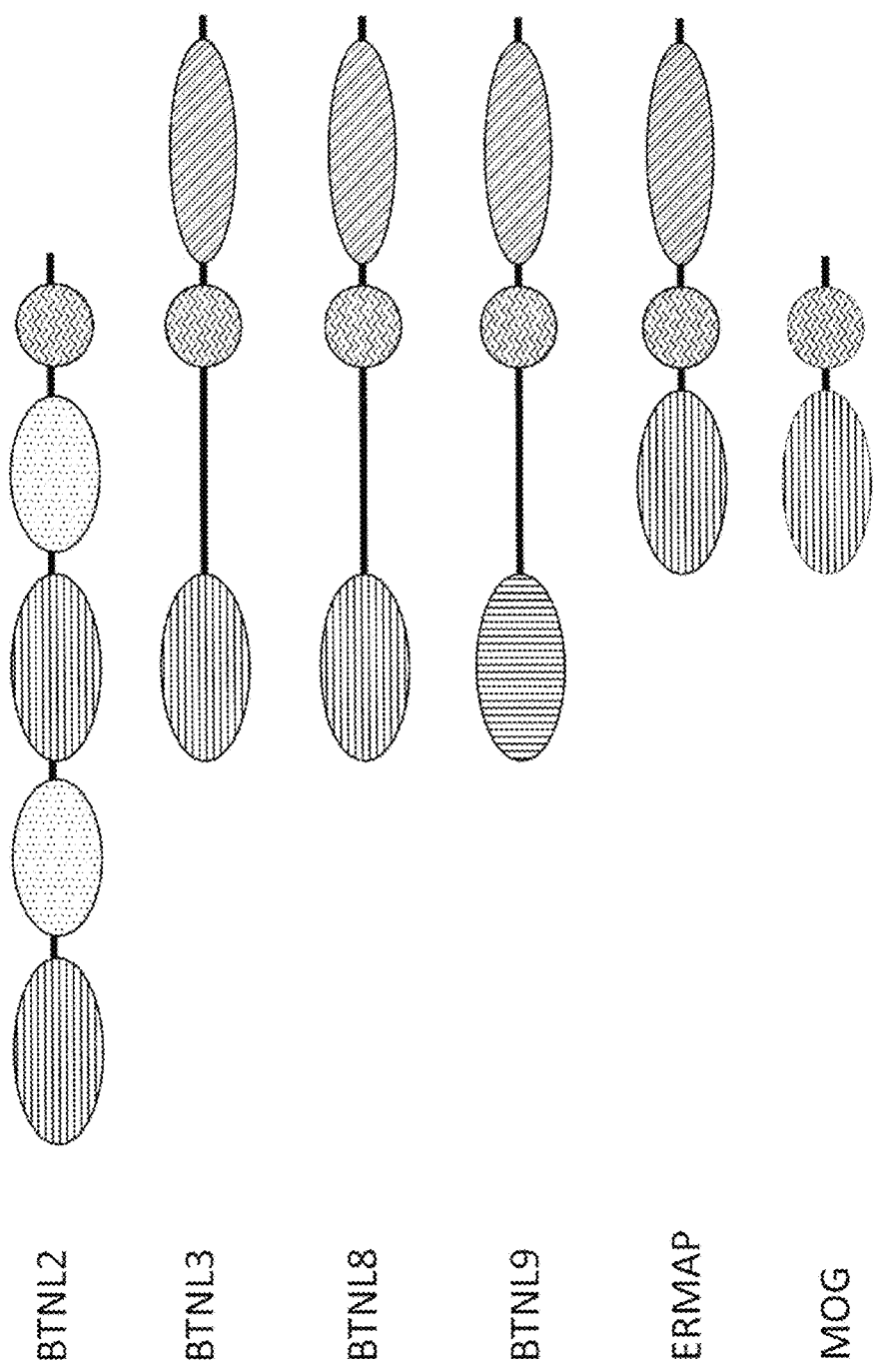
FIG. 1: The domain structures of the human proteins that are part of the butyrophilin-like (BENT) protein family are diagrammed. Each oval or circle represents a protein domain. The domains are indicated as follows: , immunoglobulin variable region-like (IgV-like) domain; , immunoglobulin constant region-like (IgC-like) domain; , immunoglobulin-like (Ig-like) domain; , transmembrane domain; and , B30.2 domain. Regions not identified with a particular domain structure are indicated by a horizontal line.

As shown in FIG. 1, BTNL3, BTNL8, and BTNL9 have similar domain structures. Sequence identity of BTNL9 protein, with BTNL3 and BTNL8 proteins is slightly higher than with the other BTNL proteins. The BTNL3 and BTNL8 proteins are 69% identical to each other.

Beyond levels of sequence identity, certain sites within the BTNL protein family are highly conserved as shown in Table 3 below, which is an alignment of all six human BTNL-like proteins. Beneath the alignment is a consensus sequence. If the consensus amino acid(s) occurs in all proteins in which the amino acid sequence spans the portion of the alignment in which the amino acid occurs, it is shown in bold. If it occurs in all but one of the proteins in which the sequence spans that portion of the alignment, it appears in regular font. If a site has in all cases one of two or more amino acids, each of which are conservative variations of the other, these amino acids are listed below that position in bold font. If a site has in all but one sequence spanning that portion of the alignment one of two or more amino acids, each of which are conservative variations of the other, these amino acids are listed below that position in regular font. The numbering above the alignments in Table 2 is the numbering of SEQ ID NO:2, which is the full length amino acid sequence of human BTNL9, including the signal sequence, which ends at position 34 of SEQ ID NO:2.

TABLE 2

Alignment and consensus sequence of BTNL proteins

```
                                                                   40
BTNL3   ~~~~~~~~~~ ~~~~~~~~~~ ~~~~~~~~~M AFVLILVLSF YELVSGQWQV
BTNL8   ~~~~~~~~~~ ~~~~~~~~~~ ~~~~~~~~~M ALMLSLVLSL LKLGSGQWQV
BTNL9   ~~~~~~~~~~MVDLSVSPDS LKPVSLTSSL VFLMHLLLLQ PGEPSSEVKV
ERMAP   ~~~~~~~~~~ ~~~~MEMASS AGSWLSGCLI PLVFLRLSVH VSGHAGD...
MOG     ~~~~~~~~~~ ~~~~~~MASL SRPSLPSCLC SFLLLLLLQV SSSYAGQFRV
BTNL2   YAEATLVVRN ASAESVSCLV HNPVLTEEKG SVISLPEKLQ TELAS..LKV
ALL                                      L          S    QV
                                         F          A    K
                                         V                R 41                                                        87
BTNL3   TGPGKFVQAL VGEDAVFSCS LFPETSAEAM EVRFFRNQF. ...HAVVHLYR
BTNL8   FGPDKPVQAL VGEDAAFSCF LSPKTNAEAM EVRFERGQF. ...SSVVHLYR
BTNL9   LGPEYPILAL VGEEVEFPCH LWPQLDAQQM EIRWFRSQT. ...FNVVHLYQ
ERMAP   AGKFHV..AL LGGTAELLCP LSLWPGTVPK EVRWLRSPFP QRSQAVHIFR
MOG     IGPRHPIRAL VGDEVELPCR ISPGKNATGM EVGWYRPPF. ...SRVVHLYR
BTNL2   NGPSQPILVR VGEDIQLTCY LSPKANAQSM EVRWDRS... HRYPAVHVYM
ALL         GP   I AL VGEDA F C  L P   A  M EVRW R        VVHLYR
            V V    L DEV L     I     T      I F           AI IFQ
                     I                                          V 88                                                       137
BTNL3   DGEDWESKQM PQYRGRTEFV KDSIAGGRVS LRLKNITPSD IGLYGCWFSS
BTNL8   DGKDQPFMQM PQYQGRTKLV KDSIAEGRIS LRLENITVLD AGLYGCRISS
BTNL9   EQQELPGRQM PAFRNRTKLV KDDIAYGSVV LQLHSIIPSD KGTYGCRFHS
ERMAP   DGKDQDEDLM PEYKGRTVLV RDA.QEGSVT LQILDVRLED QGSYRCLIQV
MOG     NGKDQDGDQA PEYRGRTELL KDAIGEGKVT LRIRNVRFSD EGGFTCFFRD
BTNL2   DGDHVAGEQM AEYRGRTVLV SDAIDEGRLT LQILSARPSD DGQYRCLFEK
ALL      DG D     QM  P YRGRT LV KDSI  G VT LRL  I  D   G Y C  F
         E  E          A FK    FL R A    IS  QI  V              F  I
                          Q                  L       A 138                                                       187
BTNL3   QIYDEEATWE LRVAALGSLP LISIVGYVDG GIQLLCLSSG WFPQPTAKWK
BTNL8   QSYYQKAIWE LQVSALGSVP LISITGYVDR DIQLLCQSSG WFPRPTAKWK
BTNL9   DNFSGEALWE LEVAGLGSDP HLSLEGFKEG GIQLRLRSSG WYPKPKVQWR
ERMAP   GNLSKEDTVI LQVAA....P SV........ .......... GSLSPSA...
MOG     HSYQEEAAME LKVED....P FY........ .......... W.VSPGV...
BTNL2   DDVYQEASLD LKVVGLGSSP LITVEGQEDG EMQPMCSSDG WFPQPHVPWR
ALL              EA  E L V     P                              W   P A
                    D                                             V 188                                                       237
BTNL3   GPQGQDLSSD SRANA.DGYS LYDVEISIIV QENA.GSILC SIHLAEQSHE
BTNL8   GPQGQDLSTD SRTNR.DMHG LFDVEISLTV QENA.GSISC SMRHAHLSRE
BTNL9   DHQGQCLPPE FEAIVWDAQD LFSLETSVVV RAGALSNVSV SIQNLLLSQK
ERMAP   .......... ........VA LAVILPVLVL LIMVCLCLIW KQRRAKEKLL
MOG     .......... ........LV LLAVLPVLLL QITVGLVFLC LQYRLRGKLR
BTNL2   DMEGKTIPSS SQALTQGSHG LFHVQTLLRV TNISAVDVTC SISIPFLGEE
ALL                          LF V   L V         A  I
                             L L    V L         V  V
                             Y I    V I            L
                             A                     F 238                                                       287
BTNL3   VESKVLIGET FFQ.PSPWR. ...LASILLGL LCGALCGVVM ........GM
BTNL8   VESRVQIGDT FFE.PISWH. ...LATKVLGI LCCGLFFGIV ........GL
BTNL9   KELVVQIADV FVPGASAWKS AFVATLPLLL VLAALALGVL RKQRRSREKL
ERMAP   YEHVTEVDNL L......... .......... .......... SDHAKE....
MOG     AE.IENLHRT F......... .......... .......... DPHFLRVPCW
BTNL2   KIATFSLSFS ..RMTFLWK LLVWGLLLAV AVGLPRKRS~ ~~~~~~~~~~
ALL          E    I           ..RMTFLWK
               V
               L 288                                                       337
BTNL3   IIVFFKSK.. .....GKIQA ELDWRRKHGQ AELRDARKHA VEVTLDPETA
BTNL8   KIFFSKFQ.. .....WKIQA ELDWRRKHGQ AELRDARKHA VEVTLDPETA
BTNL9   RKQAEKRQEK LTAELEKLQT EDWRRAEGQ AEWRAAQKVA VDVTLDPASA
ERMAP   KGKLHKAVKK LRSELK.... ...LKRAAAN SGWRRARLHF VAVTLDPDTA
MOG     KITLFVIVPV LGPLVALIIG YNWLHRRLAG QFLEEELFHL EALSG~~~~~
BTNL2   ~~~~~~~~~~ ~~~~~~~~~~ ~~~~~~~~~~ ~~~~~~~~~~ ~~~~~~~~~~
ALL     K   F                 RR    GQ      R AR HA V  VTL
        R   L                       K  AN           LQ L    LS
            A                       H                F
```

TABLE 2-continued

Alignment and consensus sequence of BTNL proteins

```
       338                                                   387
BTNL3  HPKLCVS.DL KTVTHRKAPQ .EVPHSEKRF TRKSVVAS.Q GFQAGKHYWE
BTNL8  HPKLCVS.DL KTVTHRKAPQ .EVPHSEKRF TRKSVVAS.Q SFQAGKHYWE
BTNL9  HPSLEVSEDG KSVSSRGAPP GPAPGHPQRF SEQTCALSLE RFSAGRHYWE
ERMAP  HPKLILSEDQ RCV.RLGDRR QPVPDNPQRF DFVVSILGSE YFTTGCEYWE
MOG    ~~~~~~~~~~ ~~~~~~~~~~ ~~~~~~~~~~ ~~~~~~~~~~ ~~~~~~~~~~
BTNL2  ~~~~~~~~~~ ~~~~~~~~~~ ~~~~~~~~~~ ~~~~~~~~~~ ~~~~~~~~~~
ALL    HPKL VS D  KTV HR APQ  VP    KRF T KS VAS   F AGKHYWE
            L     S   R    R    A       Q  S QT AL       R
                                              I 388                                               436
BTNL3  VDVGQNVGWY VGVCRDDVDR GENNVTLSPN NGYWVLRLTT EHLYFTFNPH
BTNL8  VDGGHNKRWR VGVCRDDVDR RKEYVTLSPD HGYWVLRLNG EHLYFTLNPR
BTNL9  VHVGRRSRWF LGACLAAVPR A.GPARLSPA AGYWVLGLWN GCEYFVLAPH
ERMAP  VYVGDKTKWI LGVCSESVSR .KGKVTASPA NGHWLLRQSR GNEYEALTSP
MOG    ~~~~~~~~~~ ~~~~~~~~~~ ~~~~~~~~~~ ~~~~~~~~~~ ~~~~~~~~~~
BTNL2  ~~~~~~~~~~ ~~~~~~~~~~ ~~~~~~~~~~ ~~~~~~~~~~ ~~~~~~~~~~
ALL    V VGQN RW  VGVC D V R  K  VTLSP  NGYWVLRL   H LF L PH
          HR  K   L  A   E        A A   H          N    F  R
          RK 437                                               485
BTNL3  FISLPPSTPP TRVGVFLDYE GGTISFFNTN DQSLIYTLLT CQFEGLLRPY
BTNL8  FISVFPRTPP TKIGVFLDYE CGTISFFNIN DQSLIYT.LT CRFEGLLRPY
BTNL9  RVALTLRVPP RRLGVFLDYE AGELSFFNVS DGSHIFTFHD .TFSGALCAY
ERMAP  QTSFRLKEPP RCVGIFLDYE AGVISFYNVT NFSHIFTF.T HNFSGPLRPF
MOG    ~~~~~~~~~~ ~~~~~~~~~~ ~~~~~~~~~~ ~~~~~~~~~~ ~~~~~~~~~~
BTNL2  ~~~~~~~~~~ ~~~~~~~~~~ ~~~~~~~~~~ ~~~~~~~~~~ ~~~~~~~~~~
ALL     SL  R PP  RVGVFLDYE  G  ISFFN   DQS IYT  T  QF G LRPY
        V   K     KI I          L  Y    K   F      N        F
        F         L                                R 486                                               526
BTNL3  IQHAMYD.EE KGTPIFICPV SWG~~~~~~~ ~~~~~~~~~~ ~~~~~~~~~~
BTNL8  IEYPSYN.EQ NGTPIVICPV TQESEKEASW QRASAIPETS NSESSSQATT
BTNL9  FRPRAHDGGE HPDPLTICPL P......... VRGTGVPEEN DSDTWLQPYE
ERMAP  FEPCLHDGGK NTAPLVICSE LHKSEESIVP RPEGKGHANG DVSLKVNSSL
MOG    ~~~~~~~~~~ ~~~~~~~~~~ ~~~~~~~~~~ ~~~~~~~~~~ ~~~~~~~~~~
BTNL2  ~~~~~~~~~~ ~~~~~~~~~~ ~~~~~~~~~~ ~~~~~~~~~~ ~~~~~~~~~~

527    535
BTNL3  ~~~~~~~~~~ ~~~~~~~~~~ ~~~~~~~~~~ ~
BTNL8  PFLPRGEM~~ ~~~~~~~~~~ ~~~~~~~~~~ ~
BTNL9  PADPALDWW~ ~~~~~~~~~~ ~~~~~~~~~~ ~
ERMAP  LPPKAPELKD IILSLPPDLG PALQELKAPS F
MOG    ~~~~~~~~~~ ~~~~~~~~~~ ~~~~~~~~~~ ~
BTNL2  ~~~~~~~~~~ ~~~~~~~~~~ ~~~~~~~~~~ ~
```

One of skill in the art will appreciate that the consensus sequence among these proteins reflects features that may be important for the structures or functions of these proteins. Given their varying expression patterns, it is likely that these proteins do not have identical functions, and, thus, it is unlikely that all amino acids important for the function of each protein would be conserved within the family. However, many of the conserved amino acids may be important to maintain the proper structure, which is, of course, necessary for function. At many sites one of two or snore amino acids that are conservative variations of each other occur in all or most members of the BTNL family. One of skill in the art would understand that such conservative variations in BTNL9 would likely not adversely affect function. For example, at position 55 of SEQ ID NO:2 (which has the same numbering as the alignment of Table 2 above), various members of the BTNL family have one of three different hydrophobic amino acids, alanine (BTNL3, BTNL8, and ERMAP), isoleucine (BTNL2), or valine (BTNL9 and MOG). One of skill in the art would understand that a change from valine to alanine or isoleucine at this position of the BTNL9 amino acid sequence would be unlikely to affect function. Similar considerations would apply at all of the sites where conservative variations occur within the family. Thus, a BTNL9 protein, as meant herein, includes proteins comprising SEQ ID NO:2, or a fragment thereof, wherein the sequence may be altered by conservative variation at a site where conservative variation occurs among members of the BTNL family and wherein the protein can inhibit the proliferation of T cells as measured by the method described in the examples below. Such sites include positions 47, 49, 51, 53, 54, 55, 57, 61, 67, 72, 74, 82, 83, 85, 86, 87, 88, 91, 98, 100, 101, 106, 107, 108, 116, 117, 119, 120, 123, 131, 135, 147, 184, 209, 211, 215, 217, 221, 225, 244, 288, 291, 312, 316, 317, 323, 324, 327, 330, 331, 343, 349, 352, 357, 360, 365, 368, 370, 371, 373, 374, 383, 392, 393, 395, 398, 400, 403, 411, 413, 417, 428, 433, 436, 440, 443, 448, 449, 451, 460, 463, 468, 472, 477, and 485 of SEQ ID NO:2. Further, variations may also be tolerated at other sites within BTNL9 without effect on function. For example conservative substitutions at non-conserved positions would be unlikely to affect function, although functional effects are possible as such sites.

Thus, a BTNL9 protein, as meant herein, includes proteins that (1) have naturally-occurring polymorphisms or recombinantly-introduced amino acid changes, (2) are at least 90%, 95%, 96%, 97%, 98% or 99% identical to SEQ ID NO:2 and/or to amino acids 35-257 of SEQ ID NO:2, and (3) retain the ability to attenuate T cell proliferation as measured by the methods described herein or act as an inhibitor of native BTNL9. Some such polymorphisms may enhance the ability of a BTNL9 protein to inhibit T cell proliferation and/or may make a BTNL9 protein easier to produce in a commercial production process. Other such polymorphisms may produce an inhibitor of native BTNL9. These polymorphisms can occur at sites within BTNL9 that are not conserved such as, for example, position 41, 44, 45, 46, 48, 56, 58, 60, and any other site shown to be nonconserved in Table 2.

The expression patterns and biological functions of the BTNL proteins have been explored to some extent in some cases, but not in others. ERMAP is expressed on the surface of red blood cells and has not been assigned a specific biological function. MOG is a component of the myelin sheath. Neither ERMAP nor MOG is thought to play a role in the immune system, although antibodies to MOG are often detected in patients with multiple sclerosis. BTN1 is homologous to MOG, and BTN1 is found in cow's milk. It has been hypothesized that human consumption of cow's milk may lead to the development of antibodies to BTN1 that cross-react with human MOG, thus leading to autoimmune diseases such as multiple sclerosis. See Guggenmos et al. (2004), J. Immunol. 172: 61-68. BTNL2 has been shown to inhibit T cell proliferation and cytokine secretion, but not B cell proliferation. Thus, BTNL2 is thought to act as a negative co-regulator of T-cell mediated events. See, e.g., U.S. Pat. No. 7,244,822, the relevant portions of which are incorporated herein by reference. A polymorphism in BTNL2 has been clearly linked to sarcoidosis, suggesting that BTNL2 may play a role in either initiating or mediating or contributing or responding to this disease. Valentonyte et al. (2005), Nature Genetics 37(4): 357-64. More tentative associations have been drawn between various BTNL2 polymorphisms and ulcerative colitis, rheumatoid arthritis, spontaneous inclusion body myositis, systemic lupus erythematosus, type I diabetes, tuberculoid leprosy, and antigen-specific IgE responsiveness. Arnett et al. (2009), Cytokine 46: 370-75. BTNL3, 8, and 9 have not been assigned any specific biologic function.

Levels of RNAs encoding the various BTNL proteins in various cell types and tissues have been reported. BTNL9 RNA is relatively highly expressed in adipose tissue, lung, thymus, spleen, and heart. Other BTNL family members have different expression patterns, and in all but one, RNA expression has been detected in hematopoietic-lineage cells. Arnett et al. (2009), Cytokine 46: 370-75. Among various cell types associated with immune function that have been tested for BTNL9 expression. BTNL9 RNA is expressed predominantly in B cells. Arnett et al. (2009), Cytokine 46: 370-75. The expression of BTNL9 RNA in cells involved in immune function suggests that BTNL9 may play a role in immune function, either by driving the inflammatory response or in dampening the response following a flare.

BTNL9 Protein

The instant invention encompasses secreted, soluble versions of BTNL9, as well as versions comprising a transmembrane domain that can be expressed on a cell surface. Such proteins can be isolated, that is, be part of a purified protein preparation in which the BTNL9 protein constitutes at least 80% or at least 90% of the protein present in the preparation. The invention further includes BTNL9 proteins encoded by the BTNL9 nucleic acids described below. A BTNL9 protein, as meant herein, encompasses a protein comprising the amino acid sequence of SEQ ID NO:2, as well as fragments, derivatives, and variants thereof, including fusion proteins and multimers, as discussed above and below. The amino acid sequence of SEQ ID NO:2, includes a signal sequence starting at position 1 and ending at a position from about position 29 to about position 38, optionally at position 34. Thus, the amino acid sequence of the mature BTNL9 begins at a position from about 30 to about position 39 of SEQ ID NO:2. Optionally, the mature amino acid sequence of BTNL9 begins at position 35 of SEQ ID NO:2.

The signal sequence of BTNL9 is followed by an Ig-like domain extending from about position 44 to about position 150 of SEQ ID NO:2. The following region, from about position 151 to about position 257 of SEQ ID NO:2, aligns with IgC-like domains in BTNL2, but lacks some of the characteristic sequence features commonly found in a IgCl-like domain. See, e.g., Williams and Barclay (1988), Ann. Rev. Immunol. 6: 381-405: Peach et al. (1995), J. Biol. Chem. 270(36): 21181-21187. The transmembrane domain of BTNL9 begins at about position 258 of SEQ ID NO:2 and ends at about position 277 of SEQ ID NO:2. The intracellular portion of BTNL9 begins at about position 278 and ends at position 535 of SEQ ID NO:2. The intracellular region contains a B30.2 domain extending from about position 328 to about position 486 of SEQ ID NO:2. A B30.2 domain is a globular domain of approximately 170 amino acids. Henry et al. discuss B30.2 domains in some detail and provide an alignment of a number of B30.2 domains and a consensus sequence derived from the alignment. The portions of Henry et al. (1998), Mol. Biol. Evol. 15(12): 1696-1705 that show (by sequence comparison) and explain what a B30.2 domain is are incorporated herein by reference. B30.2 domains are also found in BTNL3, BTNL8, and ERMAP, all of which are members of the butyrophilin-like family of proteins, as discussed herein. The alignment of BTNL proteins in Table 2 above from about position 328-486 exhibits a high degree of homology, certainly higher than is observed between the more disparate collection of proteins containing B30.2 domains aligned by Henry et al. supra.

BTNL9 proteins, as meant herein, include hetero- and homo-multimers comprising at least two BTNL9 proteins. In some embodiments, biologically active multimers can be homomultimers. The size of such homomultimers can be determined by polyacrylamide gel electrophoresis under non-reducing conditions or by size exclusion chromatography. The size of the monomeric BTNL9 protein contained in such multimers can be determined by polyacrylamide gel electrophoresis of the multimer under reducing conditions. Such conditions would be expected to break disulfide bridges and interfere with non-covalent interactions such as hydrogen bonds or charge interactions. Thus, multimers held together by disulfide bonds or non-covalent interactions would be expected to be reduced to monomers under reducing conditions. In some embodiments, the size of the biologically active BTNL9 homomultimer can be at least four, five, six, seven, eight, nine, ten, eleven, twelve, thirteen, fourteen, fifteen or sixteen times the size of the monomeric BTNL9 protein.

BTNL9 proteins, as meant herein, also include proteins encoded by splice variants of the full length BTNL9 mRNA.

The full length cDNA encoding BTNL9 (SEQ ID NO:1) contains eleven exons, which occur at the following positions in SEQ ID NO:1: exon 1, position 1-208; exon 2, position 209-340; exon 3, position 341-685; exon 4, position 686-976; exon 5, position 968-1084; exon 6, position 1085-1117; exon 7, position 1118-1138; exon 8, position 1139-1159; exon 9, position 1160-1186; exon 10, position 1587-1213; and exon 11, position 1214-3500.

The coding sequence extends from position 232-1839 of SEQ ID NO:1, the last three nucleotides being a stop codon. Thus, the coding sequence starts within the second exon. The end of the second exon extends slightly beyond the end of the nucleotide sequence encoding the signal sequence of BTNL9 at about position 34 of SEQ ID NO:2. The third exon encodes amino acids from about position 37 to about position 151 of SEQ ID NO:2, including the Ig-like domain. The fourth exon encodes the portion of SEQ ID NO:2 from about position 152 to about position 245, in other words most of the following domain, which has some of the features of an IgCl-like domain. Following this are exons 5-10, all of which are relatively short. Exon 5 encodes the remainder of the extracellular domain plus the transmembrane domain, from about position 246 to about position 284 of SEQ ID NO:2. Exons 6-10 together encode about forty three amino acids, from about position 285 to about position 327 of SEQ ID NO:2. Exon 11 encodes the B30.2 domain, which extends from about position 328 to about position 486 of SEQ ID NO:2, and the remainder of the protein, ending at position 535 of SEQ ID NO:2.

BTNL9 proteins, as meant herein, can be encoded by splice variants that are missing any one, two, three, four, five, six, seven, eight, or nine exons. For example, a BTNL9 protein can be encoded by a splice variant that is missing exon 3 or exon 4. A resulting BTNL9 protein can contain the Ig-like domain from about position 37 to about position 151 of SEQ ID NO:2, but not the following domain from about position 152 to about position 245 of SEQ ID NO:2. Alternatively, a resulting BTNL9 protein can contain amino acids from about position 152 to about position 245 of SEQ ID NO:2, but not amino acids from about position 37 to about position 151 of SEQ ID NO:2. A BTNL9 protein encoded by a splice variant transcript missing exons 10 and 11 would lack amino acids extending from about 319 to 535 of SEQ ID NO:2, although these amino acids would likely be replaced by other amino acids encoded by the intron following exon 9. Such a BTNL9 transcript lacking exons 10 and 11 has been reported in GenBank submission number BC062459.1, the sequence of which is given in SEQ ID NO:7. This splice variant apparently utilizes cryptic splice sites found in the introns. SEQ ID NO:8 is amino acid sequence encoded by SEQ ID NO:7. Other BTNL9 proteins can be encoded by splice variants lacking exon 3, 4, 5, 6, 7, 8, 9, 10, or 11 or any combination of these exons. Splice variants can, in addition use cryptic splice sites.

In some embodiments, a BTNL9 protein can be a soluble fragment of the full length transmembrane protein comprising SEQ ID NO:2, or a variant thereof. In some embodiments, a BTNL9 protein comprises a fragment of BTNL9 comprising the immunoglobulin-like domain extending from residue 40, 41, 42, 43, 44, 45, 46, 47, 48, 49, or 50 of SEQ ID NO:2 to residue 140, 141, 142, 143, 144, 145, 146, 147, 148, 149, or 150 of SEQ ID NO:2. Such embodiments may or may not include the following domain extending from residue 141, 142, 143, 144, 145, 146, 147, 148, 149, 150, 151, 152, 153, 154, 155, 156, 157, 158, 159, or 160 of SEQ ID NO:2 to residue 248, 249, 250, 251, 252, 253, 254, 255, 256, 257, 258, 259, or 260 of SEQ ID NO:2. In further embodiments, a BTNL9 protein can comprise a fragment extending from residue 141, 142, 143, 144, 145, 146, 147, 148, 149, 150, 151, 152, 153, 154, 155, 156, 157, 158, 159, or 160 of SEQ ID NO:2 to residue 248, 249, 250, 251, 252, 253, 254, 255, 256, 257, 258, 259, or 260 of SEQ ID NO:2. Such embodiments may or may not include the preceding domain extending from residue 40, 41, 42, 43, 44, 45, 46, 47, 48, 49, or 50 of SEQ ID NO:2 to residue 140, 141, 142, 143, 144, 145, 146, 147, 148, 149, or 150 of SEQ ID NO:2. A BTNL9 protein can comprise a fragment which includes most or all of the extracellular region of BTNL9. Such a protein can comprise an amino acid sequence extending from residue 30, 31, 32, 33, 34, 35, 36, 37, 38, 39, or 40 of SEQ ID NO:2 to residue 248, 249, 250, 251, 252, 253, 254, 255, 256, 257, 258, 259, or 260 of SEQ ID NO:2, optionally from about residue 37 to about residue 257 of SEQ ID NO:2. All of these fragments can contain variations relative to SEQ ID NO:2 and can contain a defined number of substitutions, insertions, or deletions of a single amino acid relative to SEQ ID NO:2 as discussed below. All of these embodiments can inhibit the proliferation of T cells stimulated by an anti-CD3 antibody.

The invention encompasses epitopes of BTNL9 proteins that are useful for generating antibodies, which are referred to herein as immunogenic fragments. Immunogenic fragments are preferably at least 10 amino acids long and can comprise contiguous amino acids from SEQ ID NO:2. Such epitopes can span regions of a BTNL9 protein encoded by a splice junction, which may have the advantage of specific binding to proteins encoded by specific splice variants. In some embodiments the epitope is located within the extracellular region of BTNL9, from amino acid position 35-257 of SEQ ID NO:2. The epitope can be within the immunoglobulin-like domain extending from about amino acid position 44-150 of SEQ ID NO:2 or within the following domain, which extends from about amino acid position 151-257 of SEQ ID NO:2.

A BTNL9 protein, as meant herein, may contain one or more insertions, deletions, or substitutions of a single amino acid relative to SEQ ID NO:2 or to one of the fragments of SEQ ID NO:2 discussed above. In some embodiments, a BTNL9 protein contains not more than 20, 19, 18, 17, 16, 15, 14, 13, 12, 11, 10, 9, 8, 7, 6, 5, 4, 3, 2, or 1 substitutions, insertions, or deletions of a single amino acid relative to SEQ ID NO:2 or relative to one of the fragments of SEQ ID NO:2 discussed above. AH such BTNL9 protein variants within the scope of the invention retain the ability to attenuate T cell proliferation or can act as an inhibitor of this attenuation of T cell proliferation by unaltered BTNL9 protein as assayed by the methods described herein.

In some embodiments the substitutions can be conservative amino acid substitutions. Examples of conservative amino acid substitutions, unlikely to affect biological activity, include the following: alanine for serine, valine for isoleucine, aspartate for glutamate, threonine for serine, alanine for glycine, alanine for threonine, serine for asparagine, alanine for valine, serine for glycine, tyrosine for phenylalanine, alanine for proline, lysine for arginine, aspartate for asparagine, leucine for isoleucine, leucine for valine, alanine for glutamate, aspartate for glycine, and these changes in the reverse. See e.g. Neurath et al., *The Proteins,* Academic Press, New York (1979), the relevant portions of which are incorporated herein by reference. Further, an exchange of one amino acid within a group for another amino acid within the same group is a conservative substitution, where the groups are the following: (1) alanine, valine, leucine, isoleucine, methionine, norleucine, and phenylalanine; (2) histidine, arginine, lysine, glutamine, and asparagine; (3) aspartate and glutamate; (4) serine, threonine, alanine, tyrosine, phenylalanine, tryptophan, and cysteine; and (5) glycine, proline, and alanine.

Guidance as to what amino acids of BTNL9 can be altered without affecting its biological function is provided by the alignment below of the human BTNL9 amino acid sequence (top line, lower case letters, SEQ ID NO:2) to the mouse BTNL9 amino acid sequence (bottom line, upper case letters, SEQ ID NO:6) shown below. Residues shown in bold are residues characteristic of an IgV-like domain (for residues 37-150 of SEQ ID NO:2) or of an IgCl-like domain (for residues 151-257 of SEQ ID NO:2) or conservative variants thereof. Harpaz and Chothia (1994), J. Mol. Biol. 238: 528-539; Williams and Barclay (1988), Ann. Rev. Immunol. 6: 381-405; Peach et al. (1995), J. Biol. Chem. 270(36): 21181-1187, all of which are incorporated herein by reference.

These sequences, that is, the human and murine amino acid sequences shown in Table 3, are about 71% identical. Interestingly, the sequence of the second extracellular domain (from about position 151-257 of SEQ ID NO:2) and most of the intracellular domain (from about position 306-535 of SEQ ID NO:2) of BTNL9 are more highly conserved between mouse and human sequences than the sequence of the first, Ig-like extracellular domain. One of skill in the art will appreciate that non-conserved residues are less likely to play a role in determining the overall tertiary structure of a BTNL9 protein than conserved residues, since structure is more conserved in evolution than sequence. Bork et al. (1994), J. Mol. Biol. 242: 309-20. As used herein, "non-conserved residues" are amino acids within a BTNL9 protein that are not conserved when the human and the mouse BTNL9 protein sequences are compared, as in Table 3. Non-conserved amino acids are also less likely to play a direct role in BTNL9 function. For example, residues 50, 54,

TABLE 3 alignment of human and mouse BTNL9 amino acid sequences

```
  1 mvdlsvspdslkpvsltsslvflmhllllqpgepsse.vkvlgpeypila    49
    |  | ||    ||  :    |  :|   :|| ||   | .|:  | ||||| |||
  1 MADFSVFLGFLKQIPRCLS.IFFTYLLFLQLWEVNSDKVWVLGPEESILA    49

50 lvgeevefpchlwpqldaqqmeirwfrsqtfnvvhlyqeqqelpgrqmpa    99
    ||| ||||||  |     ||: |||||||| .|   |||:|||  |        ||
 50 RVGEAVEFPCRLSSYQDAEHMEIRWFRAQVSNVVYLYQEPQGRSSLQMAQ    99

100 frnrtklvkddiaygsvvlqlhsiipsdkgtygcrfhsdnfsgealwele   149
    |||||    ||| |||  |  :    ::|||.|  ||||| |||||||||  ||||
100 FRNRTLFEAYDIAEGSVNLHILKVLPSDEGRYGCRFLSDNFSGEATWELE   149

150 vaglgsdphlslegfkeggiqlrlrssgwypkpkvqwrdhqgqclppefe   199
    |||  |||||:||:||    ||||.  ||||||||||||| ||||||  || |
150 VAGSGSDPHISLQGFSGEGIQLQCSSSGWYPKPKVQWRGHQGQCLSPESE   199

200 aivwdaqdlfsletsvvvragalsnvsvsiqnlllsqkkelvvqiadvfv   249
    ||  .|| ||||||||:|| || |||| ||    || ||  ||||  |:||||||.
200 AITQNAQGLFSLETSVIVRGGAHSNVSCIIQNPLLPQKKEFVIQIADVFL   249

250 pgasawksafvat...lpl.llvlaalalgvlrkqrrsreklrkqaekrq   295
    |   | || |||  |    |||  |:||   |||       |   |   .|| ||  |..
250 PRMSPWKKAFVGTLVVLPLSLIVLTMLALRYFYKLRSFQEKQVKQGEEVR   299

296 ekltaeleklqteldwrraegqaewraaqkyavdvtldpasahpslevse   345
    ||||||||||||.||||||||||.|| ||||||||.||||||||||
300 .......EKLQTELDWRRSEGQAEWRAAQQYAADVTLDPATAHPSLEVSN   342

346 dgksvssrgappgpapghpqrfseqtcalslerfsagrhywevhvgrrsr   395
    .||.||||    |   | | |||||||||| || ||||.||||||||||||||
343 NGKTVSSRLGVPSIAAGDPQRFSEQTCVLSRERFSSGRHYWEVHVGRRSR   392

396 wflgaclaavpragparlspaagywvlglwngceyfvlaphrvaltlrvp   445
    |||||||  .|  |.|||||||||||||:||||  ||||||  ||||||  ||||
393 WFLGACLESVERSGPARLSPAAGYMVMGLWNRCEYFVLDPHRVALALRVP   442

446 prrlgvfldyeagelsffnvsdgshiftfhdtfsgalcayfrprahdgge   495
    |||:||  ||||||.|||||||||||| .|  |||||||  ||  |||||||  |
443 PRRIGVLLDYEAGKLSFFNVSDGSHIFSFTDTFSGALRAYLRPRAHDGSE   492

496 hpdplticplpvrgtgvpeendsdtwlqpyepadpaldww.......    535
    ||||:|||  |||||    |   |||||.| |||||||  |||   |
493 HPDPMTICSLPVRGPQVLEENDNDNWLQPYEPLDPA...WAVNEAVS    536
```

62, 63 of SEQ ID NO:2, and many others shown in Table 3 are neither identical nor similar. Thus, one of skill in the art would realize that alteration of residues that are neither identical or similar would be less likely to affect BTNL9 protein function than would alteration of identical or similar residues. Moreover, conservative substitutions (as described herein) are less likely to affect protein function that non-conservative substitutions. On the other hand, substitution or deletion of conserved residues (such as, for example, residues 43, 44, 47, 48, and 49 of SEQ ID NO:2), especially residues that are conserved in Ig-like domains (such as residues 52, 55, and 57 of SEQ ID NO:2), are more likely to impair biological function. One of skill in the art will also appreciate that substitutions that substantially upset the tertiary structure of a BTNL9 protein as predicted by programs such as, for example, DALI (Holm and Sander (1993), J. Mol. Biol. 233: 123-38), are also likely to impair function. Thus, the art provides considerable guidance as to what alterations can be made without affecting function. All variants and derivatives of BTNL9 protein, as meant herein, can inhibit the proliferation of T cells activated with an anti-CD3 antibody or can inhibit the ability of unmutated versions of BTNL9 protein to do so.

A BTNL9 protein can be at least 85%, 90%, 95%, 96%, 97%, 98%, or 99% identical to SEQ ID NO:2, wherein the alignment window is at least 50, 60, 75, 80, 90, or 100 amino acids long and wherein the BTNL9 protein can inhibit the proliferation of T cells activated with an anti-CD3 antibody. As discussed above, sequence mismatches with the mouse sequence and with other human BTNL family members can guide one of skill in the art as to where modifications in the sequence of SEQ ID NO:2 can be made without affecting function. In some embodiments, the insertions, deletions, or substitutions can occur at, or adjacent to, residues that are not conserved between human and mouse BTNL9. In some embodiments, these alterations occur at (in the case of deletions or substitutions) or adjacent to (in the case of insertions) one or more of the following residues of SEQ ID NO:2: 39, 45, 46, 50, 54, 60, 62-65, 69, 79, 80, 89, 91-95, 98, 99, 105-109, 113, 117, 119, 121, 122, 130, 136, 145, 153, 165-167, 173, 174, 188, 195, 198, 202, 203, 207, 219, 222, 227, 228, 232, 235, 240, 251, 252, 254, and 257. Alternatively, a BTNL9 protein can contain not more than 1, 2, 3, 4, 5, 6, 8, 10, 15, 20, 25, or 30 amino acid substitutions, deletions, or insertions relative to SEQ ID NO:2. The proteins described above are BTNL9 proteins as meant herein as long as they can inhibit the proliferation of T cells activated by an anti-CD3 antibody.

BTNL9 proteins may be glycosylated to varying degrees or not glycosylated. As an illustration, a BTNL9 protein of the invention may comprise one or more N- or O-linked glycosylation sites in addition to those already found in a protein comprising SEQ ID NO:2. SEQ ID NO:2 contains five potential N-linked glycosylation sites at positions 102, 139, 224, 464, and 516. One of skill in the art would be aware that asparagine residues that are part of the sequence Asn Xxx Ser/Thr (where Xxx is any amino acid except proline) can serve as sites of addition for N-glycans. In addition, there are many serine and threonine residues that may serve as O-linked glycosylation sites. Glycosylation may increase in vivo half life or alter biological activity. Variants of BTNL9 proteins also include proteins comprising one, two, three, four, five, six, seven, eight, nine, or ten more N- and/or O-linked glycosylation sites than are present in SEQ ID NO:2 as long as the resulting protein can inhibit the proliferation of T cells. Variant BTNL9 proteins also include those that have one, two, three, four, or five fewer N- and/or O-linked glycosylation sites than are present in SEQ ID NO:2 as long as they can inhibit the proliferation of T cells activated with an anti-CD3 antibody or can inhibit the ability of unmutated versions of BTNL9 protein to do so.

BTNL9 proteins, as meant herein, can be fusion proteins comprising at least one BTNL9 polypeptide, which can comprise an amino acid sequence that is a variant and/or a fragment of SEQ ID NO:2 (as explained above), and at least one other moiety. The other moiety can be a polypeptide other than a BTNL9 protein. The other moiety can also be a non-protein moiety such as, for example, a polyethylene glycol (PEG) moiety or a cytotoxic, cytostatic, luminescent, and/or radioactive moiety.

Attachment of PEG has been shown to increase the in vivo half life of at least some proteins. Moreover, cytotoxic, cytostatic, luminescent, and/or radioactive moieties have been fused to antibodies for diagnostic or therapeutic purposes, for example, to locate, to inhibit proliferation of, or to kill cells to which the antibodies can bind. Similarly, BTNL9 proteins fused to such moieties can be used to locate, to inhibit proliferation of, or to kill cells that BTNL9 can bind to, such as B cells, T cells, and/or other cells involved in immune response. Among such cytotoxic, cytostatic, luminescent, and/or radioactive moieties are, for example, maytansine derivatives (such as DM1), enterotoxins (such as a Staphylococcal enterotoxin), iodine isotopes (such as iodine-125), technetium isotopes (such as Tc-99m), cyanine fluorochromes (such as Cy5.5.18), ribosome-inactivating proteins (such as bouganin, gelonin, or saporin-S6), and calicheamicin, a cytotoxic substance that is part of a product marketed under the trademark MYLOTARG™ (Wyeth-Ayerst).

A variety of polypeptides other than BTNL9 can be fused to a BTNL9 polypeptide for a variety of purposes such as, for example, to increase in vivo half life of the protein, to facilitate identification, isolation and/or purification of the protein, to increase the activity of the protein, and to promote oligomerization of the protein.

Many polypeptides can facilitate identification and/or purification of a recombinant fusion protein of which they are a part. Examples include polyarginine, polyhistidine, or HAT™ (Clontech), which is a naturally-occurring sequence of non-adjacent histidine residues that possess a high affinity for immobilized metal ions. BTNL9 proteins comprising these polypeptides can be purified by, for example, affinity chromatography using immobilized nickel or TALON™ resin (Clontech), which comprises immobilized cobalt ions. See e.g. Knol et al. (1996), J. Biol. Chem. 27(26): 15358-15366. Polypeptides comprising polyarginine allow effective purification by ion exchange chromatography. Other useful polypeptides include, for example, the antigenic identification peptides described in U.S. Pat. No. 5,011,912 and in Hopp et al. (1988), Bio/Technology 6:1204. One such peptide is the FLAG® peptide, which is highly antigenic and provides an epitope reversibly bound by a specific monoclonal antibody, enabling rapid assay and facile purification of expressed recombinant fusion protein. A murine hybridoma designated 4E11 produces a monoclonal antibody that binds the FLAG® peptide in the presence of certain divalent metal cations, as described in U.S. Pat. No. 5,011,912. The 4E11 hybridoma cell line has been deposited with the American Type Culture Collection under Accession No. HB 9259. Monoclonal antibodies that bind the FLAG® peptide can be used as affinity reagents to recover a polypeptide purification reagent that comprises the FLAG® peptide. Other suitable protein tags and affinity reagents are: 1) those described in GST-Bind™ system (Novagen), which utilizes the affinity of glutathione-S-transferase fusion proteins for immobilized glutathione; 2) those described in the T7-TAG® affinity purification kit (Novagen), which utilizes the affinity of the amino terminal 11 amino acids of the T7 gene 10 protein for a monoclonal antibody; or 3) those described in the STREP-TAG® system (Novagen), which utilizes the affinity of an engineered form of streptavidin for a protein tag. Some of the above-mentioned protein tags, as well as others, are described in Sassenfeld (1990), TIBTECH 8: 88-93, Brewer et al., in *Purification and Analysis of Recombinant Proteins*, pp. 239-266, Seetharam and Sharma (eds.), Marcel Dekker, Inc. (1991), and Brewer and Sassenfeld, in *Protein Purification Applications*, pp. 91-111, Harris and Angal (eds.), Press, Inc., Oxford England (1990). The portions of these references that describe protein tags are incorporated herein by reference. Further, fusions of two or more of the tags described above, such as, for example, a fusion of a FLAG tag and a polyhistidine tag, can be fused to a BTNL9 protein of the invention.

Recombinant fusion proteins comprising polypeptides other than BTNL9 may have other kinds of unique advantages, such as, for example, a propensity to form dimers, trimers, or higher order multimers, an increased in vivo half-life, and/or an increased biological activity. A "higher order multimer" when used in conjunction with, for example, "dimer," means a multimer containing more than two polypeptide chains. When used in a phrase like "a trimer or a higher order multimer," the higher order multimer contains more than three polypeptide chains. Thus, a higher order multimer is one that has more polypeptide chains than the multimer it is compared to. Techniques for preparing fusion proteins are known, and are described, for example, in International Application WO 99/31241 and in Cosman et al. ((2001). Immunity 14: 123-133). As an illustration, a polypeptide that comprises an Fc region of an antibody, optionally an IgG antibody, or a substantially similar protein, can be fused to a BTNL9 polypeptide or fragment thereof. An Fc region of an antibody is a polypeptide comprising the most or all of hinge plus the $C_H2$, and the $C_H3$ domains from an antibody or immunoglobulin domains substantially similar to these. For discussion, see Hasemann and Capra, Immunoglobulins: Structure and Function, in William E. Paul, ed., Fundamental Immunology, Second Edition, 212-213 (1989). The Fc fragment can be a human IgG Fc, such as an IgG1, IgG2, IgG3, or IgG4 Fc. An Fc fragment can be a native human or animal Fc fragment. Truncated forms of Fc regions, that is, forms missing some portion of the hinge. $C_H2$, and/or $C_H3$ domains, that promote dimerization can also be used. Other portions of antibodies and other immunoglobulin isotypes can be used. Recombinant fusion proteins comprising Fc regions of antibodies are likely to form dimers or higher order multimers. Fusion proteins comprising various portions of antibody-derived proteins have been described by Ashkenazi et al. ((1991) Proc. Natl. Acad. Sci. USA 88:10535-39), Byrn et al. ((1990), Nature 344: 677-70), Hollenbaugh and Aruffo (in Current Protocols in Immunology, Suppl. 4, pp. 10.19.1-10.19.11 (1992)), Baum et al. ((1994), EMBO J. 13: 3992-4001) and in U.S. Pat. No. 5,457,035 and International Application WO 93/10151, the relevant portions of which are incorporated herein by reference. In some embodiments, an altered Fc region can have the advantage of having a lower affinity for Fc receptors compared to a wild type Fc region. This can be an advantage because it may lessen the lysis of cells to which such recombinant fusion proteins bind by immune effector cells. Such alterations to the Fc region are described in U.S. Pat. No. 5,457,035 and International Patent Application WO 93/10151, the relevant portions of which are incorporated herein by reference. Example 2 below describes the production of a fusion protein containing the extracellular region of human BTNL9 and the Fc region of a human IgG1 antibody.

A recombinant fusion protein comprising a BTNL9 protein can comprise a polypeptide comprising a leucine zipper. Among known leucine zipper sequences are sequences that promote dimerization and sequences that promote trimerization. See e.g. Landschulz et al. (1988), Science 240: 1759-64, the relevant portions of which is incorporated herein by reference. Leucine zippers comprise a repetitive heptad repeat, often with four or five leucine residues interspersed with other amino acids. Use and preparation of leucine zippers are well known in the art.

A BTNL9 fusion protein can comprise one or more peptide linkers. Generally, a peptide linker is a stretch of amino acids that serves to link plural polypeptides to form multimers and provides the flexibility or rigidity required for the desired function of the linked portions of the protein. Typically, a peptide linker is between about 1 and 30 amino acids in length. Examples of peptide linkers include, but are not limited to, -Gly-Gly-, GGGGS (SEQ ID NO:9), (GGGGS)n (SEQ ID NO:10), GKSSGSGSESKS (SEQ ID NO:11), GSTSGSGKSSEGKG (SEQ ID NO:12), GSTSGS-GKSSEGSGSTKG (SEQ ID NO:13), GSTSGS-GKSSEGKG (SEQ ID NO:14), GSTSGSGKPGSGEG-STKG (SEQ ID NO:15), EGKSSGSGSESKEF (SEQ ID NO:16) and GGGGSGGGGSGGGGS (SEQ ID NO:17). Linking moieties are described, for example, in Huston, J. S., et al., Proc. Natl. Acad. Sci. 85: 5879-83 (1988), Whitlow, M., et al., Protein Engineering 6: 989-95 (1993), Newton, D. L., et al., Biochemistry 35: 545-53 (1996), and U.S. Pat. Nos. 4,751,180 and 4,935,233. The relevant portions of these references, that is, the portions describing linkers, are incorporated herein by reference.

A recombinant BTNL9 fusion protein can comprise a BTNL9 protein that lacks its normal signal sequence and has instead a different signal sequence replacing it. The choice of a signal sequence depends on the type of host cells in which the recombinant protein is to be produced, and a different signal sequence can replace the native signal sequence. Examples of signal sequences that are functional in mammalian host cells include the following: the signal sequence for interleukin-7 (IL-7) described in U.S. Pat. No. 4,965,195; the signal sequence of human IgK (which is METDTLLLWVLLLWVPGSTG; SEQ ID NO:3); the signal sequence for interleukin-2 receptor described in Cosman et al. ((1984), *Nature* 312: 768); the interleukin-4 receptor signal peptide described in EP Patent 0 367 566; the type I interleukin-1 receptor signal peptide described in U.S. Pat. No. 4,968,607; and the type II interleukin-1 receptor signal peptide described in EP Patent 0 460 846. The portions of these references describing these signal sequences are incorporated herein by reference.

BTNL9 Nucleic Acids

The invention encompasses isolated nucleic acids, including, for example DNAs and RNAs, that encode the BTNL9 proteins described herein, which include proteins comprising the amino acid sequence of SEQ ID NO:2 and fragments and/or variants thereof. These nucleic acids are useful for, inter alia, producing recombinant proteins and detecting the presence of BTNL9 nucleic acids in tissue samples, e.g., for diagnostic uses. Such nucleic acids can be genomic DNA or cDNA. The nucleic acids can comprise an uninterrupted open reading frame encoding a BTNL9 protein. Nucleic acid molecules of the invention include DNA and RNA in both single-stranded and double-stranded form, as well as the corresponding complementary sequences. An "isolated nucleic acid" is a nucleic acid that has been separated from adjacent genetic sequences present in the genome of the organism from which the nucleic acid was isolated, in the case of nucleic acids isolated from naturally-occurring sources. In the case of nucleic acids synthesized chemically, such as oligonucleotides, or enzymatically from a template, such as polymerase chain reaction (PCR) products or cDNAs, it is understood that the nucleic acids resulting from such processes are isolated nucleic acids. An isolated nucleic acid molecule refers to a nucleic acid molecule in the form of a separate fragment or as a component of a larger nucleic acid construct.

Further, the invention encompasses fragments of a nucleic acid encoding a BTNL9 protein that can serve (1) as probes for detecting BTNL9 nucleic acids by a number of methods well known in the art, e.g., Southern and northern blotting, dot blotting, colony hybridizations, hybridization to an array, etc., (2) as polymerase chain reaction (PCR) primers to amplify BTNL9 nucleic acids, or (3) as a means to regulate expression of BTNL9 nucleic acids, e.g., through inhibition of expression with antisense nucleic acids (including peptide nucleic acids), ribozymes, triple helix-forming molecules, or interfering RNAs. DNAs that encode any of these RNAs are also BTNL9 nucleic acids as meant herein. PCR primers can comprise, in addition to BTNL9 nucleic acid sequences, other sequences such as restriction enzyme cleavage sites that facilitate the use of the amplified nucleic acid. PCR is described in the following references: Saiki et al. (1988), Science 239: 487-91; *PCR Technology*, Erlich, ed., Stockton Press, (1989). As explained below, PCR can be useful to detect over- or under-expression of BTNL9 mRNAs, and PCR primers can be taken from various parts of the BNTL9 gene and can also be selected to distinguish between different splice variants. Antisense RNAs (and DNAs encoding them), DNAs, or synthetic nucleotides and their use to regulate expression are well known in the art and are described in, e.g. Izant and Weintraub (1984), Cell 36(4): 1007-15; Izant and Weintraub (1985), Science 229(4711): 345-52; Harel-Bellan et al. (1988), J. Exp. Med. 168(6): 2309-18; Sarin et al. (1988), Proc. Natl. Acad. Sci. USA 85(20): 7448-51; Zon (1988), Pharm. Res. 5(9): 539-49; Harel-Bellan et al. (1988), J. Immunol. 140(7): 2431-35; Marcus-Sekura et al. (1987), Nucleic Acids Res. 15(14): 5749-63; Gambari (2001), Curr. Pharm. Des. 7(17): 1839-62; and Lemaitre et al. (1987), Proc. Natl. Acad. Sci. USA 84(3): 648-52. The portions of these references describing techniques of modulating gene expression using nucleic acids are incorporated by reference herein. Similarly, interfering RNAs (and DNAs encoding them) and their use to inhibit expression of selected genes are well known in the art and described in, e.g., Fjose et al. (2001), Biotechnol. Ann. Rev. 7: 31-57; Bosher and Labouesse (2000), Nature Cell Biol. 2: E31-B36. The relevant portions of these references are incorporated herein by reference. Further, ribozymes or DNAzymes can be targeted to cleave specific RNAs and thus used to inhibit gene expression as described in, e.g., Lewin and Hauswirth (2001), Trends Mol. Med. 7(5): 221-28; Menke and Hobom (1997), Mol. Biotechnol. 8(1): 17-33; Norris et al. (2000), Adv. Exp. Med. Biol. 465: 293-301; Sioud (2001), Curr. Mol. Med. 1(5): 575-88; and Santiago and Khachigian (2001), J. Mol. Med. 79(12): 695-706. The portions of these references describing these methods of modulating gene expression are incorporated by reference herein. Nucleic acids that can regulate BTNL9 expression can find use in in vivo or in vitro studies of BTNL9 function or as therapeutics, optionally, as gene therapy agents.

The present invention also includes nucleic acids comprising the sequence of SEQ ID NO:1 or a fragment thereof or nucleic acids that hybridize under moderately stringent conditions, and optionally highly stringent conditions, to nucleic acids comprising the nucleotide sequence of SEQ ID NO:1, which is the nucleotide sequence of the full length BTNL9 cDNA, wherein the nucleic acid encodes a protein that can inhibit the proliferation of T cells activated with an anti-CD3 antibody. Hybridization techniques are well known in the art and are described by Sambrook, J., E. F. Fritsch, and T. Maniatis (*Molecular Cloning: A Laboratory Manual*, Cold Spring Harbor Laboratory Press, Cold Spring Harbor, N.Y., chapters 9 and 11, (1989)) and *Current Protocols in Molecular Biology* (F. M. Ausubel et al., eds., John Wiley & Sons, Inc., sections 2.10 and 6.3-6.4 (1995)), the relevant portions of which are incorporated by reference herein. Moderately stringent conditions for filter hybridizations include hybridization in about 50% formamide, 6×SSC at a temperature from about 42° C. to 55° C. and washing at about 60° C. in 0.5×SSC, 0.3% SDS. Highly stringent conditions are defined as hybridization conditions as above, but with washing at approximately 68° C. in 0.2×SSC, 0.1% SDS. SSPE (1×SSPE is 0.15 M NaCl, 10 mM $NaH_2PO_4$, and 1.26 mM EDTA, pH 7.4) can be substituted for SSC (1×SSC is 0.15 M NaCl and 15 mM sodium citrate) in the hybridization and wash buffers; washes, optionally at least two washes, are performed for 15 minutes after hybridization is complete.

It should be understood that the wash temperature and wash salt concentration can be adjusted as necessary to achieve a desired degree of stringency by applying the basic principles that govern hybridization reactions and duplex stability, as known to those skilled in the art and described further below (see e.g., Sambrook et al., supra). When nucleic acids of known sequence are hybridized, the hybrid length can be determined by aligning the sequences of the nucleic acids (for example, using GAP) and identifying the region or regions of optimal sequence complementarity. The hybridization temperature for hybrids anticipated to be less than 50 base pairs in length should be 5 to 10° C. less than the melting temperature (Tm) of the hybrid, where Tm is determined according to the following equations. For hybrids less than 18 base pairs in length, Tm (degrees C.)=2(# of A+T bases)+4(# of G+C bases). For hybrids above 18 base pairs in length, Tm (degrees C.)=81.5+16.6 ($\log_{10}$ [$Na^+$])+0.41(% G+C)−(600/N), where N is the number of bases in the hybrid, and [$Na^+$] is the concentration of sodium ions in the hybridization buffer. Each such hybridizing nucleic acid has a length that is at least 15 nucleotides (or at least 18 nucleotides, or at least 20, or at least 25, or at least 30, or at least 40, or at least 50, or at least 100. Sambrook et al., supra.

BTNL9 nucleic acids include nucleic acids comprising the following polynucleotides: (1) all or a fragment of SEQ ID NO:1, wherein the fragment encodes a BTNL9 protein that can inhibit proliferation of T cells; (2) a polynucleotide including nucleotide sequences at least 80%, 85%, 90%, 95%, 97%, 98%, 99%, 99.5%, or 99.7% identical to SEQ ID NO:1, wherein the alignment window is at least 100, 125, 150, 175, 200, 225, 250, 300, 400, 500, 600, 800, 1000, or 1200 nucleotides long and wherein the sequence encodes a BTNL9 protein that can inhibit the proliferation of T cells activated with an anti-CD3 antibody; (3) fragments of SEQ ID NO:1 or substantially similar sequences that are useful for detecting or amplifying nucleic acids encoding the BTNL9 proteins of the invention or for regulating the expression of BTNL9 mRNAs and/or proteins; (4) a polynucleotide that comprises not more than 1, 2, 3, 4, 6, 8, 10, 15, 20, 25, or 30 alteration(s) of a single nucleotide relative to SEQ ID NO:1, wherein an alteration can be an insertion, deletion or substitution of a single nucleotide, and wherein the polynucleotide encodes a BTNL9 protein can inhibit the proliferation of T cells activated with an anti-CD3 antibody or can serve as an antagonist of such a protein; and (5) a polynucleotide that encodes a BTNL9 protein as described herein, which includes fragments, derivatives and variants of a human BTNL9 protein.

Methods of Making BTNL9 Proteins

BTNL9 proteins or anti-BTNL9 antibodies (or anti-idiotypic antibodies) can be made as follows. A nucleic acid that encodes a BTNL9 protein or an anti-BTNL9 antibody, as described herein, can be introduced into a vector, which can be introduced into a host cell. Vectors and host cells comprising nucleic acids encoding a BTNL9 protein or an anti-BTNL9 antibody are encompassed by the invention. The host cell containing the nucleic acids encoding a BTNL9 protein or an anti-BTNL9 antibody can be cultured under conditions such that the BTNL9 protein or the anti-BTNL9 antibody can be expressed. The expressed BTNL9 protein or anti-BTNL9 antibody can then be obtained from the medium in which the cells are cultured or from the cells and purified by any of the many appropriate means known in the art. In addition, genetic engineering methods for the production of BTNL9 proteins include the expression of the polynucleotide molecules in cell free expression systems, in cellular hosts, in tissues, and in animal models, according to known methods.

The vector can include a selectable marker and an origin of replication, for propagation in a host. The vector can further include suitable transcriptional or translational regulatory sequences, such as those derived from mammalian, microbial, viral, or insect genes, operably linked to the nucleic acid encoding the BTNL9 protein or the anti-BTNL9 antibody. Examples of such regulatory sequences include transcriptional promoters, operators, or enhancers, mRNA ribosomal binding sites, and appropriate sequences that control transcription and translation. Nucleotide sequences are operably linked when the regulatory sequence functionally relates to the DNA encoding the target protein. Thus, a promoter nucleotide sequence is operably linked to a BTNL9 nucleic sequence if the promoter nucleotide sequence directs the transcription of the anti-BTNL9 antibody- or BTNL9 protein-encoding sequence. If the BTNL9 protein is a fusion protein, a nucleic acid sequence encoding a portion of the fusion protein, for example, a signal sequence, can be part of a vector, and a nucleic acid encoding an anti-BTNL9 antibody or a BTNL9 protein can be inserted into the vector such that a protein comprising the added signal sequence plus the anti-BTNL9 antibody or BTNL9 protein is encoded by the vector.

Suitable host cells for expression of BTNL9 proteins or anti-BTNL9 antibodies include prokaryotic cells, yeast cells, plant cells, insect cells, and higher eukaryotic cells. The regulatory sequences in the vector will be chosen such that they are operable in the host cell. Suitable prokaryotic host cells include bacteria of the genera *Escherichia, Bacillus,* and *Salmonella,* as well as members of the genera *Pseudomonas, Streptomyces,* and *Staphylococcus.* For expression in prokaryotic cells, for example, in *E. coli,* the polynucleotide molecule encoding a BTNL9 protein or anti-BTNL9 antibody preferably includes an N-terminal methionine residue to facilitate expression of the recombinant polypeptide. The N-terminal methionine may optionally be cleaved from the expressed polypeptide. Suitable yeast host cells include cells from genera including *Saccharomyces, Pichia,* and *Kluveromyces.* Preferred yeast hosts are *S. cerevisiae* and *P. pastoris.* A suitable system for expression in an insect host cell is described, for example, in the review by Luckow and Summers ((1988), BioTechnology 6: 47), the relevant portions of which are incorporated herein by reference. Suitable mammalian host cells include the COS-7 line of monkey kidney cells (Guzman et al. (1981), Cell 23: 175-182), baby hamster kidney (BHK) cells, Chinese hamster ovary (CHO) cells (Puck et al. (1958), PNAS USA 60: 1275-1281), CV-I (Fischer et al. (1970), Int. J. Cancer 5: 21-27), 293 cells from human kidney (American Type Culture Collection (ATCC®) catalog no. CRL-10852™), and human cervical carcinoma cells (HELA) (ATCC® CCL 2). The relevant portions of the references referred to in this paragraph are incorporated herein by reference.

Expression vectors for use in cellular hosts generally comprise one or more phenotypic selectable marker genes. Such genes encode, for example, a protein that confers antibiotic resistance or that supplies an auxotrophic requirement. A wide variety of such vectors are readily available from commercial sources. Examples include pGEM vectors (Promega), pSPORT vectors, and pPROEX vectors (InVitrogen, Life Technologies, Carlsbad, Calif.), Bluescript vectors (Stratagene), and pQE vectors (Qiagen). Yeast vectors will often contain an origin of replication sequence from a 2μ yeast plasmid, an autonomously replicating sequence (ARS), a promoter region, sequences for polyadenylation, sequences for transcription termination, and a selectable marker gene. Vectors replicable in both yeast and *E. coli* (termed shuttle vectors) may also be used. In addition to the above-mentioned features of yeast vectors, a shuttle vector will also include sequences for replication and selection in *E. coli.* Direct secretion of the target polypeptides expressed in yeast hosts may be accomplished by the inclusion of nucleotide sequence encoding the yeast α-factor leader sequence at the 5' end of the BTNL9- or antibody-encoding nucleotide sequence. Brake (1989), Biotechnology 13: 269-280.

Examples of suitable expression vectors for use in mammalian host cells include pcDNA3.1/Hygro$^+$ (Invitrogen), pDC409 (McMahan et al. (1991), EMBO J. 10: 2821-2832), and pSVL (Pharmacia Biotech). Expression vectors for use in mammalian host cells can include transcriptional and translational control sequences derived from viral genomes. Commonly used promoter sequences and enhancer sequences that can be used to express BTNL9 RNA include, but are not limited to, those derived from human cytomegalovirus (CMV), Adenovirus 2, Polyoma virus, and Simian virus 40 (SV40). Methods for the construction of mammalian expression vectors are disclosed, for example, in Okayama and Berg ((1982) Mol. Cell. Biol. 2:161-170), Cosman et al. ((1986) Mol. Immunol. 23:935-941), Cosman et al. ((1984) Nature 312: 768-771), EP-A-0367566, and WO 91/18982. The relevant portions of these references are incorporated herein by reference.

BTNL9 Antibodies

Antibodies that bind specifically to the BTNL9 proteins described herein, anti-idiotypic antibodies that bind to anti- BTNL9 antibodies, and uses of these antibodies are encompassed by the invention. An anti-BTNL9 antibody can bind to a polypeptide consisting of the amino acid sequence of SEQ ID NO:2 or a fragment thereof such as amino acids 35 to 257 of SEQ ID NO:2. As used herein, specific binding of an epitope on a BTNL9 protein by a first antibody means that the first antibody can be displaced from the BTNL9 protein by another antibody that competes with the first antibody, but not by other anti-BTNL9 antibodies that do not compete with the first antibody for binding. Numerous competitive binding assays are known in the art.

Typically competition of antibodies for binding can be evaluated by a fluorescence activated cell sorting (FACS) assay. All antibodies of interest are biotinylated. The biotinylated antibodies are combined with cells known to express the antigen to which the antibodies bind. If the biotinylated antibodies bind to the cells as expected, a shift in fluorescence intensity should be observed. Pre-incubation of the cells with an unlabeled version of the same antibody should completely eliminate the observed shift in fluorescence. Pre-incubation with a different unlabeled antibody may completely or partially eliminate the fluorescence shift or have no effect. In the later case, one would conclude that the unlabeled antibody does not compete with the labeled antibody. In the former case, the antibodies do compete for binding, and, as meant herein, one would conclude that the epitopes are either fully or partially overlapping, depending whether the elimination of the shift in fluorescence was complete or partial. Among the antibodies contemplated are those that compete, either fully or partially, with any specifically provided anti-BTNL9 antibody.

In addition, the impact of a BTNL9 antibody on activation of anti-CD3-activated T cells in the presence or absence of a BTNL9 protein may provide additional useful information about the functional properties of an antibody. The invention includes monoclonal antibodies, each of which binds to a particular epitope of BTNL9, and monoclonal antibodies that compete with these for binding.

Epitopes on BTNL9 protein may comprise contiguous amino acids and also may comprise non-contiguous amino acids that are brought into proximity by the folding of a BTNL9 protein. Epitopes can be identified by methods known in the art, including the use of protein fragment or peptide libraries, alanine scanning, epitope extraction, epitope excision, or X-ray crystallography. See e.g. Leinonen et al. (2002), Clin. Chem. 48(12): 2208-16; Kroger et al. (2002), Biosens. Bioelectron. 17(11-12): 937-44; Zhu et al. (2001), Biochem. Biophys. Res. Commun. 282(4): 921-27; Obungu et at. (2009), Biochemistry 48: 7251-60. The relevant portions of these references, i.e., the portions describing method of epitope mapping, are incorporated herein by reference.

Antibodies can be polyclonal or monoclonal antibodies and can be produced by methods well known in the art. See, for example, *Monoclonal Antibodies, Hybridomas: A New Dimension in Biological Analyses,* Kennet et al. (eds.), Plenum Press, New York (1980); and *Antibodies: A Laboratory Manual,* Harlow and Land (eds.). Cold Spring Harbor Laboratory Press, Cold Spring Harbor, N.Y., (1988); Kohler and Milstein (1980) Proc. Natl. Acad. Sci., USA, 77: 2197; Kozbor et al. (1984), J. Immunol. 133: 3001-3005 (describing the human B-cell hybridoma technique); Cole et al., *Monoclonal Antibodies And Cancer Therapy,* Alan R. Liss, Inc., pp. 77-96 (1985) (which describes EBV-hybridoma technique); Kuby, *Immunology,* Second Edition, p. 162-64, W. H. Freeman and Co., New York (1994); the relevant portions of these references are incorporated herein by reference. Hybridoma cell lines that produce monoclonal antibodies specific for the BTNL9 proteins of the invention are also contemplated herein. Such hybridoma lines can be produced and identified by conventional techniques. The hybridoma producing an antibody of this invention can be cultivated in vitro or in vivo. Further, anti-BTNL9 antibodies can be produced in other cultured cells, including, for example, Chinese hamster ovary (CHO), HeLa, VERO, BHK, Cos, MDCK, 293, 3T3, myeloma (e.g. NSO, NSI), or WI38 cells, yeast cells, insect cells, and bacterial cells, including, for example, *Escherichia coli*. Such antibodies can be produced by introducing nucleic acids encoding the antibodies plus nucleic acids to enable expression of these nucleic acids into desired host cells. The antibodies can then be produced by culturing the cells into which these nucleic acids have been introduced. Monoclonal antibodies can be of any immunoglobulin class including IgG, IgM, IgE, IgA, IgD and any subclass thereof, such as, for example, IgG1, IgG2, IgG3, or IgG4.

Anti-BTNL9 antibodies can be full-length tetrameric antibodies comprising two heavy chains and two light chains, like those found in most mammalian species. Alternatively, anti-BTNL9 antibodies can be single chain antibodies comprising a heavy and a light chain variable region and, optionally, also one or more constant region-like domain (U.S. Pat. No. 4,946,778; Bird et al. (1988), Science 242: 423-26; Huston et al. (1988), Proc. Natl. Acad. Sci. USA 85: 5879-83), dimeric or multivalent antibodies (see e.g. Lantto et al. (2002), J. Gen. Virol. 83: 2001-05; Hudson and Souriau (2001), Expert Opin. Biol. Ther. 1(5): 845-55), tetrameric antibodies (see e.g. Janeway et al., Immunobiology: The Immune System in Health and Disease, Fifth Edition, Part II, Ch. 3, Garland Publishing (2001)), chimeric antibodies (Hudson and Souriau, supra; Boulianne et al. (1984), Nature 312:643-46; Morrison et al (1984), Proc. Natl. Acad. Sci. USA 81: 6851-55; Takeda et al. (1985), Nature 314: 452-54; Neuberger et al. (1985), Nature 314: 268-70), fully human antibodies produced in a non-human transgenic mammal (described in e.g., U.S. Pat. No. 6,150,584) or by in vitro selection (US Patent Application 2002/0058033) or humanized antibodies (Morrison et al., supra; Takeda et al., supra; Boulianne et al., supra). Further, antibodies can be "matured" by in vitro selection schemes to yield an antibody with altered properties such as, for example, a higher affinity for the epitope to which it binds. See e.g. Jackson et al. (1995), J. Immunol. 154(7): 3310-19; Pini and Bracci (2000), Curr. Protein Pept. Sci. 1(2): 155-69; Ellmark et al. (2002), Mol. Immunol. 39(5-6): 349; O'Connell et al. (2002), J. Mol. Biol. 321(1): 49-56; Huls et al. (2001), Cancer Immunol. Immunother. 50: 163-71; Hudson and Souriau, supra; Adams and Schier (1999), J. Immunol. Methods 231(1-2): 249-60; Schmitz et al. (2000), Placenta 21 Suppl. A: S106-12. Alternatively, fragments of antibodies such as, for example, Fab fragments, F(ab')$_2$ fragments, or single chain Fv fragments (scFv's) that can bind specifically to a BTNL9 protein of the invention are also encompassed by what is meant herein as an anti-BTNL9 antibody. See Kuby, supra, pp. 109-112 and Janeway et al., supra, for discussion of Fab and Fv fragments. The invention also encompasses anti-idiotypic antibodies that bind specifically to antibodies that bind specifically to BTNL9 proteins and that mimic the effects of BTNL9 proteins. Such anti-idiotypic antibodies find the same uses as BTNL9 proteins. Methods for generating anti-idiotypic antibodies are well known in the art. See e.g. Kuby et al., supra, at 371-72. Various kinds of recombinant and non-recombinant bispecific antibodies that can bind specifically to a BTNL9 protein of the invention and another protein are also contemplated. Various kinds of bispecific antibodies and methods for making them are described in e.g. U.S. Pat. Nos. 4,474,893, 6,060,285, and 6,106,833.

The anti-BTNL9 antibodies can be multimeric antibodies, including full-length, tetrameric bispecific antibodies containing two complete heavy chains and two complete light chain or multimeric monovalent antibodies containing, for example, a heavy chain plus a light chain plus an Fc region. Such multimeric antibodies can contain certain mutations in their Fc region that facilitate the formation of heterodimers. Such antibodies and mutations are described in International Patent Publication No. International Application WO 2009/089004 and US Application 2007/0105199, the portions of which describe such antibodies and mutations are incorporated by reference herein. The Fc regions in such antibodies can have native human sequences or sequences native to other species. Alternatively or in addition, the Fc regions of such antibodies can contain mutations in their Fc regions that either increase or decrease effector function by increasing or decreasing the affinity of various Fc receptors for the Fc region. Some such Fc alterations are discussed in U.S. Pat. No. 5,457,035 and International Patent Application Publication No. WO 93/10151, the relevant portions of which are incorporated herein by reference.

An antibody may contain only a single heavy or light chain variable region, optionally fused to another portion of an antibody as described in US Patent Application 2004/058820, the portions of which describe these single domain antibodies are incorporated herein by reference.

Some naturally-occurring antibodies, which have been found in camels and llamas, are dimers consisting of two heavy chains and include no light chains. Muldermans et al., 2001, *J. Biotechnol.* 74:277-302; Desmyter et al., 2001, *J. Biol. Chem.* 276:26285-90, the portions of which describe the structures of these antibodies are incorporated herein by reference. Anti-BTNL9 antibodies having this structure are among the anti-BTNL9 antibodies of the invention.

Anti-BTNL9 antibodies can have a variety of activities and uses. Anti-BTNL9 antibodies may be antagonistic antibodies that block or inhibit the biological function of BTNL9, for example by blocking or antagonizing BTNL9-dependent inhibition of T cell proliferation, which can be assayed by the methods described in the Examples herein. The antibodies can also be agonistic antibodies that bind to the BTNL9 counterstructure and mimic BTNL9 binding to inhibit T cell activation or proliferation. Such agonistic antibodies may also be anti-idiotypic antibodies that bind to anti-BTNL9 antibodies and also bind to the BTNL9 counterstructure and mimic the activity of BTNL9, that is, they inhibit the proliferation of T cells as described herein. Such antibodies can be used for the same uses as a BTNL9 protein. Anti-BTNL9 antibodies can be agonistic or antagonistic by, for example, stabilizing or disrupting the BTNL9 protein, possibly in combination with other proteins, on the cell surface. For example, an agonistic antibody may enhance the activity of BTNL9 by stabilizing the transmembrane form of BTNL9, or by stabilizing the interaction of a BTNL9 protein with other BTNL9 proteins or different proteins, on the surface of, for example, B cells or other cell types. Further, an antagonistic antibody may inhibit BTNL9 activity by destabilizing the transmembrane form of BTNL9, or by destabilizing interactions among multiple molecules of BTNL9 or interactions of BTNL9 with other proteins, on the cell surface of, for example, B cells or other cell types. Agonistic anti-BNTL9 antibodies can also bind transmembrane forms of BTNL9, causing it to transduce a biological signal into the cell on which it is expressed. An antagonistic anti-BTNL9 antibody can be used to enhance an immune response. Hence, antagonistic anti-BNTL9 antibodies can find use, for example, in a vaccine, for example in a vaccine to induce a response to a cancer-specific antigen.

The antibodies of the invention can also be used in assays to detect the presence of the BTNL9 proteins of the invention, either in vitro or in vivo. The antibodies also can be employed in purifying BTNL9 proteins of the invention by immunoaffinity chromatography.

Agonists and Antagonists BTNL9 Polypeptides

In addition to antagonist or agonist antibodies, other antibody-related molecules that can bind specifically BTNL9 proteins, such as affibodies (Rönnmark et al. (2002), J. Immunol. Methods 261(1-2): 199-211, the portion of which describes affibodies is incorporated by reference herein) and the biologically active peptides described in International Application WO 00/24782 (the portions of which describe these peptides are incorporated herein by reference) that can bind specifically to BTNL9 and inhibit the biological activity of BTNL9 proteins are encompassed by the invention. Further, BTNL9 antagonists include the nucleic acids described above that are useful for modulating expression of BTNL9 protein and/or mRNA, such as, for example, interfering RNAs (or DNAs that encode them) or antisense RNAs or DNAs.

Antagonists further include proteins that comprise amino acid sequences selected in vitro to bind to BTNL9 or its receptor and that can, optionally, interfere with the interaction of BTNL9 and its receptor. Alternatively, such proteins can be BTNL9 agonists that promote or mimic the biological function of BTNL9. Proteins that bind to BTNL9 or its receptor can be screened for their ability to interfere with the interaction of BTNL9 with its receptor, or, alternatively, a selection can be designed to obtain such proteins directly.

Proteins may be selected by a number of methods such as, for example, phage display or display of the surface of a bacterium. See e.g. Parmley and Smith (1989), Adv. Exp. Med. Biol. 251: 215-218; Luzzago et al. (1995), Biotechnol. Annu. Rev. 1: 149-83; Lu et al. (1995), Biotechnology (NY) 13(4): 366-372. In these methods, each member of a library of binding domains can be displayed on individual phage particles or bacterial cells, and bacteria or phage that bind to a protein of interest under chosen conditions can be selected. Nucleic acids encoding the selected binding domains can be obtained by growing the selected phage or bacteria and isolating nucleic acids from them.

Alternatively, a protein can be selected entirely in vitro. For example, each individual polypeptide in a library of potential binding domains can be attached to nucleic acids encoding it, and those that bind to the protein of interest under chosen conditions can be selected. Since the polypeptides are attached to nucleic acids encoding them, subsequent operations, such as amplifying, cloning, or sequencing nucleic acids encoding effective binding domains are facilitated. Various schemes for such selections are known in the art, including antibody-ribosome-mRNA particles, ribosome display, covalent RNA-peptide fusions, or covalent DNA-RNA-peptide fusions. He and Taussig (1997), Nucleic Acids. Res. 25(24): 5132-5134; Hanes and Pluckthun (1997), Proc. Natl. Acad. Sci. 94; 4937-4942; Roberts and Szostak (1997), Proc. Natl. Acad. Sci. 94: 12297-12302; Lohse and Wright (2001), Curr. Opin. Drug Discov. Devel. 4(2): 198-204; Kurz et al. (2000), Nucleic Acids Res.

28(18): E83; Liu et al. (2000), Methods Enzymol. 318; 268-93; Nemoto et al. (1997), FEBS Lett. 414(2): 405-08; U.S. Pat. No. 6,261,804; International Applications WO 00/32823; and WO 00/34784. The portions of these publications that describe how such selections can be done are incorporated by reference herein. Such proteins can be selected to be antagonists or agonists.

Therapeutic Uses

It is demonstrated herein that a BTNL9.Fc fusion protein can inhibit proliferation of activated T cells. BTNL9 also inhibits the production of cytokines, such as IL-2, TNFα, IFNγ, and IL-17, by activated T cells. It is further demonstrated by Fluorescence Activated Cell Sorting (FACS) that BTNL9 can bind to B cells and can bind to a limited extent to T cells. These findings indicate that BTNL9, or a molecule with the ability to agonize the BTNL9 pathway, may be useful as a therapeutic to treat autoimmune or inflammatory diseases that are mediated by T cells. Such diseases include, for example, systemic lupus erythematosus, Crohn's disease, ulcerative colitis, asthma, multiple sclerosis, rheumatoid arthritis, psoriasis, sarcoidosis, and fibrotic diseases including atherosclerosis, chronic obstructive pulmonary disease (COPD), cirrhosis, scleroderma, kidney transplant fibrosis, and pulmonary fibrosis.

The fact that BTNL9 exerts effects on T cells without exhibiting robust binding to T cells (as shown in the Examples below) can be explained in more than one way. It is possible that the interaction of BTNL9 with its counter-structure on the surface of T cells may be a low affinity or transient binding interaction. Alternatively, the BTNL9-Fc dimer molecule that we have used to test for binding to T cells may not be the correct multimer to bind strongly to T cells Molecules that block or inhibit the BTNL9 pathway may find use in oncology settings. An antibody that binds to either BTNL9 or its receptor and can block or inhibit the interaction between these molecules, can be used as a therapeutic to treat cancer. Other antagonists of BTNL9 described above could also be used. Some of the various cancers that might be treated with a BTNL9 pathway blocker include acute or chronic leukemias, lymphoma, non-Hodgkin's lymphoma, Hodgkin's disease, lymphocytic leukemias, lymphocytic or cutaneous lymphomas, carcinomas, sarcomas, thymomas, neoplasms of the mediastinum, breast cancer, prostate cancer, cancers of the head and neck, lung cancer, non-small cell lung cancer, small cell lung cancer, various kinds of skin cancer, cancer of the bladder, malignant gliomas, cancer of the esophagus, cancer of the stomach, cancer of the pancreas, hepatobiliary neoplasms, cancer of the small intestine, colon, or rectum, cancer of the kidney or ureter, testicular cancer, cancer of the urethra or penis, gynecologic tumors, ovarian cancer, sarcomas of the bone, cancers of the endocrine system, cutaneous melanoma, intraocular melanoma, neoplasms of the central nervous system, and plasma cell neoplasms, among many other cancers.

As noted above, a BTNL9 antagonist can also find use as an agent to make a vaccine more effective. BTNL9 could be used with a vaccine to induce a response against any antigen. Among these antigens are antigens that are highly expressed on cancer cells, such as cells from the cancers mentioned above. Among these cancer antigens are the following human proteins: WT1, MUC1, LMP2, EGFRvIII, HER-2/neu, MAGE-A3, NY-ESO-1, PSMA, GM2/GD2 synthase, CEA, MLANA/MART1, gp100, survivin, prostate-specific antigen (PSA), telomerase reverse transcriptase (hTERT), sarcoma translocation breakpoints, EPHA2, prostatic acid phosphatase (PAP), melanoma inhibitor of apoptosis (ML-IAP), α-fetoprotein (AFP), epithelial cell adhesion molecule (EpCAM), ERG, NA17.A2 peptide (VLPDVFIRC), paired box 3 (PAX3), anaplastic lymphoma kinase (ALK), androgen receptor, cyclin B1, polysialic acid, rho-related GTP-binding protein RhoC, v-myc myelocytomatosis viral related oncogene (MYCN), TRP-2, GD3 ganglioside, fucosyl GM1, mesothelin, prostate stem cell antigen (PSCA), MAGE-A1, CYP1B1, PLAC1, GM3, BORIS, tetranectin (TN), ETV6-AML1 (especially peptides including the breakpoint), NY-BR-1, RGS5, SART3, STn, carbonic anhydrase IX, PAX5, proacrosin binding protein sp32 precursor (OY-TES-1), sperm protein 17 (Sp17), LCK, high molecular weight melanoma-associated antigen (HMWMAA, also known as melanoma chondroitin sulfate proteoglycan), AKAP-4, SSX2, XAGE-1, B7H3 (also known as CD276), legumain, TIE2, prostate-associated gene 4 protein (PAGE-4), vascular endothelial growth factor receptor 2 (VEGFR2), protamine 2 (also known as MAD-CT-I), glomulin (also known as FAP), PDGFR-β, SSX2, SSX5, Fos-related antigen I, CD20, integrin αvβ3, 5T4 oncofetal antigen, CA IX, CD5, CD19, CD22 (also known as Siglec-2), CD30 (also known as TNFRSFI), CD33 (also known as Siglec-3), CD40, CD44V6, CD55, CD56 (also known as NCAM), CTLA-4 (also known as CD152), EGFR, GD2, HER2, HLA-DR10 (MHC II), IGF1R, IL-6, sialyl Lewis Y, TAG-72, TAL6, TRAILR2, VEGF, CD52 (also known as CAMPATH-1), CD4, CD73, CA125 (also known as MUC16), CD66e, CD80 (also known as B7-1), PDGFRβ, prostate specific membrane antigen (PSMA, also known as glutamate carboxypeptidase 2, among many other names). Cancer antigens also include the human herpes virus 4 protein LMP2, the human papillomavirus proteins E6 and E7, and the glycoceramide globo H (as described in Gilewski et al. (2001), Proc. Natl. Acad. Sci. 98(6): 3270-3275, the portions of which describe globo H are incorporated herein by reference), the α4 subunit of the α4β1 and α4β7 integrins, the α4β7 integrin, BAFF, APRIL, CD2, CD3, CD20, CD52, CD73, CD80, CD86, the $C_5$ complement protein, IgE, IL-1β, IL-5, IL-6R, IL-12, IL-23, and tumor necrosis factor α (TNF α).

"Treatment" of any disease mentioned herein encompasses an alleviation of at least one symptom of the disease, a reduction in the severity of the disease, or the delay or prevention of disease progression to more serious symptoms that may, in some cases, accompany the disease or lead to at least one other disease. Treatment need not mean that the disease is totally cured. A useful therapeutic agent needs only to reduce the severity of a disease, reduce the severity of one or more symptoms associated with the disease or its treatment, or delay the onset of more serious symptoms or a more serious disease that can occur with some frequency following the treated condition. For example, if the disease is an inflammatory bowel disease, a therapeutic agent may reduce the number of distinct sites of inflammation in the gut, the total extent of the gut affected, reduce pain and/or swelling, reduce symptoms such as diarrhea, constipation, or vomiting, and/or prevent perforation of the gut. A patient's condition can be assessed by standard techniques such as an x-ray performed following a barium enema or enteroclysis, endoscopy, colonoscopy, and/or a biopsy. Suitable procedures vary according to the patient's condition and symptoms.

A "therapeutically effective amount" of a drug used to treat a disease is an amount that can reduce the severity of a disease, reduce the severity of one or more symptoms associated with the disease or its treatment, or delay the onset of more serious symptoms or a more serious disease that can occur with some frequency following the treated condition.

The invention encompasses a method of treating inflammatory diseases such as systemic lupus erythematosus, Crohn's disease, ulcerative colitis, asthma, multiple sclerosis, rheumatoid arthritis, psoriasis, sarcoidosis, fibrotic diseases including atherosclerosis, cirrhosis, scleroderma, systemic lupus erythematosus, and pulmonary fibrosis. Such treatment involves using a therapeutically effective amount of a BTNL9 protein, or an agonistic antibody that binds to BTNL9 or its receptor, for a time sufficient to induce a sustained improvement over baseline of an indicator that reflects the severity of a particular disorder or the severity of symptoms caused by the disorder or to delay or prevent the onset of a more serious disease that follows the treated condition in some or all cases. The treatments of the invention may be used before, after, or during other treatments for the disorder in question that are commonly used, or they may be used without other treatments. For example, Crohn's disease and ulcerative colitis are commonly treated with sulfasalazine, 5-aminosalicyclic acid, or corticosteroids. These treatments may be used before, during, or after the treatments of the invention.

Similarly, cancer is often treated with chemotherapeutic agents and such agents can be used along with the BTNL9 antagonist therapeutics, such as anti-BTNL9 antibodies, described herein. Chemotherapeutic agents include, for example, the following therapeutics: alkylating agents (e.g. busulfan, temozolomide, cyclophosphamide, lomustine (CCNU), methyllomustine, streptozotocin, cis-diamminedichloroplatinum, aziridinylbenzo-quinone, and thiotepa); inorganic ions (e.g. cisplatin and carboplatin); nitrogen mustards (e.g. melphalan hydrochloride, ifosfamide, chlorambucil, and mechlorethamine HCl); nitrosoureas (e.g. carmustine (BCNU)); anti-neoplastic antibiotics (e.g. adriamycin (doxorubicin), daunomycin, mitomycin C, daunorubicin, idarubicin, mithramycin, and bleomycin); plant derivatives (e.g. vincristine, vinblastine, vinorelbine, paclitaxel, docetaxel, vindesine, VP-16, and VM-26); antimetabolites (e.g. methotrexate with or without leucovorin, 5-fluorouracil with or without leucovorin, 5-fluorodeoxyuridine, 6-mercaptopurine, 6-thioguanine, cytarabine, 5-azacytidine, hydroxyurea, deoxycoformycin, gemcitabine, and fludarabine); podophyllotoxins (e.g. etoposide, irinotecan, and topotecan); as well as actinomycin D, dacarbazine (DTIC), mAMSA, procarbazine, hexamethylmelamine, pentamethylmelamine, L-asparaginase, and mitoxantrone, among many known in the art. See e.g. Cancer: Principles and Practice of Oncology, $4^{th}$ Edition, DeVita et al., eds., J. B. Lippincott Co., Philadelphia, Pa. (1993), the relevant portions of which are incorporated herein by reference.

For autoimmune or inflammatory conditions, T cells can be removed from a patient, for example, through apheresis, and stimulated ex vivo using BTNL9, optionally plus other proteins, such that the T cells attain a regulatory or inhibitory phenotype. The T cells can then be transferred back into the patient. To stimulate the T cells to attain a regulatory or inhibitory phenotype, they can be incubated in the presence of a surface, for example, with beads or in microtiter plate wells, that is coated with human T cell agonistic anti-CD3 antibody, rBTNL9.Fc, and rB7-1.Fc or rB7-2.Fc in the presence of TGF-beta and IL-2. Alternatively, the surface could be coated with a combination of proteins that includes rBTNL9 or BTNL9.Fc plus an agonistic anti-CD3 antibody or a combination that includes only these proteins. In one embodiment, the agonistic anti-CD3 antibody, rBTNL9.Fc, and rB7-1.Fc or rB7-2.Fc can be, for example, at a molecular weight ratio of 2:10:2.5. The TGF-beta and IL-2 can be at appropriate concentrations, such as, for example, from about 0.05 to 5 ng/ml or at about 0.09 or 0.1 ng/ml for TGF-beta and from about 0.5 to 10 ng/ml or at about 10 ng/ml for IL-2. This can program the T cells to become inhibitory or regulatory. The T cells can be incubated in such a setting for, e.g., three to seven days and then harvested and delivered back to the same patient. Optionally, the T cells can be incubated about three, four, five, six, or seven days. In some embodiments, the T cells can also be rested, i.e., cultured in the presence of, for example, IL-2, without T cell receptor or costimulatory stimulus, and then restimulated as explained above one to four more times. The autoimmune or inflammatory conditions treatable with such a regime include, for example, systemic lupus erythematosus, Crohn's disease, ulcerative colitis, asthma, multiple sclerosis, rheumatoid arthritis, psoriasis, sarcoidosis, and fibrotic diseases including atherosclerosis, chronic obstructive pulmonary disease (COPD), cirrhosis, scleroderma, kidney transplant fibrosis, and pulmonary fibrosis.

Any of the above-described therapeutic agents can be administered in the form of a composition, that is, with one or more additional components such as a physiologically acceptable carrier, excipient, or diluent. For example, a composition may comprise a soluble BTNL9 protein as described herein plus a buffer, an antioxidant such as ascorbic acid, a low molecular weight polypeptide (such as those having less than 10 amino acids), a protein, amino acids, carbohydrates such as glucose, sucrose, or dextrins, chelating agent such as EDTA, glutathione, and/or other stabilizers, excipients, and/or preservatives. The composition may be formulated as a liquid or a lyophilizate. Further examples of components that may be employed in pharmaceutical formulations are presented in Remington's Pharmaceutical Sciences, $16^{th}$ Ed., Mack Publishing Company, Easton, Pa., (1980), the relevant portions of which are incorporated herein by reference.

Compositions comprising therapeutic molecules described above can be administered by any appropriate means including, but not limited to, parenteral, topical, oral, nasal, vaginal, rectal, or pulmonary (by inhalation) administration. If injected, the composition(s) can be administered intra-articularly, intravenously, intraarterially, intramuscularly, intraperitoneally, or subcutaneously by bolus injection or continuous infusion. Localized administration, that is, at the site of disease, is contemplated, as are transdermal delivery and sustained release from implants, skin patches, or suppositories. Delivery by inhalation includes, for example, nasal or oral inhalation, use of a nebulizer, inhalation in aerosol form, and the like. Administration via a suppository inserted into a body cavity can be accomplished, for example, try inserting a solid form of the composition in a chosen body cavity and allowing it to dissolve. Other alternatives include eye drops, oral preparations such as pills, lozenges, syrups, and chewing gum, and topical preparations such as lotions, gels, sprays, and ointments. In most cases, therapeutic molecules that are polypeptides can be administered topically or by injection or inhalation.

The therapeutic molecules described above can be administered at any dosage, frequency, and duration that can be effective to treat the condition being treated. The dosage depends on the molecular nature of the therapeutic molecule and the nature of the disorder being treated. Treatment may be continued as long as necessary to achieve the desired results. The periodicity of treatment may or may not be constant throughout the duration of the treatment. For example, treatment may initially occur at weekly intervals and later occur every other week. Treatments having durations of days, weeks, months, or years are encompassed by the invention. Treatment may be discontinued and then restarted. Maintenance doses may be administered after an initial treatment.

Dosage may be measured as milligrams per kilogram of body weight (mg/kg) or as milligrams per square meter of skin surface (mg/m$^2$) or as a fixed dose, irrespective of height or weight. These are standard dosage units in the art. A person's skin surface area is calculated from her height and weight using a standard formula. For example, a therapeutic BTNL9 protein or an antibody that binds to BTNL9 or its receptor can be administered at a dose of from about 0.05 mg/kg to about 10 mg/kg or from about 0.1 mg/kg to about 1.0 mg/kg. Alternatively, a dose of from about 1 mg to about 500 mg can be administered. Or a dose of about 5 mg, 10 mg, 15 mg 20 mg, 25 mg, 30 mg, 35 mg, 40, mg, 45, mg, 50 mg, 55 mg, 60 mg, 100 mg, 200 mg, or 300 mg can be administered.

The invention is described below with reference to specific examples. These examples are not meant to limit the invention in any way. It is understood for purposes of this disclosure, that various changes and modifications may be made to the invention that are well within the scope of the invention. Numerous other changes may be made which will readily suggest themselves to those skilled in the art and which are encompassed in the spirit of the invention disclosed herein and as defined in the appended claims.

EXAMPLES

Example 1

Expression of mRNA Encoding Human BTNL9 Protein in Human Immune Cells and Adult Human Tissues The following experiments were done in order to gather information on expression of mRNA encoding human BTNL9 in primary human immune cells and in various tissues.

Figure 2:
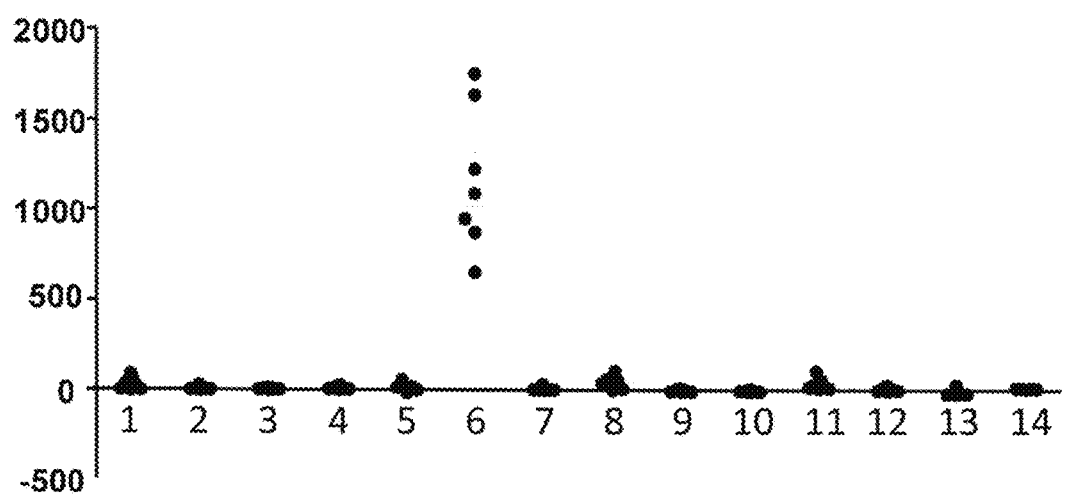
FIG. 2: This figure indicates relative amount of BTNL9 mRNA present in various primary human immune cells. Cells were isolated from leukopaks or whole blood from normal human donors, and RNA was assessed by hybridization to an Affymetrix array (Affymetrix GENECHIP™ HG-U133 Plus 2.0). The vertical axis indicates the intensity value for expression of BTNL9 mRNA generated using ROSETTA RESOLVER®. The various cell types tested are indicated along the x axis as follows: 1, peripheral blood mononuclear cells; 2, CD3$^+$ cells; 3, CD4$^+$ cells; 4, CD8$^+$ cells; 5, regulatory T cells; 6, CD19$^+$ cells; 7, natural killer (NK) cells; 8, NK-T cells; 9, monocytes; 10, macrophages.

Primary immune cells were isolated from whole blood or leukopaks via various commercially available selection methods from Stem Ceil Sciences (Palo Alto, Calif.) or Miltenyi Biotech (Germany). For example, the EASYSEP® Human T cell enrichment kit, in combination with the CD4$^+$ T cell enrichment kit (both from Stem Cell Sciences), was used to isolate CD4$^+$ T cells, while monocytes were isolated using the Miltenyi Monocyte Isolation Kit II. Such cell separations using such commercially available reagents are routine in the art. Macrophages were obtained through the ex vivo maturation of negatively-selected monocytes for seven days. Each isolated cell population was analyzed by fluorescence activated cell sorting (FACS) to determine whether the isolated cell population was expressing the expected cell surface proteins. RNA was isolated and assessed by Affymetrix array (Affymetrix GENECHIP™ HG-U1333 Plus 2.0). Data normalization and analysis for human BTNL9 transcript detection was performed using ROSETTA RESOLVER® software (Rosetta Biosoftware, Cambridge, Mass., USA). The results of these analyses are shown in FIG. 2. Among the various cell types tested, cells expressing CD19 on their cells surface (lane 6 in FIG. 2), that is, the B cells, expressed the highest amounts of BTNL9.

Human BTNL9 expression in adult human tissues was assessed by microarray analysis using the Affymetrix GENECHIP™ Human Genome 133 Plus 2.0 array (Affymetrix, Santa Clara, Calif., USA). The results of this analysis are shown in FIG. 3. These data indicate that human BTNL9 is widely expressed in many different tissues. Among the tissues exhibiting the highest BTNL9 mRNA expression were those from the following physical Structures: adrenal gland (lane 1 of FIG. 3), colon (lane 9 of FIG. 3), heart (lane 11 of FIG. 3), lung (lane 19 of FIG. 3), spleen (lane 26 of FIG. 3), thymus (lane 28 of FIG. 3), and white adipose tissue (lane 29 of FIG. 3).

Example 2

Preparation of Human BTNL9.Fc and Mouse BTNL2.Fc

The following describes how a fusion protein containing the extracellular region of human BTNL9 and the Fc portion of a human IgG1 antibody was made. A cDNA in an appropriate vector was constructed encoding the extracellular domain of human BTNL9 fused to a linker plus the human IgG1 Fc fragment. SEQ ID NO:18 provides the sequence of this cDNA, and SEQ ID NO:19 provides the amino acid sequence of the BTNL9.Fc protein encoded by this cDNA. Cos PKB cells were transfected with the BTNL9.Fc mammalian expression construct using LIPOFECTAMINE™ 2000 (Invitrogen) and cultured in complete Dulbecco's Modified Eagle Medium (DMEM) with 0.5% Low Ig Serum. These methods are described in detail by Ettehadieh et al., OVEREXPRESSIONS OF PROTEIN KINASE BA ENHANCES RECOMBINANT PROTEIN EXPRESSION IN TRANSIENT SYSTEMS in Animal Cell Technology; From Target to Market: Proceedings of the 17$^{th}$ ESACT Meeting, Tylösand, Sweden, Jun. 10-14, 2001, Vol. I, Lindner-Olsson et al., eds., pp. 31-35, Springer, 2001. The portions of this reference describing how to make a recombinant protein are incorporated herein by reference. Seven days post transfection, supernatants were harvested, and the BTNL9.Fc protein was purified by Protein A column chromatography (MABSELECT™ SuRe column, GE Healthcare).

A mouse BTNL2.Fc protein was made essentially as described in U.S. Pat. No. 7,244,822, wherein this construct is called BTL-II:Fc. This protein contains the extracellular region of the mouse BTNL2 protein fused to a human IgG1 Fc region. The portions of U.S. Pat. No. 7,244,822 describing this construction are incorporated by reference herein. The nucleic acid sequence encoding the mouse BTNL2.Fc protein and the amino acid sequence of the BTNL2.Fc protein are reported in SEQ ID NOs: 20 and 21 of U.S. Pat. No. 7,244,822, respectively.

Example 3

In Vitro Analysis of Murine CD4$^+$ T Cell Proliferation

The following experiment was done to determine the effects of a human BTNL9:Fc fusion protein on the proliferation of mouse CD4$^+$ T cells in vitro.

A single cell splenocyte suspension, which was prepared from spleens harvested from at least five female C57BL/6 mice per experiment, was used to purify CD4$^+$ T cells with the mouse EASYSEP™ CD4$^+$ negative selection kit (Stem Cell Sciences). Purity of CD4$^+$ T cells was greater than 90% as assessed by F ACS analysis. Tissue culture-treated microtiter plates were coated with variable concentrations of an anti-CD3 monoclonal antibody (Clone 2C11, BD Biosciences Pharmingen, San Diego, Calif., USA) and 10 µg/ml goat anti-human Fc antibody (Jackson ImmunoResearch, West Grove, Pa., USA) in PBS at 4° C. overnight. Wells were then washed with PBS and coated with the specified amount of the indicated Fc fusion protein for 4 hours at room temperature. Wells were again washed with PBS, and then 1-2×10$^5$ purified CD4$^+$ splenocytes/well were added. Proliferation of the CD4$^+$ T cells was determined by incorporation of $^3$H-thymidine (1 µCi/well) during the last 6 hours of the 72 hour culture. Fc fragment from a preparation of human IgG was used as a negative control. As positive controls, mouse BTNL2.Fc, which had been previously shown to inhibit proliferation of T cells, and human B7-2-Fc (purchased from R & D Biosystems), a known positive costimulator of T cells, were also included.

The results are shown in FIG. 4. Lanes 1 and 2 in FIG. 4 represent negative control assays containing 10 µg/ml and 2 µg/ml, respectively of Fc fragment from a preparation of human IgG. Lane 3 shows results from a positive control assay containing a human B7-2-Fc protein. Lane 4 shows results from an assay containing mouse BTNL2.Fc, a negative costimulatory molecule. Lanes 5 and 6 show results from assays containing 10 µg/ml and 2 µg/ml of human BTNL9.Fc, respectively. These data confirm the stimulatory effect of human B7-2-Fc and the inhibitory effect of mouse BTNL2.Fc on mouse T cell proliferation and indicate that human BTNL9.Fc can inhibit mouse T cell proliferation.

Example 4

In Vitro Analysis of Human CD4$^+$ T Cell Proliferation

The following experiment was done to determine the effects of a human BTNL9:Fc fusion protein on the proliferation of human CD4$^+$ T cells in vitro.

Human T cells were purified from human peripheral blood mononuclear cells using a human CD4$^+$ T cell isolation kit II (Miltenyi Biotech, Bergisch Gladbach, Germany, Catalog #130-091-155), resulting in a population of cells containing >90% CD4$^+$ cells. Like the mouse CD4$^+$ proliferation assays, tissue culture-treated microtiter plates were pre-coated with variable concentrations of anti-CD3 mAb (OKT3) and 10 µg/ml goat anti-human Fc (Jackson ImmunoResearch) in PBS at 4° C. overnight. Wells were then washed with PBS and coated with the specified amount of the indicated Fc fusion protein for 4 hours at room temperature. Wells were again washed with PBS and then 1-2×10$^5$ purified human CD4$^+$ T cells/well were added. Proliferation of CD4$^+$ T cells was determined by incorporation of $^3$H-thymidine (1 µCi/well) during the last 6 hours of the 72 hour culture. Fc protein p7.5Fc was used as a negative control since it does not bind human CD4$^+$ cells and has no known effect on T cell proliferation. Mouse BTNL2-FC was included as a positive control. Cells exposed to anti-CD3 antibody (OKT3) only were also included as an additional control.

The results are shown in FIG. 5. Lane 1 shows the results of an assay containing anti-CD3antibody and no additional protein. Lanes 2 and 3 show the results of assays containing anti-CD3 antibody plus the negative control protein p7.5-Fc at concentrations of 10 µg/ml and 2.5 µg/ml, respectively. Lanes 4-7 show the results of assays containing anti-CD3 antibody plus human BTNL9.Fc at concentrations of 20, 10, 5 and 2.5 µg/ml, respectively. Lane 8 shows the results of an assay containing anti-CD3 antibody and mouse BTNL2.Fc at a concentration of 10 µg/ml. These data show that human BTNL9.Fc inhibits human T cell proliferation in a concentration dependent manner.

Example 5

Production of Cytokines by Activated Human T Cells

In a standard anti-CD3 proliferation assay, as described above, human CD4$^+$ T cells were isolated and stimulated with an anti-CD3 antibody, with or without BTNL9.Fc (at a concentration previously shown to inhibit T cell proliferation) or various other Fc-containing proteins. After 72 hours of stimulation, 100 µl of supernatant was harvested from each condition. The supernatants were then assayed for cytokine levels using a customized commercially available kit for simultaneously detecting multiple cytokines (IL2, IL4, IL5, IL10, IL13, IL17, GM-CSF, TNFα, IFNγ and IL1β) sold by Meso Scale Discovery of Gaithersburg, Md. Such kit assays are, in principle, similar to ELISA assays, but use multiplexed detection technology.

FIGS. 6A-6E show the levels of interleukin-2 (FIG. 6A), tumor necrosis factor-α (FIG. 6B), interferon-γ (FIG. 6C), interleukin-17 (FIG. 6D), and interleukin-13 (FIG. 6E) that were detected. Lanes 1-7 in all panels represent the results of assays containing the following ingredients: (1), cells without anti-CD3 antibody or any additional protein; (2), cells with only anti-CD3 antibody; (3)-(5), cells with anti-CD3 antibody plus a preparation of human IgG, p7.5-Fc, or HB15-Fc, respectively; (6) cells with anti-CD3 antibody and mouse BTNL2.Fc; and (7) cells with anti-CD3 antibody and BTNL9.Fc. Like mouse BTNL2.Fc, BTNL9.Fc inhibited the expression of interleukin-17, interleukin-2, tumor necrosis factor-α, and interferon-γ, but not interleukin-13, by human CD4$^+$ T cells in response to stimulation by an anti-CD3 antibody.

Example 6

Cell Binding Studies

The following experiment was done to determine what specific cell types BTNL9 binds to. Single cell suspensions of mouse splenocytes were generated and then activated with 2 µg/ml of anti-CD3 antibody (2C11-mouse; OKT3-human), conconavalin A (Con A), or bacterial lipopolysaccharide (LPS) for 48 hours. Unstimulated cells were also included as controls. The unstimulated and stimulated cells were stained for 60 minutes on ice with huBTNL9.Fc or control Fc-containing proteins. Following a wash, bound Fc protein was detected with phycoerythrin (PE) conjugated F(ab')$_2$ goat anti-human Fc (Jackson ImmunoResearch) using FACS. In addition, these stained cells were costained with allophycocyanin (APC) conjugated CD3 or CD 19 (BD Biosciences) to specifically identify T cells and B cells, respectively, in the mixed cell populations. Samples were fixed and analyzed using a FACSCALIBUR™ flow cytometer (BD Immunocytometry Systems, San Jose, Calif., USA).

The resulting data indicated that BTNL9.Fc binds to mouse B cells stimulated with LPS, but not to unstimulated mouse B cells. Data not shown. Further data indicated that BTNL9.Fc binds to stimulated mouse T cells to only a limited degree and did not detectably bind to unstimulated mouse T cells. This may indicate that the interaction of BTNL9 with T cells is transient and/or low affinity, thus below the level of detection of our FACS assay.

Example 7

Inhibition of Human T Cell Proliferation is not Due to Cell Death

The following experiment was done to determine whether the inhibition of activated human T cell proliferation by BTNL9.Fc was due to cell death. An assay to detect lactate dehydrogenase (LDH) release following anti-CD3 antibody stimulation of human $CD4^+$ T cells in the presence or absence of BTNL9.Fc or control proteins was used to detect cytotoxicity. LDH is a stable cytoplasmic enzyme that is released into the supernatant upon plasma membrane damage and cell death. LDH was detected via a colorimetric reaction after 72 hours stimulation per manufacturer instructions (LDH Cytotoxicity Detection Kit, Clontech Laboratories, Inc, Mountain View, Calif., USA). Cells lysed with Triton-X were used as positive control for maximal LDH release due to cell death. The same experimental assay wells were used to detect cell proliferation inhibition and LDH release.

FIGS. 7A and 7B show the results of the LDH and proliferation assays, respectively. The sample represented in each lane of FIGS. 7A and 7B is described in detail in the brief description of these figures above. These data indicate that neither BTNL2.Fc nor BTNL9.Fc cause cytotoxic effects at concentrations that are sufficient to inhibit anti-CD3-stimulated T cell proliferation. Thus, these data suggest that the inhibition of cell proliferation by these proteins is not accompanied by cell death.

Example 8

Elevated BTNL9 Expression in Colon Tissue from Inflammatory Bowel Disease Patients The following experiment was done in order to determine whether BTNL9 is over- or under-expressed in colon tissue from donors with inflammatory bowel disease (Crohn's disease or ulcerative colitis) as compared to normal colon tissue. Expression of human BTNL9 was measured by quantitative real-time RT-PCR using the ABI PRISM® 7900HT sequence detection system (Applied Biosystems Inc, Foster City, Calif., USA) in colon tissues from donors without inflammatory bowel disease and from donors with either ulcerative colitis or Crohn's disease. The amount of BTNL9 mRNA expression detected was normalized to the expression of a housekeeping gene (β-actin). To generate cDNA, 20 ng of DNase-treated (DNA-free, Ambion) total RNA from diseased or normal tissue was reverse transcribed using a TAQMAN® reverse transcription kit (Applied Biosystems Inc.). This cDNA was used as template in the quantitative real-time RT-PCR using TAQMAN® Universal Buffer (Applied Biosystems Inc.) and a huBTNL9 probe set (purchased from Applied Biosystems: probe set Hs_00537320_m1). The PCR conditions were 50° C. for 2 minutes, then 95° C. for 10 minutes, then 40 cycles of the following temperature regime: 95° C. for 15 seconds followed by 60° C. for 1 minute. Each PCR reaction was run in triplicate for each biological sample included in the study.

The results are shown in FIG. 8. Each point on FIG. 8 represents data from one donor. Overall human BTNL9 mRNA expression in surgically resected colon tissue from donors with either ulcerative colitis (UC) or Crohn's disease (Crohns) was higher than in colon tissue from donors without inflammatory bowel disease. The difference in expression between normal and diseased tissue was statistically significant for both UC and Crohns tissue. These data indicate that BTNL9 mRNA is expressed at higher-than-normal levels in donors with either ulcerative colitis or Crohn's disease, the two most prevalent inflammatory bowel diseases. These findings suggest the possibility that BTNL9 may play a role in mediating a response to these diseases.

Example 9

Effects of State of Aggregation of BTNL9 on its Inhibition of T Cell Proliferation The purpose of this experiment was to determine whether the state of aggregation of BTNL9.Fc plays a role in its ability to inhibit T cell proliferation. Purified fractions of BTNL9.Fc in varying states of aggregation were obtained as follows. BTNL9.Fc, which was obtained from a culture supernatant of mammalian cells expressing it, was purified by Protein A chromatography. More specifically, BTNL9.Fc was loaded onto a Protein A column in 25 mM Tris, 150 mM NaCl, pH 7.4. The column was washed with 25 mM Tris, 0.5M L-arginine, pH 7.5 followed by 25 mM Tris, 150 mM NaCl, pH 7.4. BTNL9.Fc protein was eluted with 50 mM sodium citrate, 1M L-arginine, pH 3.5 and titrated to neutral pH with 1M Tris, pH 8.0. BTNL9.Fc was further purified by size exclusion chromatography (SEC) performed in 154 mM NaCl, 3.89 mM $KH_2PO_4$, 12 mM $Na_2HPO_4$, pH 7.2 (PBS). Each individual fraction was analyzed by analytical SEC and then conservatively pooled together into three fractions. Pooled fractions were concentrated and formulated into PBS with 50 µM EDTA and analyzed by analytic SEC, the results of which are shown in FIG. 9.

Pooled fraction 1 exhibited a single peak in analytic SEC having a molecular weight of about 958,000 daltons. Thus, fraction 1 contained almost entirely highly aggregated species. Pooled fraction 2 contained an approximately 50:50 mixture of two size classes of molecules, exhibiting two major peaks in analytic SEC having molecular weights of about 903,000 daltons and 531,000 daltons. Thus, fraction 2 contained a mixture of highly aggregated species and aggregated species of moderate size. Greater than 80% of fraction 3 consisted of smaller species. The main SEC peak of fraction 3 had an apparent molecular weight of about 197,000 daltons. This species may be a dimer, or at most a trimer, since the size of BTNL9.Fc as determined on a polyacrylamide gel run under reducing conditions is approximately 65,000 daltons. Data not shown. This size corresponds roughly to the expected molecular weight for a BTNL9.Fc monomer with some glysocylation. The species of about 531,000 daltons in fraction 2 may contain octamers since it is about eight times the size of the monomer. The species of over 900,000 daltons present in fractions 2 and 3 are higher order multimers, possibly 14-mers.

These purified fractions of BTNL9.Fc were used in assays of mouse and human $CD4^+$ T cell proliferation, performed as described above. The results of these experiments are shown in FIG. 10 (mouse T cells) and 11 (human T cells).

The results show that BTNL9.Fc fractions 1 and 2 exhibited statistically significant inhibition (relative to controls) of both mouse and human T cell proliferation. Fraction 1 was somewhat more effective in both assays than fraction 2, although the statistical significance of this difference was not determined. On the other hand, BTNL9.Fc fraction 3 showed no inhibition of either mouse or human T cell proliferation. Thus, these data indicate that higher order aggregates are more effective at inhibiting T cell proliferation than smaller species such as dimers or trimers. Based on the tentative identification of the major species in fraction 3 as a dimer, these data indicate that at least a trimer is required for BTNL9.Fc to inhibit T cell proliferation, although a higher order multimer such as at least a tetramer or pentamer may be required. Another way of viewing these data is that a species of at least about eight times the molecular weight of a monomer species of a BTNL9 protein can effectively inhibit T cell proliferation, whereas a species that is about three times the molecular weight of a monomer species of the BTNL9 protein cannot.

Example 10

Localization of BTNL9 in Capillary Endothelium in the Spleen

The following experiment was done to determine whether BTNL9 is expressed on vascular tissue in the spleen. Frozen human spleen tissue was fixed using 75% acetone/25% ethanol and stained in combination with antibodies specific for human BTNL9 and human CD31. CD31 is preferentially expressed on vascular endothelium. After incubation and washing, secondary antibodies were added to the tissue for detection via immunofluoresence. After a final wash, sections were stained with DAPI and imaged. The co-localization of BTNL9 and CD31 staining demonstrates BTNL9 expression on capillary endothelium in the spleen. The spleen also contains more weakly staining BTNL9$^+$/CD31$^+$ cells. Thus, these results indicate that BTNL9 is expressed on both vascular and non-vascular tissue in the spleen.

---

What is claimed is:

1. A method for treating a patient having an autoimmune or inflammatory disease comprising:
administering to the patient a therapeutically effective dose of a BTNL9 protein comprising (i) the amino acid sequence of amino acids 35-257 of SEQ ID NO:2, (ii) an amino acid sequence at least 95% identical to amino acids 35-257 of SEQ ID NO:2, wherein the alignment window of the amino acid sequence with amino acids 35-257 of SEQ ID NO:2 is at least 80 amino acids long, or (iii) an amino acid sequence that has no more than 10 insertions, deletions, or substitutions of a single amino acid relative to the sequence of amino acids 35-257 of SEQ ID NO:2, wherein the BTNL9 protein can inhibit the proliferation of a T cell stimulated by an anti-CD3 antibody.

2. The method of claim 1, wherein the autoimmune or inflammatory disease is selected from the group consisting of systemic lupus erythematosus, rheumatoid arthritis, an inflammatory bowel disease, Crohn's disease, ulcerative colitis, psoriasis, sarcoidosis, asthma, or a fibrotic disease.

3. The method of claim 1, wherein the BNTL9 protein does not comprise amino acids 258 to 277 of SEQ ID NO:2.

4. The method of claim 1, wherein the BTNL9 protein comprises an Fc portion of an antibody, wherein the Fc portion comprises an amino acid sequence that has not more than 15 insertions, deletions, or substitutions of a single amino acid relative to the amino acid sequence of a native human IgG Fc region, wherein the BTNL9 protein can bind to FcRn.

5. The method of claim 1, wherein:
   (i) the BTNL9 protein has a molecular weight at least about 8 times as large as the molecular weight of a polypeptide of (a) as measured by analytic SEC;
   (ii) the BTNL9 protein is a homotetramer or a higher order homomultimer;
   (iii) the BTNL9 protein is a homomultimer which is of a higher order than a homotetramer; and/or
   (iv) the BTNL9 protein is a heteromultimer.

6. A method of inhibiting T cell proliferation comprising: administering to the patient a therapeutically effective dose of a BTNL9 protein comprising (i) the amino acid sequence of amino acids 35-257 of SEQ ID NO:2, (ii) an amino acid sequence at least 95% identical to amino acids 35-257 of SEQ ID NO:2, wherein the alignment window of the amino acid sequence with amino acids 35-257 of SEQ ID NO:2 is at least 80 amino acids long, or (iii) an amino acid sequence that has no more than 10 insertions, deletions, or substitutions of a single amino acid relative to the sequence of amino acids 35-257 of SEQ ID NO:2, wherein the BTNL9 protein can inhibit the proliferation of a T cell stimulated by an anti-CD3 antibody.

7. The method of claim 6, wherein the BNTL9 protein does not comprise amino acids 258 to 277 of SEQ ID NO:2.

8. The method of claim 6, wherein the BTNL9 protein comprises an Fc portion of an antibody, wherein the Fc portion comprises an amino acid sequence that has not more than 15 insertions, deletions, or substitutions of a single amino acid relative to the amino acid sequence of a native human IgG Fc region, wherein the BTNL9 protein can bind to FcRn.

9. The method of claim 6, wherein:
   (i) the BTNL9 protein has a molecular weight at least about 8 times as large as the molecular weight of a polypeptide of (a) as measured by analytic SEC;
   (ii) the BTNL9 protein is a homotetramer or a higher order homomultimer;
   (iii) the BTNL9 protein is a homomultimer which is of a higher order than a homotetramer; and/or
   (iv) the BTNL9 protein is a heteromultimer.

\* \* \* \* \*